(12) United States Patent
Shim

(10) Patent No.: US 9,566,429 B2
(45) Date of Patent: *Feb. 14, 2017

(54) ELECTROMAGNETICALLY-COUNTERED DISPLAY SYSTEMS AND METHODS

(71) Applicant: Youngtack Shim, Seoul (CA)

(72) Inventor: Youngtack Shim, Seoul (CA)

(*) Notice: Subject to any disclaimer, the term of this patent is extended or adjusted under 35 U.S.C. 154(b) by 0 days.

This patent is subject to a terminal disclaimer.

(21) Appl. No.: 14/834,267

(22) Filed: Aug. 24, 2015

(65) Prior Publication Data

US 2016/0067482 A1 Mar. 10, 2016

Related U.S. Application Data

(63) Continuation of application No. 14/094,654, filed on Dec. 2, 2013, now Pat. No. 9,114,254, which is a
(Continued)

(51) Int. Cl.
| | | |
|---|---|---|
| *G02F 1/1333* | (2006.01) | |
| *A61N 1/16* | (2006.01) | |
| *H05K 9/00* | (2006.01) | |

(52) U.S. Cl.
CPC ............. *A61N 1/16* (2013.01); *H05K 9/0054* (2013.01); *H05K 9/0071* (2013.01); *H05K 2201/0707* (2013.01)

(58) Field of Classification Search
CPC ............. H04R 23/006; H04R 2201/003; B81B 3/0021; H05K 9/0071; H05K 9/0054; H05K 2201/0707; A61N 1/16
See application file for complete search history.

(56) References Cited

U.S. PATENT DOCUMENTS 3,973,066 A    8/1976 Smith, II et al.
4,263,500 A    4/1981 Springer et al.
(Continued)

OTHER PUBLICATIONS

U.S. Appl. No. 14/094,654, filed Dec. 2, 2013, Youngtack Shim.
(Continued)

*Primary Examiner* — Tuan D Nguyen
(74) *Attorney, Agent, or Firm* — Stein IP, LLC

(57) ABSTRACT

The present invention relates to an electromagnetically-countered display system including at least one wave source and at least one counter unit, where such a wave source irradiates harmful electromagnetic waves and the counter unit emits counter electromagnetic waves for countering the harmful waves therewith. More particularly, the present invention relates to various counter units for the electromagnetically-countered display system and to various mechanisms to counter the harmful waves with the counter units, e.g., by matching configurations of the counter units with those of the wave sources, by matching wavefronts of the harmful waves with those the counter waves, and so on. The present invention also relates to various methods of countering the harmful waves with such counter waves by source and/or wave matchings, various methods of providing the counter units for emitting the counter waves defining desired wave characteristics, and the like. The present invention further relates to various processes for providing the electromagnetically-countered display systems and their counter units. The present invention further relates to various electric and magnetic shields employed either alone or in conjunction with the counter units for minimizing irradiation of the harmful waves from the shaving system.

20 Claims, 8 Drawing Sheets

Related U.S. Application Data continuation of application No. 13/242,059, filed on Sep. 23, 2011, now Pat. No. 8,625,306, which is a continuation-in-part of application No. 12/985,031, filed on Jan. 5, 2011, now Pat. No. 8,588,437, which is a continuation-in-part of application No. 12/985,026, filed on Jan. 5, 2011, now Pat. No. 8,588,436, which is a continuation-in-part of application No. 12/985,042, filed on Jan. 5, 2011, now abandoned, which is a continuation-in-part of application No. 12/961,111, filed on Dec. 6, 2010, now Pat. No. 8,369,105, which is a continuation-in-part of application No. 12/318,546, filed on Dec. 31, 2008, now Pat. No. 8,035,990, which is a continuation of application No. 11/510,667, filed on Aug. 28, 2006, now Pat. No. 7,876,917.

(56) References Cited

U.S. PATENT DOCUMENTS

| | | |
|---|---|---|
| 4,271,350 A | 6/1981 | Crowley |
| 4,309,597 A | 1/1982 | Crowley |
| 4,323,761 A | 4/1982 | Hubner et al. |
| 4,382,174 A | 5/1983 | Barns |
| 4,436,986 A | 3/1984 | Carlson |
| 4,459,461 A | 7/1984 | Spencer |
| 4,585,922 A | 4/1986 | Berenson |
| 4,595,838 A | 6/1986 | Kerschgens |
| 4,656,334 A | 4/1987 | Endo et al. |
| 4,659,905 A | 4/1987 | Gabrosek et al. |
| 4,684,785 A | 8/1987 | Cole |
| 4,908,497 A | 3/1990 | Hjortsberg |
| 5,081,341 A | 1/1992 | Rowe |
| 5,218,185 A | 6/1993 | Gross |
| 5,403,992 A | 4/1995 | Cole |
| 5,410,127 A | 4/1995 | LaRue et al. |
| 5,448,677 A | 9/1995 | Fell et al. |
| 5,628,123 A | 5/1997 | Chan |
| 5,701,681 A | 12/1997 | Wonka et al. |
| 5,784,800 A | 7/1998 | Santhouse et al. |
| 5,787,601 A | 8/1998 | Stelly |
| 5,805,406 A | 9/1998 | Mailand |
| 5,810,911 A | 9/1998 | Behrendt et al. |
| 5,837,971 A | 11/1998 | Lee |
| 5,841,943 A | 11/1998 | Nosenchuck |
| 5,875,562 A | 3/1999 | Fogarty |
| 5,884,008 A | 3/1999 | Goldberg |
| 5,912,811 A | 6/1999 | Mackta |
| 5,966,833 A | 10/1999 | Andis |
| 5,996,243 A | 12/1999 | Chang et al. |
| 6,003,239 A | 12/1999 | Liebenthal et al. |
| 6,011,903 A | 1/2000 | Nosenchuck |
| 6,052,915 A | 4/2000 | Turner |
| 6,067,724 A | 5/2000 | Depoyian |
| 6,085,435 A | 7/2000 | Russi |
| 6,097,009 A | 8/2000 | Cole |
| 6,148,537 A | 11/2000 | Altamore |
| 6,153,856 A | 11/2000 | Lee |
| 6,177,658 B1 | 1/2001 | White et al. |
| 6,188,837 B1 | 2/2001 | Kwan |
| 6,191,930 B1 | 2/2001 | Ramchandani |
| 6,205,674 B1 | 3/2001 | Kaizuka |
| 6,205,677 B1 | 3/2001 | Yune |
| 6,222,162 B1 | 4/2001 | Keane |
| 6,222,988 B1 | 4/2001 | Behrendt et al. |
| 6,226,450 B1 | 5/2001 | Lee |
| 6,269,549 B1 | 8/2001 | Carlucci et al. |
| 6,285,828 B1 | 9/2001 | Cafaro |
| 6,300,597 B1 | 10/2001 | Lee |
| 6,310,332 B1 | 10/2001 | Gerrard |
| 6,314,236 B1 | 11/2001 | Taylor |
| 6,363,215 B1 | 3/2002 | Cafaro |
| 6,378,225 B1 | 4/2002 | Slingo |
| 6,393,718 B1 | 5/2002 | Harris et al. |
| 6,408,533 B2 | 6/2002 | Sakamoto |
| 6,449,870 B1 | 9/2002 | Perez et al. |
| 6,466,679 B1 | 10/2002 | Husung |
| 6,481,116 B1 | 11/2002 | Slingo |
| 6,601,316 B2 | 8/2003 | Shaw, II |
| 6,640,049 B1 | 10/2003 | Lee et al. |
| 6,650,061 B1 | 11/2003 | Urayama et al. |
| 6,689,989 B2 | 2/2004 | Irwin, Sr. et al. |
| 6,713,724 B1 | 3/2004 | Carr et al. |
| 6,718,651 B2 | 4/2004 | Perez et al. |
| 6,725,562 B2 | 4/2004 | Nakagawa et al. |
| 6,732,449 B2 | 5/2004 | Evanyk |
| 6,732,450 B1 | 5/2004 | Chen |
| 6,756,572 B2 | 6/2004 | Lee |
| 6,770,854 B1 | 8/2004 | Keane |
| 6,798,982 B2 | 9/2004 | Ryu et al. |
| 6,885,810 B2 | 4/2005 | Allwhon et al. |
| 6,889,445 B1 | 5/2005 | Varona et al. |
| 6,891,102 B2 | 5/2005 | Rashid |
| 6,907,678 B2 | 6/2005 | Cruz |
| 6,927,533 B1 | 8/2005 | Ito et al. |
| 6,966,125 B2 | 11/2005 | Rago et al. |
| 7,030,546 B2 * | 4/2006 | Han .................. G02F 1/133604 313/402 |
| 7,876,917 B2 | 1/2011 | Shim |
| 2004/0047620 A1 | 3/2004 | Ruben |
| 2004/0168337 A1 | 9/2004 | Curtin |
| 2004/0169969 A1 | 9/2004 | Takeda |
| 2004/0172847 A1 | 9/2004 | Saida et al. |
| 2004/0195235 A1 | 10/2004 | Kim et al. |
| 2004/0208337 A1 | 10/2004 | Anciant |
| 2005/0069303 A1 | 3/2005 | Maione et al. |
| 2005/0091866 A1 | 5/2005 | Attaway et al. |
| 2005/0108889 A1 | 5/2005 | Leventhal |
| 2005/0108890 A1 | 5/2005 | Park |
| 2005/0150501 A1 | 7/2005 | Opitz |
| 2005/0229422 A1 | 10/2005 | Mattinger et al. |
| 2005/0229424 A1 | 10/2005 | Hur |
| 2008/0084681 A1 * | 4/2008 | Naito .................. H05K 9/0096 361/818 |
| 2009/0168314 A1 * | 7/2009 | Park .................. G02F 1/133308 361/679.02 |
| 2009/0185102 A1 * | 7/2009 | Lee .................. G02F 1/13452 349/58 |
| 2010/0046709 A1 * | 2/2010 | Ueki .................. A61B 6/032 378/98 |
| 2010/0194668 A1 * | 8/2010 | Adzhalov .......... G02F 1/0322 345/6 |

OTHER PUBLICATIONS

U.S. Appl. No. 13/242,059, filed Sep. 23, 2011, Youngtack Shim.
U.S. Appl. No. 12/985,031, filed Jan. 5, 2011, Youngtack Shim.
U.S. Appl. No. 12/985,026, filed Jan. 5, 2011, Youngtack Shim.
U.S. Appl. No. 12/985,042, filed Jan. 5, 2011, Youngtack Shim.
U.S. Appl. No. 12/961,111, filed Dec. 6, 2010, Youngtack Shim.
U.S. Appl. No. 12/318,546, filed Dec. 31, 2008, Youngtack Shim.
U.S. Appl. No. 11/510,667, filed Aug. 28, 2006, Youngtack Shim.

* cited by examiner

ELECTROMAGNETICALLY-COUNTERED DISPLAY SYSTEMS AND METHODS

CROSS-REFERENCE TO RELATED APPLICATIONS

This application is a continuation application of U.S. patent application Ser. No. 14/094,654, filed on Dec. 2, 2013, entitled "Electromagnetically-Countered Display Systems And Methods", which is a continuation of U.S. patent application Ser. No. 13/242,059, filed on Sep. 23, 2011, issued to U.S. Pat. No. 8,625,306 entitled "Electromagnetically-countered display systems and methods", which is a continuation-in-part application of U.S. patent application Ser. No. 12/985,031, filed on Jan. 5, 2011, issued to U.S. Pat. No. 8,588,437 entitled "Genetic electromagnetically-countering processes", which is a continuation-in-part application of U.S. patent application Ser. No. 12/985,026, filed on Jan. 5, 2011, issued to U.S. Pat. No. 8,588,436 entitled "Generic electromagnetically-countered methods", which is a continuation-in-part application of U.S. patent application Ser. No. 12/985,042, filed on Jan. 5, 2011 entitled "Electromagnetically-countered systems and methods by maxwell equations", which is a continuation-in-part application of U.S. patent application Ser. No. 12/961,111, filed on Dec. 6, 2010, issued to U.S. Pat. No. 8,369,105 entitled "Generic electromagnetically-countered systems", which is a continuation-in-part application of U.S. patent application Ser. No. 12/318,546, filed on Dec. 31, 2008, issued to U.S. Pat. No. 8,035,990 entitled "Electromagnetically-countered display systems and methods", which is a continuation application of U.S. patent application Ser. No. 11/510,667, filed Aug. 28, 2006, issued to U.S. Pat. No. 7,876,917 entitled "Generic electromagnetically-countered systems and methods", which is continuation-in-part application of U.S. patent application Ser. No. 11/510,667, filed on Aug. 28, 2006, issued to U.S. Pat. No. 7,876,917 entitled "Generic electromagnetically-countered systems and methods". All disclosures of the document(s) named above are incorporated herein by reference.

BACKGROUND OF THE INVENTION

1. Field of the Invention

The present invention relates to an electromagnetically-countered display system including at least one wave source and at least one counter unit, where such a wave source irradiates harmful electromagnetic waves and the counter unit emits counter electromagnetic waves for countering the harmful waves therewith. More particularly, the present invention relates to various counter units for the electromagnetically-countered display system and to various mechanisms to counter the harmful waves with the counter units, e.g., by matching configurations of the counter units with those of the wave sources, by matching wavefronts of the harmful waves with those the counter waves, and so on. The present invention also relates to various methods of countering the harmful waves with such counter waves by source and/or wave matchings, various methods of providing the counter units for emitting the counter waves defining desired wave characteristics, and the like. The present invention further relates to various processes for providing the electromagnetically-countered display systems and their counter units. The present invention further relates to various electric and magnetic shields employed either alone or in conjunction with the counter units for minimizing irradiation of the harmful waves from the display system.

2. Description of the Related Art

It is now well established in the scientific community that electromagnetic waves with varying frequencies irradiated by various devices may be hazardous to human health. In some cases, such electromagnetic waves in mega- and giga-hertz range may be the main culprit, whereas the 60-hertz electromagnetic waves may be the main health concern in other cases. It cannot be too emphasized that it is very difficult to shield against magnetic waves of the 60-hertz electromagnetic waves which have wavelengths amounting to thousands of kilometers and that such 60-hertz magnetic waves are omnipresent in any corner of the current civilization.

However, intensity of such electromagnetic waves typically decreases inversely proportional to a square of a distance from a source of such waves to a target. Accordingly, potentially adverse effects from such electromagnetic waves may be minimized by maintaining a safe distance from such a source. Some electrical devices, however, are intended to be used in a close proximity to an user, where examples of the conventional electrical devices include various display devices from which an user are to acquire visual images. In general, the user may be able to more easily obtain such images from the display devices with larger screens at a greater distances than those with smaller screens, while misleading the user that the greater distance from the screens may protect him or her from such waves. Those devices with larger screens irradiate more stronger harmful electromagnetic waves than those with the smaller screens and, accordingly, the greater distance attainable with such larger screens are offset by the greater amplitudes of such harmful waves.

Therefore, there is an urgent need for various counter units capable of being incorporated into various prior art display devices in order to convert such devices to an electromagnetically-countered display systems and to minimize irradiation of such harmful electromagnetic waves therefrom. There is a need to provide a feasible solution for countering the harmful waves irradiated by various waves sources of the display devices of different shapes, sizes, and/or light-emitting mechanisms. There is a need to provide a feasible solution for countering such harmful waves which are irradiated by such wave sources as well while defining wavefronts of various characteristics.

SUMMARY OF THE INVENTION

The present invention relates to an electromagnetically-countered display system with at least one wave source irradiating harmful electromagnetic waves and at least one counter unit for emitting counter electromagnetic waves and for countering the harmful waves by the counter waves, e.g., by canceling at least a portion of the harmful waves with the counter waves in a target space and/or by suppressing the harmful waves with such counter waves from propagating toward the target space. More particularly, the present invention relates to counter units for the electromagnetically-countered display systems and to various mechanisms for countering the harmful waves irradiated by various base units of the wave source with the counter units. Accordingly, the counter unit may be shaped, sized, and/or arranged for matching its configuration with that of at least one of the base units of the wave source, thereby emitting such counter waves which automatically match wave characteristics of the harmful waves. In the alternative, the counter unit may be shaped, sized, and/or disposed in an arrangement which is defined along one or more wavefronts of such harmful waves, thereby emitting the counter waves automatically matching wave characteristics of such harmful waves. The present invention also relates to various counter units provided as analogs of at least one of the base units of the wave source, where the analog approximates (or simplifies) at least one of the base units which is more complex than the counter unit, where the three- or two-dimensional base unit is simplified (or approximated) as the two- or one-dimensional analog, and the like. The present invention also relates to multiple counter units simpler than at least one of such base units but disposed in an arrangement approximating such a shape and/or arrangement of the base unit. The present invention also relates to the counter unit which may be shaped and/or sized according to the configuration of at least one of the base units and disposition thereof. In addition, the present invention relates to various countering modes where a single counter unit may counter a single base unit or all (or at least two but not all) of multiple base units, where multiple counter units may counter a single base unit, a greater number of the base units or a less number of multiple units, and the like. The present invention further relates to various electric and/or magnetic shields which may be used either alone or in conjunction with at least one of the counter units to minimize irradiation of the harmful waves by at least one of the base units.

The present invention relates to various methods of countering such harmful waves irradiated by various base units of multiple wave sources of the EMC display system by the counter waves by the source or wave matchings. More particularly, the present invention relates to various methods of forming the counter unit as an analog of at least one of the base units and emitting the counter waves matching such harmful waves, various methods of approximating at least one of the base units by the simpler counter unit for the countering, and various methods of approximating at least one of the base units by multiple simpler counter units. The present invention relates to various methods of disposing the counter unit along the wavefronts of the harmful waves and emitting the counter waves matching the wavefronts of the harmful waves, and various methods of disposing multiple counter units along the wavefronts of the harmful waves and emitting the counter waves with the counter units matching the wavefronts. The present invention also relates to various methods of adjusting the wavefronts of the counter waves by disposing the counter unit closer to and/or farther away from the target space with respect to at least one of the base units, various methods of controlling radii of curvature of such wavefronts of the counter waves by incorporating one or multiple counter units emitting such waves with the same or opposite phase angles, and various methods of manipulating such wavefronts of the counter waves by disposing one or multiple counter units of the shape similar to or different from that of at least one of the base units. The present invention also relates to various methods of countering the harmful waves irradiated from a single or multiple base units with the counter waves emitted by a single or multiple counter units. Accordingly, the present invention also relates to various methods of emitting the counter waves by a single counter unit to counter the harmful waves irradiated by one or more base units and various methods of emitting the counter waves emitted from two or more counter units for countering such harmful waves irradiated from a single or multiple base units. In addition, the present invention also relates to various methods of minimizing irradiation of such harmful waves by incorporating the electric shields, by incorporating the magnetic shields, by incorporating one or both of such shields in conjunction with the above counter units, and the like.

The present invention further relates to various processes for providing various counter units for such EMC display systems and various EMC systems incorporating therein one or multiple counter units. More particularly, the present invention relates to various processes for providing such counter units capable of emitting the counter waves defining such wavefronts similar to (or different from) the shapes of the counter units, various processes for forming the counter units as the above analogs of at least one of such base units, various processes for providing the counter units emitting the counter waves having the similar or opposite phase angles, various processes for providing the counter units defining the wavefronts shaped similar to such harmful waves, and various processes for disposing the counter units in a preset arrangement and emitting thereby the counter waves of the wavefronts similar to such an arrangement. The present invention also relates to various processes for assigning a single counter unit in order to counter the harmful waves irradiated by a single base unit for the local countering or to counter the harmful waves irradiated by multiple base units for the global countering, various processes for assigning multiple counter units to counter the harmful waves irradiated from a single base unit for the global countering, and to counter the harmful waves irradiated by multiple base units for the local and/or global countering depending on numbers of the counter and base units. The present invention also relates to various processes for including such electric and/or magnetic shields for minimizing the irradiation of the harmful waves and various processes for minimizing the irradiation of such harmful waves by employing such shields and/or the above counter units.

Accordingly, a primary objective of the present invention is to provide an electromagnetically-countered display system (to be abbreviated as an "EMC display system," as an "EMC system," or simply as a "system" hereinafter) which is capable of minimizing irradiation of the harmful waves from at least one base unit of at least one wave source by countering the harmful waves with the counter waves. Therefore, a related objective of this invention is to provide an EMC display system capable of countering the harmful waves by canceling at least a portion of the harmful waves by the counter waves and/or by suppressing the harmful waves by the counter waves from propagating toward a preset direction. Another related objective of this invention is to counter the harmful waves by such counter waves not all around at least one base unit of the EMC system but only in the target space (or area) defined on only one side of the system. In general, such a target space is defined between at least one of the base units and an user of the system (or a specific body part of the user). Another related objective of this invention is to arrange the counter waves to define the phase angles at least partially opposite to those of the harmful waves so that such counter waves cancel and/or suppress the harmful waves when propagated to the target space. Another related objective of this invention is to arrange such counter waves to define the phase angles at least partially similar to those of such harmful waves so that the counter waves counter the harmful waves when propagated to the target space from an opposite side of such a base unit. Another related objective of this invention is to emit the counter waves from the same or opposite side of at least one of such base units with respect to the target space while manipulating their phase angles so that the counter waves emitted by different counter units counter the harmful waves in the target space.

Another objective of the present invention is to provide the EMC display system with at least one counter unit for emitting the counter waves. Therefore, a related objective of this invention is to match at least one feature or configuration (e.g., each meaning a shape, a size, an arrangement, and the like) of the counter unit with the feature or configuration of at least one of the base units such that the counter waves emitted by the counter unit match the harmful waves irradiated from the base unit. Another related objective of this invention is to match the shape of a single counter unit with that of a single base unit so that the counter waves emitted by the counter unit may match the harmful waves irradiated by at least one of the base units. Another related objective of this invention is to match the shape of a single counter unit with an arrangement of multiple base units such that the counter waves emitted by the counter unit match a sum of the harmful waves irradiated by such base units. Another related objective of this invention is to dispose multiple counter units in an arrangement matching the shape of a single base unit so that a sum of the counter waves emitted by the counter units match the harmful waves irradiated by at least one of the base units. Another related objective of this invention is to arrange multiple counter units in an arrangement matching an arrangement of multiple base units such that a sum of the counter waves emitted by multiple counter units matches a sum of the harmful waves irradiated by multiple base units. Another related objective of this invention is to provide such counter units while using the least amount of electrically conductive, semiconductive, and/or insulative materials, while minimizing a total volume or a size of the counter units, minimizing a total mass of such counter units, and the like. Another related objective of this invention is to emit the counter waves by the counter units while using the least electrical energy, drawing the least amount of electric current and/or voltage from at least one of the base units or other parts of the EMC system, and the like.

Another objective of the present invention is to form an EMC display system including at least one counter unit matching the shape of at least one of the base units. Therefore, a related objective of this invention is to form the counter unit as an one-, two- or three-dimensional analog of the three-dimensional base unit and to counter a single or multiple base units with the single or multiple analogs. Another related objective of this invention is to provide the counter unit as an one- or two-dimensional analog of the three-dimensional base unit and to counter a single or multiple base units with the single or multiple analogs. Another related objective of this invention is to form the counter unit as an one- or two-dimensional analog of the two-dimensional base unit and to counter a single or multiple base units with a single or multiple analogs. Another related objective of this invention is to fabricate the counter unit as an one-dimensional analog of the two-dimensional base unit and to counter a single or multiple base units with a single or multiple analogs. Another related objective of this invention is to define the counter unit as an one-dimensional analog of an one-dimensional base unit and to counter a single or multiple base units using a single or multiple analogs. Another related objective of this invention is to provide such counter units as one-, two-, and/or three-dimensional analogs of an one-, two-, and/or three-dimensional base units and to counter at least one of the base units of the mixed dimension with the counter units of the mixed dimension. In these objectives, all of the counter units emit the counter waves capable of matching the harmful waves irradiated by at least one of the base units. Another related objective of this invention is to form the counter unit conforming to the shape of at least one of the base units for matching such harmful waves with the counter waves emitted therefrom. Another related objective of this invention is to provide the counter unit not conforming to the shape of at least one of the base units but disposed in an arrangement for matching the harmful waves by the counter waves emitted therefrom. Another related objective of this invention is to provide the counter unit in a shape of one or multiple wires, strips, sheets, tubes, coils thereof, spirals, meshes thereof, mixtures thereof, combinations thereof, and/or arrays thereof in order to match the shape of at least one of the base units and to emit the counter waves matching such harmful waves. Another related objective of this invention is to dispose any of the counter units in a preset distance from at least one of the base units in order to match at least some wavefronts of the harmful waves with at least some wavefronts of the counter waves. Another related objective of this invention is to incorporate any of the counter units in a preset arrangement with respect to any of the base units to match at least some wavefronts of the counter waves with at least some wavefronts of the harmful waves.

Another objective of the present invention is to form an EMC display system including at least one counter unit of a size operatively matching a size of at least one of the base units and emitting the counter waves capable of matching the harmful waves irradiated from at least one of the base units. Therefore, a related objective of this invention is to provide the counter unit to be larger, wider, and/or longer than at least one of the base units and disposed between the target space and at least one of the base units, where such an arrangement will be referred to as the "front arrangement" hereinafter. Another related objective of this invention is to form the counter unit defining a length, a width, and/or a height similar (or identical) to those of at least one of the base units and disposed laterally or side by side to such a base unit with respect to the target space for the matching, where this arrangement is to be referred to as the "lateral arrangement" hereinafter. Another related objective of this invention is to form the counter unit which is smaller, narrower, and/or shorter than at least one of the base units and preferably disposed on an opposite side of the target space with respect to such a base unit for the matching, where such an arrangement is to be referred to as the "rear arrangement" hereinafter. Another related objective of this invention is to enclose at least a portion of the counter unit by at least one of the base units or, in the alternative, to enclose at least a portion of the base unit by the counter unit for such matching, where this arrangement is to be referred to as the "concentric arrangement" hereinafter. Another related objective of this invention is to dispose multiple counter units in the front, lateral, rear or concentric arrangement with respect to a single base unit for such matching. Another related objective of this invention is to provide a single or multiple counter units disposed in the front, lateral, rear or concentric arrangement with respect to multiple base units for such matching. Another related objective of this invention is to provide multiple counter units all of which are to be disposed in only one of such front, lateral, rear, and concentric arrangements with respect to all of multiple base units or at least two of which are to be disposed in different (or mixed) arrangements with respect to at least two of multiple base units for the matching.

Another objective of the present invention is to provide an EMC display system incorporating at least one counter unit into a disposition (e.g., an orientation, alignment, and/or distance) matching that of at least one of the base units. Therefore, a related objective of this invention is to orient or align the counter unit along a propagation direction of the harmful waves, along a direction in which the electric current flows in at least one of the base units, along a direction in which the electric voltage is applied thereacross, along a direction of the long and/or short axes of such counter and/or base units for the matching, and the like. Another related objective of this invention is to form multiple counter units all of which are oriented or aligned along the same direction and/or axis, at least two of which are oriented or aligned along different directions and/or axes, all of which are oriented in different directions and/or axes for the above matching, and the like. Another related objective of this invention is to axially align the counter unit with respect to at least one of the base units such that the counter waves emitted by the counter unit axially align with the harmful waves irradiated by at least one of the base units for the matching, where such an arrangement will be referred to as an "axial alignment" hereinafter. Another related objective of this invention is to axially misalign such a counter unit with (or from) at least one of the base units and to dispose the counter unit in a preset arrangement for such matching, where such an arrangement is to be referred to as an "off-axis alignment" hereinafter. Another related objective of this invention is to provide multiple counter units each (or at least two) of which may be disposed in the axial or off-axis alignment relative to a single base unit for the matching. Another related objective of this invention is to form a single or multiple counter units disposed in the axial or off-axis alignment with respect to multiple base units for such matching. Another related objective of this invention is to form multiple counter units all of which are disposed in the axial or off-axis alignment with respect to all of multiple base units or, in the alternative, at least two of which are disposed in different or mixed alignments relative to at least two of multiple base units for such matching. Another related objective of this invention is to dispose the counter unit in a preset distance from at least one of the base units such that at least some wavefronts of the counter waves emitted by the counter unit match at least some wavefronts of the harmful waves irradiated by at least one of the base units for the matching. Another related objective of this invention is to dispose a single counter unit in preset distances from each (or at least two) of multiple base units for such matching. Yet another related objective of this invention is to also dispose multiple counter units in preset distances from a single base unit or, in the alternative, at preset distances from each (or at least two) of multiple base units for the matching.

Another objective of the present invention is to form an EMC display system including at least one counter unit for emitting the counter waves of amplitudes matching those of such harmful waves. Therefore, a related objective of this invention is to form the counter unit emitting such counter waves of amplitudes greater than those of the harmful waves, where such a counter unit is disposed farther away from the target space with respect to at least one of such base units or in the rear arrangement for such matching. Another related objective of this invention is to provide the counter unit emitting the counter waves of amplitudes similar or identical to those of the harmful waves, where such a counter unit is disposed side by side with at least one of the base units with respect to the target space or in the lateral arrangement for such matching. Another related objective of this invention is to provide the counter unit emitting such counter waves of amplitudes less than those of the harmful waves, where such a counter unit is disposed closer to the target space than at least one of the base units or in the front arrangement for such matching. Another related objective of this invention is to provide multiple counter units each emitting the counter waves a sum of which has amplitudes which is greater than, similar to or less than those of a single base unit, which is greater than, similar to or less than those of all of multiple base units, which is greater than, similar to or less than those of at least two but not all of multiple counter units, and the like.

Another objective of the present invention is to form an EMC display system including at least one counter unit which emits the counter waves capable of matching at least a portion of the harmful waves and, therefore, countering the harmful waves. Therefore, a related objective of this invention is to provide the counter unit for emitting such counter waves defining multiple wavefronts matching at least one of the wavefronts of the harmful waves in the target space. Another related objective of this invention is to dispose the counter unit along at least a portion of at least one of such wavefronts of the harmful waves to emit the counter waves capable of matching such a portion of the wavefront of such harmful waves. Another related objective of this invention is to dispose multiple counter units along at least a portion of at least one of the wavefronts of the harmful waves and to emit the counter waves a sum of which matches the portion of the wavefront of the harmful waves. Another related objective of this invention is to dispose such a counter unit across at least two different wavefronts of the harmful waves but to emit the counter waves capable of matching at least a portion of at least one another of the wavefronts of the harmful waves. Another related objective of this invention is to form multiple counter units at least two of which are disposed across at least two of the wavefronts of the harmful waves but which also emit the counter waves capable of matching such a portion of the wavefront of the harmful waves. Another related objective of this invention is to shape and size the counter unit and to emit the counter waves defining radii of curvature matching those of at least a portion of the harmful waves. Another related objective of this invention is to dispose the counter unit in a preset position and/or in a preset distance from at least one of the base units in which the counter waves have the radii of curvature matching those of at least a portion of the harmful waves. Another related objective of this invention is to shape and size multiple counter units for emitting such counter waves a sum of which has the radii of curvature matching the harmful waves irradiated from a single or multiple base units. Another related objective of this invention is to form the counter unit in a shape of one or multiple wires, strips, sheets, tubes, coils thereof, spirals thereof, meshes thereof, mixtures thereof, combinations thereof, and/or arrays thereof, and then to emit such counter waves capable of matching at least a portion of at least one wavefront of such harmful waves irradiated by at least one of such base units. Another related objective of this invention is to provide the counter unit in a solid shape without forming any openings or holes thereacross for the matching. Another related objective of this invention is to provide the counter units as at least one array defining multiple holes or openings thereacross for such matching.

Another objective of the present invention is to form an EMC display system including at least one counter unit for emitting the counter waves and locally countering such harmful waves irradiated by at least one of the base units. Therefore, a related objective of this invention is to provide a single counter unit for locally countering such harmful waves irradiated by single base unit with the counter waves. Another related objective of this invention is to provide multiple counter units each of which locally counters the harmful waves irradiated by only one of the same (or less) number of base units with the counter waves emitted from each of multiple counter units. Another related objective of this invention is to provide a single or multiple counter units defining a feature (or configuration) similar (or identical) to that of a single or multiple base units for the local countering. Another related objective of this invention is to provide a single or multiple counter units for emitting the counter waves defining the wavefronts matching at least one of the wavefronts of the harmful waves irradiated by a single base unit or multiple base units for the local countering. Another related objective of this invention is to form multiple counter units at least one of which defines a feature (or configuration) similar (or identical) to that of at least one of the base units, while at least another of which defines the wavefronts matching at least one of the wavefronts of the harmful waves irradiated from at least one of the base units for the local countering.

Another objective of the present invention is to form an EMC display system including at least one counter unit emitting the counter waves and globally countering the harmful waves irradiated by at least one of the base units. Therefore, a related objective of this invention is to form one or multiple counter units each emitting the counter waves for globally matching such harmful waves irradiated by only one or a less number of base units. Another related objective of this invention is to form a single counter unit for globally countering a sum of such harmful waves irradiated by multiple base units with such counter waves. Another related objective of this invention is to form multiple counter units each globally countering the harmful waves irradiated by at least two base units with such counter waves emitted by each of multiple counter units. Another related objective of this invention is to form a single or multiple counter units defining a feature (or configuration) which is similar (or identical) to that of at least two or a greater number of base units for the global countering. Another related objective of this invention is to provide a single or multiple counter units emitting the counter waves of the wavefronts matching at least one of the wavefronts of the harmful waves irradiated by at least two or a greater number of base units for the global countering. Another related objective of this invention is to provide multiple counter units at least one of which defines the feature (or configuration) similar (or identical) to those of at least two base units and at least another of which defines the wavefronts matching at least one wavefront of the harmful waves irradiated by at least two of other base units for such local countering.

Another objective of the present invention is to form an EMC display system including at least one counter unit disposed in a preset position (or location) defined relative to at least one of the base units and/or target space. Therefore, a related objective of this invention is to dispose the counter unit on or over an exterior surface of at least one of such base units, to dispose the counter unit below or on an interior surface of at least one of such base units, to embed at least a portion of the counter unit into at least one of the base units, and the like. Another related objective of this invention is to dispose the counter unit on or over an exterior surface of a body of the system, to dispose the counter unit on or below an interior surface of the body, to embed at least a portion of the counter unit into the body, to dispose the counter unit between the body and at least one of the base units, and the like. Another related objective of this invention is to dispose the counter unit in a preset relation to the body by, e.g., exposing therethrough at least a portion of the counter unit, enclosing only a (or an entire) portion of the counter unit inside the body, and the like.

Another objective of the present invention is to form an EMC display system including at least one counter unit emitting the counter waves propagating along preset directions. Therefore, a related objective of this invention is to arrange the counter unit to emit such counter waves always in a fixed direction with respect to at least one of the base units so that the counter waves also propagate in a direction defined in a preset relation with respect to a direction of propagation of the harmful waves, e.g., parallel, perpendicular, and/or at a preset angle to the harmful waves. Another related objective of this invention is to arrange the counter unit to emit the counter waves along variable directions with respect to a direction of propagation of the harmful waves, where the counter unit is arranged to vary its arrangement and/or orientation, to receive such electric current and/or voltage in variable directions for varying the direction of the counter waves, and the like. Another related objective of this invention is to arrange the counter unit to emit the counter waves in a direction which is adaptively determined by variable directions of propagation of such harmful waves, where the counter unit may change the direction of the counter waves as described hereinabove. Therefore, the counter unit may change an extent of countering based upon its arrangement and/or orientation. Another related objective of this invention is to synchronize the direction of propagation of the counter waves with that of the harmful waves based on the preset relation disclosed hereinabove. Another related objective of this invention is to arrange the counter unit to control the amplitudes of such counter waves in various mechanisms similar to those for manipulating the directions thereof.

Another objective of the present invention is to form an EMC display system with at least one counter unit and to supply the electric energy thereto to counter such harmful waves with the counter waves emitted therefrom. Therefore, a related objective of this invention is to provide the counter unit with the electric current and/or voltage supplied to at least one of such base units. Another related objective of this invention is to provide the counter unit with at least a portion but not an entire portion of the electric current or voltage supplied to at least one of such base units. Another related objective of this invention is to provide the counter unit with only a portion of the current or voltage of which the amplitudes and/or direction may also be modified before being supplied thereto. In all of the examples, the current or voltage supplied to the counter unit may be automatically synchronized with the current or voltage supplied to at least one of such base units. Another related objective of this invention is to supply the counter unit with electric current or voltage which is not the current or voltage supplied to at least one of such base units but which is at least partially synchronized with the current or voltage supplied to such a base unit. Another related objective of this invention is to manipulate the amplitudes and/or directions of the current or voltage based on configurations and/or dispositions of the counter unit. Another related objective of this invention is to electrically couple the counter unit to at least one of the base units in a parallel, series or hybrid mode. Another related objective of this invention is to supply the electric current and/or voltage in various sequences such as, e.g., first to at least one of the base units and then to the counter unit, first to the counter unit then to at least one the base units, first to one of multiple counter units and then to the rest of the counter units or base unit, first to one of multiple base units and then to the rest of the base units or counter unit, simultaneously to the base and counter units, and the like.

It is to be understood in all of such objectives that the counter units are preferably arranged to not adversely affect other intended operations of the systems. For example, the counter units of the EMC display systems may effectively counter the harmful waves which are irradiated by their wave irradiating base units but may not adversely affect their image generating functions. It is appreciated in all of the objectives that the counter units may be arranged to emit the counter waves defining the phase angles at least partially opposite to those of the harmful waves for the countering in its normal dispositions but that the counter units may emit the counter waves defining the phase angles at least partially similar to those of such harmful waves when disposed on an opposite side of at least one of the base unit with respect to the target space or when the system includes multiple counter units and when it is desirable to modify the radii of curvature of the wavefronts of the counter waves. It is also appreciated that various electric and/or magnetic shields disclosed in the co-pending Applications may be incorporated into any of such EMC display systems either alone or in combination with the counter units to maximally counter the harmful waves.

The basic principle of the counter units of the EMC display systems of the present invention is to emit the counter waves defining the wavefronts similar (or identical) to those of the harmful waves but defining the phase angles at least partially opposite to those of the harmful waves. Therefore, by propagating the counter waves toward the target space, the counter waves may effectively counter the harmful waves in the target space by, e.g., canceling at least a portion of the harmful waves with the counter waves therein, suppressing the harmful waves with the counter waves from propagating theretoward, and the like. To this end, such counter units preferably emit the counter waves defining the wavefronts matching those of the harmful waves by various mechanisms. In one example, such counter units are shaped similar (or identical) to at least one of the base units of the waves sources, or arranged similar (or identical) to the base unit and, accordingly, emit the counter waves capable of countering the harmful waves in the target space. In another example, the counter units are disposed along or across a single or multiple wavefronts of the harmful waves, emit the counter waves similar (or identical) to the harmful waves and, therefore, counter the harmful waves in the target space. In these examples, the counter units emit the counter waves forming the wavefronts similar (or identical) to the shapes of the counter units themselves, and those counter waves define the phase angles at least partially opposite to the phase angles of the harmful waves. In another example, such counter units are shaped differently from at least one of the base units, but rather disposed in an arrangement in which the counter waves emitted thereby match the harmful waves in the target space. In another example, the counter units are disposed across different wavefronts of such harmful waves but emit the counter waves similar (or identical) to the harmful waves, thereby, countering the harmful waves in the target space. In these last two examples, the counter units may be arranged to emit the counter waves defining such wavefronts which may or may not be similar (or identical) to the shapes of the counter units themselves, while the counter waves have the phase angles which are at least partially opposite to those of the harmful waves.

The basic principle of various generic counter units of the EMC display system of the present invention may be implemented to various conventional devices for minimizing irradiation of the harmful waves therefrom. For example, the counter units may be implemented to any base units of electrically conductive wires, coils, and/or sheets of the EMC display system or, alternatively, to any electrically semiconductive and/or insulative wires, coils, and/or sheets of the EMC display system for minimizing the irradiation of the harmful waves by countering the harmful waves by the counter waves, e.g., by canceling at least a portion of the harmful waves in the target space and/or suppressing such harmful waves from propagating to the target space, where the counter units may be made of and/or include at least one electrically conductive, insulative or semiconductive material. Such counter units may be implemented to any of the base units of the shapes which may be formed by including one or multiple wires, coils, and/or sheets, by modifying such shapes of one or multiple wires, coils, and/or sheets, where a few examples of the modified shapes may include a solenoid and toroid each of which may be formed by modifying the shape of the coil. Therefore, such counter units may be implemented into various display units of the EMC systems such as cathode ray tube display units, liquid crystal display units, organic and/or inorganic light emitting display units, plasma display units, and other display units which include multiple pixels and is also capable of emitting visible light rays when supplied with the source electrical energy.

It is appreciated that various counter units of such EMC display systems of this invention may be implemented to any display devices each including at least one of the base units and, accordingly, may irradiate such harmful waves including electric waves (to be abbreviated as "EWs" hereinafter) and magnetic waves (to be abbreviated as "MWs" hereinafter) of frequencies ranging about 50 to 60 Hz and/or other EWs and MWs of higher frequencies. It is appreciated that the EMC display systems of this invention may also be incorporated to any display devices and/or units of portable or stationary electric and/or electronic devices which include at least one base unit examples of which have been provided heretofore. It is further appreciated that the counter units may be provided in a micron-scale and included in semiconductor chips and circuits such as LSI and VLSI devices for such EMC display systems, that the counter units for the EMC display systems may also be formed in a nano-scale and incorporated to various nano devices including at least one base unit which may be a single molecule or a compound, or may be a cluster of multiple molecules or compounds, and so on.

Various system, method, and/or process aspects of such EMC display systems and various embodiments thereof are now enumerated. It is appreciated, however, that following system, method, and/or process aspects of the present invention may be embodied in many other different forms and, accordingly, should not be limited to such aspects and/or their embodiments which are to be set forth herein. Rather, various exemplary aspects and their embodiments described hereinafter are provided such that this disclosure will be thorough and complete, and fully convey the scope of this invention to one of ordinary skill in the relevant art.

In one aspect of the present invention, an EMC display system may include at least one wave source including multiple base units and may be capable of countering harmful electromagnetic waves irradiated by at least one of the base units by canceling such harmful waves in a target space and/or suppressing the harmful waves from propagating toward the target space, where the base units are arranged to include only portions of such wave source responsible for irradiating the harmful waves and/or affecting paths of propagation of the harmful waves therethrough, where the target space is formed between such at least one of base units and an user of the system, and where the system is arranged to include at least one display screen and to display a visual image thereon.

In one exemplary embodiment of this aspect of the invention, an EMC system includes multiple pixels, at least one first electrode, at least one second electrode, at least one controller, and at least one counter unit. Such pixels form the display screen, and each pixel is arranged to generate each portion of the image when supplied with source electrical energy so that such pixels are arranged to generate the image in cooperation, where these pixels are to be referred to as the "standard pixels" hereinafter. The first electrode includes a first plurality of first conductive paths which are provided in a first direction and in a first arrangement in which each pixel is arranged to be electrically coupled to only one of the first paths. Such a first electrode is to be referred to as the "standard first electrode" hereinafter. The second electrode includes a second plurality of second conductive paths which are provided in a second direction and in a second arrangement in which each of the pixels is arranged to electrically couple with only one of the second paths, where this second electrode is to be referred to as the "standard second electrode" hereinafter. The controller is arranged to perform a selection of at least one of the first paths and at least one of the second paths, to supply the source energy only to (or through, across) at least one of the pixels electrically coupling with both of such selected first and second paths for generating only a portion of the image, and to repeat the selection for the rest of the pixels until completing the image, where this controller is to be referred to as the "standard controller" hereinafter. In one example, such a counter unit is arranged to define a configuration at least partially similar to that of at least one of the base units and to emit counter electromagnetic waves as supplied with counter electrical energy in a preset direction. In another example, the counter unit is arranged to have a configuration at least partially similar to that of at least one of the first paths and that of at least one of the second paths and to also emit counter electromagnetic waves when supplied with counter electrical energy in a preset direction. In both of these examples, the counter waves are arranged to have wave characteristics which are at least partially similar to those of the harmful waves irradiated by at least one of the base units due to such a configuration, to have phase angles which are at least partially opposite to those of the harmful waves irradiated by such at least one of the base units due to the preset direction and, therefore, to counter the harmful waves irradiated from such at least one of such base units in the target space, where these counter waves are to be referred to as the "first counter waves" hereinafter.

In another exemplary embodiment of this aspect of the invention, such an EMC system includes multiple standard pixels, at least one standard first electrode, at least one standard second electrode, at least one standard controller, a single counter unit, and the like. In one example, the counter unit is arranged to define a configuration of an 1-D (or 2-D, 3-D) analog of at least one of the base units and to emit the first counter waves when supplied with counter electrical energy in a preset direction. In another example, the counter unit is arranged to have a configuration of an 1-D (or 2-D, 3-D) analog of at least two of the base units and to emit such first counter waves as supplied with counter electrical energy in a preset direction. In another example, the counter unit is arranged to define a configuration of an 1-D (or 2-D, 3-D) analog of at least one of such first paths and at least one of the second paths and to emit the first counter waves when supplied with counter electrical energy in a preset direction.

In another exemplary embodiment of this aspect of the invention, such an EMC system includes multiple standard pixels, at least one standard first electrode, at least one standard second electrode, at least one standard controller, and multiple counter units. In one example, at least two of the counter units are arranged to have a configuration of 1-D (or 2-D, 3-D) analog of at least one of the base units and to emit the first counter waves when supplied with counter electrical energy in a preset direction. In another example, at least two of the counter units are arranged to have configurations of 1-D (or 2-D, 3-D) analogs of at least two of the base units and to emit the first counter waves as supplied with counter electrical energy in a preset direction. In another example, at least one of the counter units is arranged to define configurations of 1-D (or 2-D, 3-D) analogs of at least one of the first paths, and at least another of the counter units is arranged to define configurations of 1-D (or 2-D, 3-D) analog of at least one of the second paths, where the counter units are arranged to emit such first counter waves when supplied with counter electrical energy in a preset direction.

In another aspect of the present invention, another EMC display system may have at least one counter unit and at least one wave source with multiple base units and may be capable of countering harmful electromagnetic waves which are irradiated from at least one of the base units by matching a shape and/or an arrangement of at least one of the base units with a shape and/or an arrangement of the counter unit and by canceling the harmful waves in a target space and/or suppressing the harmful waves from propagating toward the target space, where the base units are arranged to include only portions of the wave source responsible for irradiating such harmful waves and/or affecting paths of propagation of the harmful waves therethrough, where the target space is defined between such at least one of base units and an user of the system, and where the system is also arranged to include at least one display screen and to display a visual image thereon.

In one exemplary embodiment of this aspect of the invention, an EMC system includes multiple standard pixels, at least one standard first electrode, at least one standard second electrode, at least one standard controller, and the counter unit. In one example, the counter unit is arranged to define a shape similar (or identical, conforming) to that of at least one of such base units, and to emit counter electromagnetic waves when supplied with counter electrical energy in a preset direction. In another example, such a counter unit is arranged to define a shape which is similar (or identical, conforming) to that of at least one of the first paths and that of at least one of the second paths, and then to emit counter electromagnetic waves when supplied with counter electrical energy in a preset direction. In both of these example, the counter waves are arranged to define wave characteristics which are at least partially similar to those of the harmful waves irradiated by at least one of the base units due to the shape, to define phase angles at least partially opposite to those of the harmful waves irradiated from such at least one of the base units due to the preset direction and, accordingly, to counter such harmful waves irradiated from such at least one of the base units in the target space. These counter waves are to be referred to as the "second counter waves" hereinafter.

In another exemplary embodiment of this aspect of the invention, such an EMC system includes multiple standard pixels, at least one standard first electrode, at least one standard second electrode, at least one standard controller, and the counter unit. In one example, such a counter unit is arranged to define a shape different from (or not conforming to) that of at least one of the base units, to be in a preset arrangement with respect to the base units, and to emit counter electromagnetic waves when supplied with counter electrical energy in a preset direction. In another example, such a counter unit is arranged to form a shape different from (or not conforming to) that of at least one of the first paths and that of at least one of the second paths, to be in a preset arrangement with respect to such base units, and to emit counter electromagnetic waves when supplied with counter electrical energy along a preset direction. In both example, such counter waves are arranged to have wave characteristics at least partially similar to those of the harmful waves irradiated by at least one of the base units due to the arrangement, to define phase angles at least partially opposite to those of such harmful waves irradiated by such at least one of the base units due to the preset direction and, therefore, to counter the harmful waves irradiated by such at least one of the base units in the target space, where these counter waves are to be referred to as the "third counter waves" hereinafter.

In another exemplary embodiment of this aspect of the invention, such an EMC system includes multiple standard pixels, at least one standard first electrode, at least one standard second electrode, at least one standard controller, and the counter unit. In one example, such a counter unit is arranged to define a shape of an 1-D analog of one of the 1-D (or 2-D, 3-D) base units, and to emit such second counter waves as supplied with counter electrical energy in a preset direction. In another example, the counter unit is arranged to define a shape of at least one 1-D analog of at least two of the 1-D (or 2-D, 3-D) base units and to emit the second counter waves as supplied with counter electrical energy in a preset direction. In another example, the counter unit is arranged to have a shape of a 2-D analog of one of the 1-D (or 2-D, 3-D) base units and to emit the second counter waves when supplied with counter electrical energy along a preset direction. In another example, the counter unit is arranged to have a shape of at least one 2-D analog of at least two of the 1-D (or 2-D, 3-D) base units and to emit the second counter waves as supplied with counter electrical energy in a preset direction. In another example, the counter unit is arranged to have a shape of a 3-D analog of one of the 1-D (or 2-D, 3-D) base units and to emit the second counter waves when supplied with counter electrical energy along a preset direction. In another example, the counter unit is arranged to have a shape of at least one 3-D analog of at least two of the 1-D (or 2-D, 3-D) base units and to emit the second counter waves as supplied with counter electrical energy in a preset direction. In another example, such a counter unit is arranged to have a shape of at least one 1-D (or 2-D, 3-D) analog of at least one of the 1-D (or 2-D, 3-D) first paths and at least one of the 1-D (or 2-D, 3-D) second paths and to emit the second counter waves when supplied with counter electrical energy along a preset direction.

In another exemplary embodiment of this aspect of the invention, such an EMC system includes multiple standard pixels, at least one standard first electrode, at least one standard second electrode, at least one standard controller, and at least one counter unit. In one example, the system includes a single counter unit which is arranged to define a shape matching a shape of one of the base units and to emit the second counter waves when supplied with counter electrical energy in a preset direction. In another example, such a system includes another single counter unit which is arranged to define a shape matching shapes of at least two of the base units and to emit the second counter waves when supplied with counter electrical energy in a preset direction. In another example, the system includes multiple the counter units which are arranged to define an overall shape matching a shape of at least one of the base units, and to emit such second counter waves when supplied with counter electrical energy in a preset direction. In another example, the system includes multiple counter units which are arranged to define an overall shape matching an overall shape of at least two of the base units and to emit the second counter waves when supplied with counter electrical energy in a preset direction. In another example, the system includes multiple counter units at least one of which is arranged to form a shape matching a shape of at least two of the first paths and at least another of which is arranged to define a shape matching a shape of at least two of the second paths, where the counter units are arranged to emit the second counter waves when supplied with counter electrical energy in a preset direction.

In another exemplary embodiment of this aspect of the invention, such an EMC system includes multiple standard pixels, at least one standard first electrode, at least one standard second electrode, at least one standard controller, and at least one counter unit. In one example, the system includes a single counter unit which is arranged to be placed between at least two of such base units and target space, to have a dimension longer than a dimension (or an arrangement) of at least one of such base units, and to emit counter electromagnetic waves when supplied with counter electrical energy along a preset direction. In another example, the system includes a single counter unit which is arranged to be disposed on an opposite side of the target space with respect to at least one of the base units, to define a dimension (or an arrangement) shorter than a dimension of at least one of the base units, and to emit counter electromagnetic waves as supplied with counter electrical energy in a preset direction. In another example, the system includes multiple counter units which are arranged to be incorporated between at least two of the base units and target space, to be in an arrangement having a dimension longer than a dimension (or an arrangement) of at least one of the base units, and then to emit counter electromagnetic waves when supplied with counter electrical energy in a preset direction. In another example, the system includes multiple the counter units which are arranged to be incorporated on an opposite side of the target space relative to at least one of such base units, to be in an arrangement which has a dimension (or an arrangement) shorter than a dimension of at least one of the base units, and to emit counter electromagnetic waves when supplied with counter electrical energy in a preset direction. In all of these examples, such counter waves are arranged to define wave characteristics at least partially similar to those of the harmful waves irradiated by at least one of the base units due to such a dimension, to define phase angles at least partially opposite to those of the harmful waves irradiated by such at least one of the base units due to the preset direction and, therefore, to counter the harmful waves irradiated by such at least one of the base units in the target space.

In another exemplary embodiment of this aspect of the invention, such an EMC system includes multiple standard pixels, at least one standard first electrode, at least one standard second electrode, at least one standard controller, and the counter unit. In one example, the counter unit is arranged to define a shape of a wire, a strip, a tube, a sheet, a coil, a spiral, a mesh thereof, a mixture thereof, a combination thereof, and/or an array thereof while at least partially conforming its shape to a shape of at least one of such base units, and then to emit the second counter waves as supplied with counter electrical energy along a preset direction. In another example, such a counter unit is arranged to have a shape of a wire, a strip, a tube, a sheet, a coil, a spiral, a mesh thereof, a mixture thereof, an array thereof, and/or a combination thereof while at least partially conforming the shape to an arrangement of at least one of the base units, and to emit the second counter waves when supplied with counter electrical energy along a preset direction. In another example, such a counter unit is arranged to have a shape of a wire, a strip, a tube, a sheet, a coil, a spiral, a mesh thereof, a mixture thereof, an array thereof, and/or a combination thereof while at least partially conforming its shape to an arrangement and/or a shape of at least one of the first paths and at least one of the second paths, and to emit the second counter waves when supplied with counter electrical energy in a preset direction.

In another exemplary embodiment of this aspect of the invention, such an EMC system includes multiple standard pixels, at least one standard first electrode, at least one standard second electrode, at least one standard controller, and the counter unit. In one example, the counter unit is arranged to be in an arrangement which is similar to (or different from) an arrangement of at least one of the base units and to emit the third counter waves when supplied with counter electrical energy along a preset direction. In another example, such a counter unit is arranged to be in an arrangement which is similar to (or different from) an arrangement of at least one of such first paths and at least one of the second paths and to emit such third counter waves as supplied with counter electrical energy along a preset direction.

In another exemplary embodiment of this aspect of the invention, such an EMC system includes multiple standard pixels, at least one standard first electrode, at least one standard second electrode, at least one standard controller, and the counter unit. In one example, the counter unit is arranged to be disposed between the target space and at least two of the base units, to define a size larger than a size of each of at least two of such base units, and then to emit counter electromagnetic waves as supplied with counter electrical energy along a preset direction. In another example, the counter unit is arranged to be disposed on an opposite side of the target space with respect to the base units, to have a size which is smaller than a size of each of at least two of the base units, and to emit counter electromagnetic waves when supplied with counter electrical energy in a preset direction. In both of these examples, such counter waves are arranged to have wave characteristics which are at least partially similar to those of the harmful waves irradiated from at least one of the base units due to the size, to have phase angles at least partially opposite to those of the harmful waves irradiated by such at least one of the base units due to the preset direction and, therefore, to counter the harmful waves irradiated by such at least one of the base units in the target space.

In another aspect of the present invention, another EMC display system may have at least one counter unit and at least one wave source with multiple base units and may be capable of countering harmful electromagnetic waves irradiated by at least one of the base units by matching a disposition of at least one of the base units with a disposition of the counter unit and by suppressing the harmful waves from propagating to a target space and/or canceling such harmful waves in the target space, where the base units are arranged to include only those portions of the wave source responsible for irradiating the harmful waves and/or affecting propagation paths of the harmful waves therethrough, where the target space is formed between an user of the system and such at least one of base units, while the system includes at least one display screen for displaying a visual image thereon.

In one exemplary embodiment of this aspect of the invention, an EMC system includes multiple standard pixels, at least one standard first electrode, at least one standard second electrode, at least one standard controller, and the counter unit. In one example, the counter unit is arranged to be in an alignment matching a propagation direction of the harmful waves, a direction of electric current which flows in at least one of such base units, a direction of electric voltage which is applied across at least one of such base units, a direction along a longitudinal axis of at least one of the base units, and/or a direction of a short axis thereof normal to such a longitudinal axis, and to emit counter electromagnetic waves when supplied with counter electrical energy along a preset direction. In another example, the counter unit is arranged to be in an alignment matching a propagation direction of the harmful waves, a direction of electric current flowing through the first and/or second electrodes, a direction of electric voltage applied across the first and/or second electrodes, a direction along a longitudinal axis of such first and/or second paths, and/or a direction of a short axis thereof normal to the longitudinal axis, and to emit counter electromagnetic waves as supplied with counter electrical energy in a preset direction. In both of the examples, the counter waves are arranged to define wave characteristics which are at least partially similar to those of such harmful waves irradiated from at least one of the base units due to such an alignment, to define phase angles at least partially opposite to those of the harmful waves irradiated by such at least one of the base units due to the preset direction and, therefore, to counter the harmful waves irradiated by such at least one of the base units in the target space.

In another exemplary embodiment of this aspect of the invention, such an EMC system includes multiple standard pixels, at least one standard first electrode, at least one standard second electrode, at least one standard controller, and the counter unit. In one example, the counter unit is arranged to be disposed in a position between at least one of the base units and target space and to emit counter electromagnetic waves defining amplitudes less than those of the harmful waves when supplied with counter electrical energy in a preset direction. In another example, the counter unit is arranged to be disposed in a position on an opposite side of the target space with respect to at least one of the base units and then to emit counter electromagnetic waves of amplitudes greater than those of the harmful waves when supplied with counter electrical energy in a preset direction. In both of such examples, the counter waves are arranged to have wave characteristics at least partially similar to those of the harmful waves irradiated by at least one of the base units due to the position, to define phase angles at least partially opposite to those of the harmful waves irradiated from such at least one of the base units due to the preset direction and, accordingly, to counter the harmful waves irradiated by such at least one of the base units in the target space.

In another exemplary embodiment of this aspect of the invention, such an EMC system includes multiple standard pixels, at least one standard first electrode, at least one standard second electrode, at least one standard controller, and the counter unit. In one example, the counter unit is arranged to be in a disposition enclosing therein at least a portion (or an entire portion) of at least one of the base units and to emit counter electromagnetic waves as supplied with counter electrical energy in a preset direction. In another example, the counter unit is arranged to be in a disposition enclosed by at least a (or an entire) portion of at least one of such base units and to emit counter electromagnetic waves as supplied with counter electrical energy along a preset direction. In another example, the counter unit is arranged to be in a disposition lateral (or side by side) with at least one of the base units and to emit counter electromagnetic waves when supplied with counter electrical energy in a preset direction. In another example, such a counter unit is arranged to be in a disposition enclosing therein at least a (or an entire) portion of at least one of such first paths and at least one of such second paths and then to emit counter electromagnetic waves as supplied with counter electrical energy in a preset direction. In all of these examples, the counter waves are arranged to have wave characteristics which are at least partially similar to those of the harmful waves irradiated by at least one of such base units due to the disposition, to define phase angles at least partially opposite to those of the harmful waves which are irradiated from such at least one of the base units due to the preset direction and, accordingly, to counter the harmful waves irradiated by such at least one of the base units in the target space.

In another exemplary embodiment of this aspect of the invention, such an EMC system includes multiple standard pixels, at least one standard first electrode, at least one standard second electrode, at least one standard controller, and the counter unit. In one example, the counter unit is arranged to be in a disposition which is symmetric (or asymmetric) to at least a portion of at least one of the base units and then to emit counter electromagnetic waves when supplied with counter electrical energy in a preset direction. In another example, the counter unit is arranged to be in a disposition symmetric (or asymmetric) to at least portions of at least one of the first paths and at least one of the second paths and to emit counter electromagnetic waves when supplied with counter electrical energy in a preset direction. In both examples, the counter waves are arranged to define wave characteristics at least partially similar to those of the harmful waves irradiated from at least one of the base units due to the disposition, to define phase angles at least partially opposite to those of the harmful waves irradiated from such at least one of the base units due to the preset direction and, accordingly, to counter such harmful waves irradiated by such at least one of the base units in the target space.

In another exemplary embodiment of this aspect of the invention, an EMC system has multiple standard pixels, at least one standard first electrode, at least one standard second electrode, at least one standard controller, and the counter unit which is arranged to be in a stationary disposition with respect to at least one of the base units and to emit counter electromagnetic waves as supplied with counter electrical energy in a preset direction. Whereby such counter waves are arranged to define wave characteristics at least partially similar to those of the harmful waves irradiated by at least one of the base units while maintaining the disposition, to define phase angles at least partially opposite to those of the harmful waves which are irradiated from such at least one of such base units due to the preset direction and, accordingly, to counter the harmful waves irradiated by such at least one of the base units in the target space.

In another exemplary embodiment of this aspect of the invention, an EMC system has multiple standard pixels, at least one standard first electrode, at least one standard second electrode, at least one standard controller, and the counter unit which is arranged to be in a mobile disposition relative to at least one of the base units and to emit counter electromagnetic waves when supplied with counter electrical energy in a preset direction. Whereby, the counter waves are also arranged to have wave characteristics at least partially similar to those of the harmful waves irradiated by at least one of the base units while moving with respect to such at least one of the base units, to define phase angles at least partially opposite to those of the harmful waves irradiated by such at least one of the base units due to the preset direction and, accordingly, to counter the harmful waves irradiated by such at least one of the base units in the target space.

In another aspect of the present invention, another EMC display system may have at least one counter unit and at least one wave source including multiple base units, where the base units irradiate harmful electromagnetic waves which define multiple wavefronts during their propagation, where the counter unit emits counter electromagnetic waves and is also arranged to counter the harmful waves which are irradiated from at least one of such base units by matching at least a portion of at least one of the wavefronts of the harmful waves with the counter waves and by canceling the harmful waves by the counter waves in a target space and/or suppressing the harmful waves by the counter waves from propagating toward the target space, where the base units are arranged to include only portions of the wave source responsible for irradiating the harmful waves and/or affecting propagation paths of the harmful waves therethrough, where such a target space is defined between at least one of the base units and an user of the system, and where the system includes at least one display screen and to display a visual image thereon.

In one exemplary embodiment of this aspect of the invention, such an EMC system includes the multiple standard pixels, at least one standard first electrode, at least one standard second electrode, at least one standard controller, and at least one counter unit. In one example, such a counter unit is arranged to be in a preset arrangement with respect to at least one of the wavefronts of the harmful waves and to emit the counter waves as supplied with counter electrical energy in a preset direction. In another example, the counter unit is arranged to be in a preset arrangement with respect to at least one of the wavefronts of the harmful waves irradiated by at least one of the first paths and at least one of the second paths and to emit the counter waves when supplied with counter electrical energy in a preset direction. In both examples, such counter waves are arranged to match the portion of the wavefront of the harmful waves due to such an arrangement, to define phase angles at least partially opposite to those of the harmful waves due to such a preset direction and, therefore, to counter the harmful waves in the target space, where these counter waves are to be referred to as the "fourth counter waves" hereinafter.

In another exemplary embodiment of this aspect of the invention, such an EMC system includes multiple standard pixels, at least one standard first electrode, at least one standard second electrode, at least one standard controller, and at least one counter unit. In one example, the system includes a single counter unit which is arranged to be disposed in a front arrangement and along the wavefront and to emit the fourth counter waves as supplied with counter electrical energy in a preset direction, where the counter waves define amplitudes less than those of the harmful waves, while the counter unit is disposed between at least two of the base units and the target space in the front arrangement. In another example, the system has multiple counter units each (or at least two) of which is arranged to be disposed in a front arrangement and along the wavefront and to emit the fourth counter waves when supplied with counter electrical energy in a preset direction, where the counter waves define amplitudes less than those of the harmful waves and where the counter units are disposed between at least two of the base units and the target space in the front arrangement.

In another exemplary embodiment of this aspect of the invention, such an EMC system includes multiple standard pixels, at least one standard first electrode, at least one standard second electrode, at least one standard controller, and at least one counter unit. In one example, the system includes a single counter unit which is arranged to be provided in a rear arrangement and then to emit the fourth counter waves when supplied with counter electrical energy in a preset direction, where such fourth counter waves are arranged to have amplitudes greater than those of the harmful waves and where the counter unit is disposed on an opposite side of the target space with respect to at least one of the base units in the rear arrangement. In another example, such a system includes multiple counter units each (or at least two) of which is arranged to be in a rear arrangement and to emit the fourth counter waves when supplied with counter electrical energy in a preset direction, where such fourth counter waves are arranged to have amplitudes greater than those of the harmful waves, while such counter units are disposed on an opposite side of the target space with respect to such base units in the rear arrangement.

In another aspect of the present invention, another EMC display system may have at least one counter unit and at least one wave source including multiple base units, where the base units irradiate harmful electromagnetic waves which define multiple wavefronts during their propagation, where the counter unit emits counter electromagnetic waves and is also arranged to counter the harmful waves which are irradiated by at least one of such base units by matching at least a portion of at least one of the wavefronts of the harmful waves with such counter waves and by canceling the harmful waves by the counter waves in a target space and/or suppressing the harmful waves by the counter waves from propagating toward the target space, where the base units are arranged to include only portions of the wave source responsible for irradiating the harmful waves and/or affecting propagation paths of the harmful waves therethrough, where such a target space is defined between at least one of the base units and an user of the system, and where the system includes at least one display screen and to display a visual image thereon.

In one exemplary embodiment of this aspect of the invention, an EMC system includes multiple standard pixels, at least one standard first electrode, at least one standard second electrode, at least one standard controller, at least one counter unit, and the like. In one example, the system includes a single counter unit which is arranged to be provided closer to the target space with respect to at least one of the base units, to be aligned with the portion of only one (or the portions of at least two) of the wavefronts, and to emit the fourth counter waves when supplied with counter electrical energy along a preset direction. In another example, the system includes a single counter unit which is arranged to be disposed farther away from the target space with respect to at least one of the base units, to be in an arrangement at least partially inverse to the portion of only one (or the portions of at least two) of the wavefronts, and to emit the fourth counter waves when supplied with counter electrical energy in a preset direction. In another example, the system has multiple counter units at least two of which are arranged to be disposed closer to the target space with respect to at least one of such base units, to be aligned with the portion of only one (or the portions of at least two) of the wavefronts, and to emit the fourth counter waves as supplied with counter electrical energy in a preset direction. In another example, the system includes multiple counter units at least two of which are arranged to be disposed farther away from the target space relative to at least one of the base units, to be in an arrangement at least partially inverse to the portion of only one (or the portions of at least two) of the wavefronts, and to emit the fourth counter waves as supplied with counter electrical energy in a preset direction.

In another exemplary embodiment of this aspect of the invention, such an EMC system includes multiple standard pixels, at least one standard first electrode, at least one standard second electrode, at least one standard controller, and at least one counter unit. In one example, the system includes a single counter unit which is arranged to define a dimension larger (or smaller) than a dimension of at least one of the base units, to be disposed between such at least one of such base units and target space in an arrangement which matches the portion of only one (or the portions of at least two) of the wavefronts, and to emit the fourth counter waves when supplied with counter electrical energy in a preset direction. In another example, the system includes multiple counter units at least two of which are arranged to have dimensions larger (or smaller) than a dimension of at least one of the base units, to be disposed between such at least one of such base units and the target space in an arrangement matching the portion of only one (or the portions of at least two) of such wavefronts, and then to emit the fourth counter waves as supplied with counter electrical energy in a preset direction.

In another exemplary embodiment of this aspect of the invention, such an EMC system includes multiple standard pixels, at least one standard first electrode, at least one standard second electrode, at least one standard controller, and at least one counter unit. In one example, the system includes a single counter unit which is arranged to be between at least two of the base units and target space in an arrangement similar (or identical, conforming) to the portion of only one (or the portions of at least two) of the wavefronts, and to emit the fourth counter waves when supplied with counter electrical energy along a preset direction. In another example, the system includes a single counter unit which is arranged to be on an opposite side of the target space with respect to at least one of the base units in an arrangement similar (or identical, conforming) to such a portion of only one (or the portions of at least two) of the wavefronts, and to emit the fourth counter waves as supplied with counter electrical energy in a preset direction. In another example, the system has multiple counter units at least two of which are arranged to be disposed between the target space and at least two of the base units in an arrangement similar (or identical, conforming) to such a portion of only one (or the portions of at least two) of the wavefronts, and to emit the fourth counter waves when supplied with counter electrical energy in a preset direction. In another example, the system includes multiple counter units at least two of which are arranged to be disposed on an opposite side of the target space with respect to at least two of the base units in an arrangement similar (or identical, conforming) to the portion of only one (or the portions of at least two) of the wavefronts, and to emit the fourth counter waves when supplied with counter electrical energy in a preset direction.

In another exemplary embodiment of this aspect of the invention, such an EMC system includes multiple standard pixels, at least one standard first electrode, at least one standard second electrode, at least one standard controller, and at least one counter unit. In one example, such a counter unit is arranged to have a shape similar (or identical, conforming) to that of the portion of at least one of the wavefronts, to be between at least two of the base units and target space in an arrangement which is not similar (or not identical, not conforming) to such at least one of the wavefronts, and to emit the fourth counter waves when supplied with counter electrical energy in a preset direction. In another example, the counter unit is arranged to define a shape similar (or identical, conforming) to that of at least one of the wavefronts, to be incorporated on an opposite side of the target space with respect to at least two of the base units in an arrangement not similar (or not identical, not conforming) to the portion of at least one of the wavefronts, and to emit such fourth counter waves when supplied with counter electrical energy in a preset direction. In another example, such a counter unit is arranged to define a shape not similar (or not identical, not conforming) to that of at least one of the wavefronts, to be disposed between the target space and at least two of the base units in an arrangement not similar (or not identical, not conforming) to the portion of at least one of the wavefronts, and to emit the fourth counter waves as supplied with counter electrical energy in a preset direction. In another example, the counter unit is arranged to define a shape not similar (or not identical, not conforming) to that of at least one of the wavefronts, to be incorporated on an opposite side of the target space with respect to at least two of the base units in an arrangement not similar (or not identical, not conforming) to the portion of at least one of the wavefronts, and then to emit the fourth counter waves as supplied with counter electrical energy in a preset direction.

In another exemplary embodiment of this aspect of the invention, such an EMC system includes multiple standard pixels, at least one standard first electrode, at least one standard second electrode, at least one standard controller, and at least one counter unit. In one example, such a counter unit is arranged to be in an arrangement enclosing the portion of only one (or the portions of at least two) of the wavefronts therein and to emit such fourth counter waves when supplied with counter electrical energy in a preset direction. In another example, the counter unit is arranged to be in an arrangement enclosed by the portion of only one (or the portions of at least two) of the wavefronts and to emit the fourth counter waves when supplied with counter electrical energy in a preset direction. In another example, the counter unit is arranged to be in a lateral (or side-by-side) arrangement to the portion of only one (or the portions of at least two) of the wavefronts and to emit the fourth counter waves as supplied with counter electrical energy in a preset direction.

In another exemplary embodiment of this aspect of the invention, such an EMC system includes multiple standard pixels, at least one standard first electrode, at least one standard second electrode, at least one standard controller, and at least one counter unit. In one example, such a counter unit is arranged to emit such fourth counter waves when supplied with counter electrical energy in a preset direction while being disposed along such a portion of only one (or the portions of at least two) of the wavefronts in an arrangement defining a wire, a strip, a sheet, a tube, a coil, a spiral, a mesh thereof, a mixture thereof, a combination thereof, and/or an array thereof, and disposed between at least one of the base units and target space. In another example, the counter unit is arranged to emit the fourth counter waves as supplied with counter electrical energy in a preset direction while being disposed along such a portion of only one (or the portions of at least two) such wavefronts in an arrangement of a wire, a strip, a sheet, a tube, a coil, a spiral, a mesh thereof, a mixture thereof, an array thereof, and/or a combination thereof and while being disposed on an opposite side of the target space with respect to at least one of the base units.

In another exemplary embodiment of this aspect of the invention, such an EMC system includes multiple standard pixels, at least one standard first electrode, at least one standard second electrode, at least one standard controller, and at least two counter units each of which is arranged to disposed in an arrangement defined on a far side of the target space with respect to at least one of such base units and to emit such fourth counter waves when supplied with counter electrical energy in a preset direction so that a sum of the counter waves individually emitted by the counter units defines multiple wavefronts with greater radii of curvature than radii of curvature of the wavefronts of the individual counter waves.

In another aspect of the present invention, another EMC display system may have at least one counter unit and at least one wave source including multiple base units, where the base units irradiate harmful electromagnetic waves which define multiple wavefronts during their propagation, where the counter unit emits counter electromagnetic waves and is also arranged to counter the harmful waves which are irradiated by at least one of the base units by matching at least a portion of at least one of the wavefronts of the harmful waves with such counter waves and by canceling the harmful waves by the counter waves in a target space and/or suppressing the harmful waves by the counter waves from propagating toward the target space, where the base units are arranged to include only portions of the wave source responsible for irradiating the harmful waves and/or affecting propagation paths of the harmful waves therethrough, where the target space is defined between at least one of such base units and an user of the system, and where the system includes at least one display screen and to display a visual image thereon.

In one exemplary embodiment of this aspect of the invention, an EMC system includes multiple standard pixels, at least one standard first electrode, at least one standard second electrode, at least one standard controller, and at least one counter unit. In one example, a system has a single counter unit which is arranged to define a configuration matching that of only one of the base units and to emit the counter waves when supplied with counter electrical energy along a preset direction. In another example, multiple counter units are arranged to be in an arrangement matching a configuration of only one of the base units and to emit the counter waves when supplied with counter electrical energy in a preset direction. In both examples, such counter waves are arranged to define phase angles which are at least partially opposite to those of the harmful waves, to at least partially match such a portion of the wavefront of the harmful waves due to the configuration and, therefore, to counter the harmful waves in the target space.

In another exemplary embodiment of this aspect of the invention, such an EMC system includes multiple standard pixels, at least one standard first electrode, at least one standard second electrode, at least one standard controller, and at least one counter unit. In one example, the system includes a single counter unit which is arranged to define a configuration matching an arrangement of all (or at least two but not all) of such base units and then to emit the counter waves as supplied with counter electrical energy in a preset direction. In another example, the system includes multiple counter units at least two (or all) of which are arranged to be in an arrangement matching an arrangement of all (or at least two but not all) of the base units and to emit the counter waves when supplied with counter electrical energy in a preset direction. In both examples, such counter waves are arranged to define phase angles at least partially opposite to those of such harmful waves, to at least partially match the portion of the wavefront of the harmful waves due to the arrangement and, therefore, to counter the harmful waves in the target space.

In another exemplary embodiment of this aspect of the invention, such an EMC system includes multiple standard pixels, at least one standard first electrode, at least one standard second electrode, at least one standard controller, and at least one counter unit. In one example, the system includes a single counter unit which is arranged to define a preset shape, to be in a preset arrangement relative to at least one of the base units, and to emit the counter waves when supplied with counter electrical energy in a preset direction, where such a shape and/or arrangement is arranged to match the portion of only one (or the portions of at least two) of such wavefronts. In another example, the system has multiple counter units all (or at least two but not all) of which are arranged to define an overall preset shape, to be in a preset arrangement relative to at least one of the base units, and to emit the counter waves as supplied with counter electrical energy in a preset direction, where the arrangement and/or shape is arranged to match the portion of only one (or the portions of at least two) of the wavefronts. In both examples, the counter waves are arranged to define multiple wavefronts at least one of which is similar (or identical) to the portion of the wavefront of such harmful waves due to the shape and/or arrangement, to also have phase angles at least partially opposite to those of the harmful waves and, accordingly, to counter the harmful waves due to the phase angles in the target space.

In another exemplary embodiment of this aspect of the invention, such an EMC system includes multiple standard pixels, at least one standard first electrode, at least one standard second electrode, at least one standard controller, and at least one counter unit. In one example, the system includes a single counter unit which is shaped, sized, and/or disposed to emit the counter waves when supplied with counter electrical energy in a preset direction, where the counter waves are arranged to match the portion of only one (or the portions of at least two) of the wavefronts of the harmful waves which are irradiated by only one (or at least two) of the base units. In another example, the system includes multiple counter units all (or at least two but not all) of which are disposed, shaped, and sized to emit the counter waves when supplied with counter electrical energy in a preset direction, where a sum of the counter waves is arranged to match the portion of only one (or the portions of at least two) of the wavefronts of the harmful waves irradiated from only one (or at least two) of the base units. In both examples, the counter waves are arranged to define multiple wavefronts at least one of which is at least partially similar to (or identical to) the portion of only one (or the portions of at least two) of the wavefronts of the harmful waves due to at least one of a disposition, shape, and size of the counter unit(s), to have phase angles at least partially opposite to those of the harmful waves and, therefore, to counter the harmful waves in the target space.

In another aspect of the present invention, another EMC display system may have at least one counter unit and at least one wave source including multiple base units, where the base units irradiate harmful electromagnetic waves which define multiple wavefronts during their propagation, where the counter unit emits counter electromagnetic waves and is also arranged to counter the harmful waves which are irradiated by at least one of the base units by matching at least a portion of at least one of the wavefronts of the harmful waves by the counter waves and by suppressing the harmful waves with the counter waves from propagating toward a target space and/or canceling the harmful waves by the counter waves in the target space, where the base units are arranged to include only portions of the wave source responsible for irradiating the harmful waves and/or affecting propagation paths of the harmful waves therethrough, where the target space is defined between at least one of such base units and an user of the system, and where the system includes at least one display screen and to display a visual image thereon.

In one exemplary embodiment of this aspect of the invention, an EMC system includes multiple standard pixels, at least one standard first electrode, at least one standard second electrode, at least one standard controller, and at least one counter unit which is arranged to define a preset shape and a preset size, to be in a preset arrangement aligned with the portion of only one (or the portions of at least two) of the wavefronts, and to emit counter electromagnetic waves when supplied with counter electrical energy along a preset direction, whereby the counter waves are arranged to define phase angles at least partially opposite to those of such harmful waves, to match the portion of only one (or the portions of at least two) of the wavefronts of the harmful waves and, accordingly, to counter the harmful waves in the target space.

In another exemplary embodiment of this aspect of the invention, such an EMC system includes multiple standard pixels, at least one standard first electrode, at least one standard second electrode, at least one standard controller, multiple counter units, and the like. In one example, the counter units are arranged to be in a disposition defined between at least two of the base units and target space, to be in an arrangement which is aligned with the portion of only one (or the portions of at least two) of the wavefronts of the harmful waves and, therefore, to emit the counter waves when supplied with counter electrical energy in a preset direction. In another example, such counter units are arranged to be in a disposition defined on an opposite side of the target space relative to such base units, to be in an arrangement which is at least partially inverse to the portion of only one (or at least two portions of at least two) of the wavefronts of the harmful waves, and to emit the counter waves when supplied with counter electrical energy along a preset direction. In both examples, a sum of the counter waves emitted by at least two of the counter units is arranged to have phase angles at least partially opposite to those of the harmful waves, to match the portion of only one (or the portions of at least two) of the wavefronts of the harmful waves due to such an arrangement and/or disposition and, accordingly, to counter the harmful waves in the target space.

In another aspect of the present invention, an EMC electric display system may include at least one wave source with multiple base units and may be capable of countering harmful electromagnetic waves irradiated by at least one of the base units by canceling such harmful waves in a target space and/or suppressing the harmful waves from propagating to the target space, where such base units are arranged to include only those portions of the wave source responsible for irradiating the harmful waves and/or affecting paths of the harmful waves therethrough, where the target space is defined between at least one of the base units and an user of the system, and where the system is arranged to include at least one display screen and to display a visual image thereon.

In one exemplary embodiment of this aspect of the invention, an EMC system includes at least one light source, multiple pixels, at least one standard first electrode and standard second electrode, at least one standard controller, and at least one counter unit. Such a light source is arranged to emit visible light rays, while the pixels forms the display screen, whereas each of such pixels is arranged to include at least one liquid crystal therein and to generate each portion of the image by manipulating transmission of the light rays through the crystal as supplied with source electrical energy, thereby the pixels generating the image in cooperation. In one example, the counter unit is arranged to define a configuration which is at least partially similar (or identical) to at least one of such base units and to emit such first counter waves when supplied with counter electrical energy. In another example, the counter unit is arranged to define a shape which is at least partially similar (or identical, conforming) to that of at least one of the base units and to emit the second counter waves as supplied with counter electrical energy. In another example, the counter unit is arranged to have a shape different from (or not conforming to) that of at least one of the base units, to be in a preset arrangement with respect to the base units, and to emit the third counter waves when supplied with counter electrical energy. In another example, the counter unit is arranged to be in a preset arrangement with respect to at least one of the wavefronts of the harmful waves and to emit such fourth counter waves as supplied with counter electrical energy. In another example, the counter unit is arranged to define a preset shape and a preset size, where the harmful waves are arranged to define multiple wavefronts, where the counter unit is arranged to be in a preset arrangement aligned with at least a portion of only one (or portions of at least two) of the wavefronts of the harmful waves, and to emit the counter waves as supplied with counter electrical energy, and where the counter waves are arranged to define phase angles at least partially opposite to those of the harmful waves, to match the portion of only one (or the portions of such at least two) of the wavefronts of such harmful waves due ti the arrangement and, accordingly, to counter the harmful waves in the target space. Such counter waves capable of countering the above harmful waves will be referred to as the "fifth counter waves" hereinafter. In another example, the system includes multiple counter units which are arranged to be in a disposition defined between at least two of the base units and the target space, where the harmful waves are arranged to define multiple wavefronts, where the counter unit is arranged to be in an arrangement which is aligned with at least a portion of only one (or portions of at least two) of the wavefronts of the harmful waves and, therefore, to emit the counter waves when supplied with counter electrical energy, while a sum of the counter waves emitted from at least two of the counter units is arranged to have phase angles which are at least partially opposite to those of the harmful waves, to match the portion of only one (or the portions of such at least two) of the wavefronts of the harmful waves due to the disposition and, accordingly, to counter the harmful waves in the target space. These counter waves capable of countering such harmful waves are to be referred to as the "fifth counter waves" hereinafter. In another example, the system includes multiple counter units which are arranged to be in a disposition which is defined on an opposite side of the target space with respect to at least one of the base units, where the harmful waves are arranged to define multiple wavefronts, where such counter units are also arranged to be in an arrangement at least partially inverse to at least a portion of only one (or portions of at least two) of the wavefronts of the harmful waves, and then to emit the counter waves as supplied with counter electrical energy, and where a sum of such counter waves which are emitted by at least two of the counter units is arranged to have phase angles which are at least partially opposite to those of the harmful waves, to match the portion of only one (or the portions of such at least two) of the wavefronts of the harmful waves due to the disposition and, accordingly, to counter the harmful waves in the target space, where these counter waves capable of countering such harmful waves are to be referred to as the "fifth counter waves" hereinafter.

In another exemplary embodiment of this aspect of the present invention, such an EMC system includes multiple pixels, at least one standard first electrode, at least one standard second electrode, at least one standard controller, and at least one counter unit. Such pixels define the display screen, where each pixel is arranged to include therein at least one organic (and/or inorganic) material and to generate each portion of the image by emitting visible light rays with the organic (or inorganic) material when supplied with source electrical energy, whereby such pixels generate the image in cooperation. In one example, the counter unit is arranged to define a configuration which is at least partially similar (or identical) to at least one of the base units and to emit the first counter waves when supplied with counter electrical energy. In another example, the counter unit is arranged to define a shape which is at least partially similar (or identical, conforming) to that of at least one of such base units and to emit the second counter waves when supplied with counter electrical energy. In another example, such a counter unit is arranged to define a shape different from (or not conforming to) that of at least one of the base units, to be in a preset arrangement relative to the base units, and to emit such third counter waves as supplied with counter electrical energy. In another example, the counter unit is arranged to be in a preset arrangement with respect to at least one of the wavefronts of the harmful waves and to emit the fourth counter waves as supplied with counter electrical energy. In another example, the counter unit is arranged to have a preset shape and a preset size and to emit the fifth counter waves. In another example, the system has multiple counter units which are arranged to be in a disposition defined between at least two of the base units and target space and to emit the sixth counter waves. In another example, the system includes multiple counter units which are arranged to be provided in a disposition defined on an opposite side of the target space relative to at least one of such base units and to emit the seventh counter waves.

In another exemplary embodiment of this aspect of the present invention, such an EMC system includes multiple pixels, at least one standard first electrode, at least one second electrode, at least one standard controller, and at least one counter unit. Such pixels form the display screen, and each of the pixels is arranged to include therein at least one phosphor material, to define each portion of the image by emitting visible light rays by the phosphor material as supplied with source electrical energy, thereby the pixels generating the image in cooperation. In one example, the counter unit is arranged to define a configuration at least partially similar (or identical) to at least one of the base units and to emit such first counter waves as supplied with counter electrical energy. In another example, the counter unit is arranged to define a shape at least partially similar (or identical, conforming) to that of at least one of the base units and to emit such second counter waves when supplied with counter electrical energy. In another example, the counter unit is arranged to have a shape which is different from (or not conforming to) that of at least one of the base units, to be in a preset arrangement with respect to the base units, and to emit the third counter waves when supplied with counter electrical energy. In another example, the counter unit is arranged to be in a preset arrangement relative to at least one of the wavefronts of the harmful waves and to emit the fourth counter waves as supplied with counter electrical energy. In another example, the counter unit is arranged to have a preset shape and preset size and to emit the fifth counter waves. In another example, such a system includes multiple counter units which are arranged to be in a disposition defined between at least two of the base units and the target space and to emit such sixth counter waves. In another example, the system includes multiple counter units which are arranged to be in a disposition formed on an opposite side of the target space with respect to at least one of the base units and to emit the seventh counter waves.

In another exemplary embodiment of this aspect of the invention, such an EMC system includes at least one beam generator, multiple pixels, at least one steering unit, a controller, at least one counter unit, and the like. The beam generator is arranged to generate at least one beam of electrons, and the pixels defines the display screen, where each of the pixels is arranged to include therein at least one phosphor material, to generate each portion of the image by emitting visible light rays by the phosphor material when impinged by the beam of electrons so that the pixels generate the image in cooperation. The steering unit is arranged to include at least one but preferably multiple coils, to generate magnetic fields between the beam generator and screen, and to manipulate trajectories of the electron beam by interacting the magnetic fields therewith while serving as the base unit and also irradiating the harmful waves. The controller is arranged to be operatively coupled to the beam generator and steering coils, to adjust the magnetic fields, to perform projection of the electron beam to at least one but not all of the pixels for generating only a portion of the image, and to repeat the projection for the rest of the pixels until completing the image. In one example, such a counter unit is arranged to have a configuration at least partially similar (or identical) to at least one of the base units and to emit the first counter waves as supplied with counter electrical energy. In another example, the counter unit is arranged to define a shape which is at least partially similar (or identical, conforming) to that of at least one of such base units and to emit the second counter waves when supplied with counter electrical energy. In another example, the counter unit is arranged to define a shape different from (or not conforming to) that of at least one of the base units, to be in a preset arrangement with respect to such base units, and to emit the third counter waves as supplied with counter electrical energy. In another example, the counter unit is arranged to be in a preset arrangement with respect to at least one of the wavefronts of such harmful waves and to emit the fourth counter waves when supplied with counter electrical energy. In another example, the counter unit is arranged to define a preset shape and a preset size and to emit the fifth counter waves. In another example, such a system includes multiple counter units which are arranged to be in a disposition defined between at least two of the base units and target space and to emit such sixth counter waves. In another example, the system includes multiple counter units which are arranged to be in a disposition defined on an opposite side of the target space with respect to at least one of the base units and to emit the seventh counter waves.

Embodiments of such system aspects of the present invention may include one or more of the following features, and configurational and/or operational variations and/or modifications of the above systems also fall within the scope of the present invention.

The wave source of the EMC system may include the first electrode, second electrode, beam generator, steering unit, controller, screen, and the like, where the base units of such a wave source and/or EMC system may include the first paths of the first electrode, the second paths of the second electrode, the pixels of the screen, the coils of the steering unit, and various electric and/or electronic elements of the controller, beam generator, and/or the rest of the system, where the components may also include resistors, inductors, capacitors, diodes, signal regulators and/or processors, transistors, amplifiers, and the like. At least one of the base units may be at least one wire and/or strip which may be made of and/or include at least one conductive, semiconductive, and/or insulative material. At least one of the base units may include at least one winding of the wire and/or strip which may be made of and/or include at least one conductive, semiconductive, and/or insulative material.

The system may be an EMC cathode ray tube system, an EMC liquid crystal display system, an EMC organic or inorganic light emitting (diode) system, an EMC plasma display system, an EMC display system emitting visible light rays utilizing the liquid crystal, organic (or inorganic) light emitting material, and/or phosphor material, and the like. The pixels may generate the image by emitting such visible light rays. The system may include at least one light source emitting the visible light rays, where the pixels may generate the image by transmitting the visible light rays therethrough. Such pixels may generate the image when electric current flows therethrough, when electric voltage is applied thereacross, and the like. The source energy may be a source electric current and/or a source electric voltage, and the pixels may serve as the base units irradiating the harmful waves as the source current flows therein or when the source voltage is applied thereacross. The first and second electrodes may be disposed to contact opposite sides of the pixels. The first electrode may be disposed on top of the pixels, while the second electrode may be disposed below bottom of the pixels such that only one of the first paths may contact each of the pixels on its top, while only one of the second paths may contact each of the pixels on its bottom. Such first paths may be arranged parallel to each other in the first direction, such second paths may be arranged parallel to each other in the second direction, and the first and second directions may be transverse (or normal) to each other.

The pixels as well as the electrodes may be grouped into multiple sets. More particularly, the pixels of each set may electrically couple with a corresponding set of the first and second electrodes so that the first and second paths of such electrodes may manipulate the supply of the source energy to those pixels of the specific set of pixels but not to the pixels of the pixels of the rest of the sets. In this embodiment, the controller may also include multiple subcontrollers each of which may manipulate the pixels and conductive paths of the specific set. These sets of pixels and paths may be defined in various patterns, e.g., by dividing the display screen into numerous rectangular or square blocks, by dividing the screen in multiple honeycomb-shaped blocks, by dividing the screen into numerous round polygonal blocks, and the like. As far as numerous pixels of such sets may generate the visual image in cooperation, detailed shapes and/or dividing patterns of the pixels and/or paths may not be material within the scope of the present invention.

The harmful waves may include carrier-frequency waves defining frequencies less than from about 50 Hz to 60 Hz, extremely low-frequency waves of frequencies less than 300 Hz, other waves having frequencies less than 1 kHz, 5 kHz, 10 kHz, 20 kHz, 50 kHz, 100 kHz, 500 kHz, 1 MHz, 10 MHz, 50 MHz, 100 MHz, 500 MHz, 1 GHz, 5 GHz, 10 GHz, 50 GHz, 100 GHz, 500 GHz, 1 THz, 10 THz, and the like, where the counter waves may have frequencies similar to (or greater than, less than) those of the harmful waves. The harmful waves may include ultra low-frequency waves with frequencies less than 3 kHz, very low-frequency waves of frequencies less than 30 kHz, low-frequency waves of frequencies less than 300 kHz, and the like, while the counter waves may have frequencies similar to (or greater than, less than) those of the harmful waves. The target space may be defined on one side of the counter unit and at least one of the base units, around a preset angle around the counter unit or at least one of the base units, between the counter unit and at least one of the base units, and the like.

The above countering may include the canceling and/or the suppressing. The counter unit may receive the counter electrical energy and then actively emit such counter waves or, in the alternative, may not receive the counter electrical energy but rather passively emit the counter waves caused by an electromagnetic induction caused by the magnetic flux of the harmful waves flowing therein. The counter unit may include therein at least one electrically conductive and/or semiconductive material in which the electric current flows or, alternatively, at least one electrically conductive, semiconductive, and/or insulative material across which the electric voltage is applied, and the like. The counter unit may counter the harmful waves by a local countering in which the counter unit may counter only one of the base units or, in the alternative, may counter the harmful waves in a global countering in which the counter unit may counter at least two of the base units. The counter unit may be disposed side by side or stacked with at least one of such base units, may wind around at least one of such base units along a preset length, may concentrically enclose at least one of the base units, may be enclosed in at least one of the base units, and/or may be axially aligned with at least one of the base units. The EMC system may include multiple counter units, where at least one of such counter units may be disposed over the first electrode, and another of the counter units may be disposed under or below the second electrode, thereby countering the first and second electrodes in the local countering. The counter unit may be disposed over both of the first and second electrodes for countering both of the electrodes in the global countering. The counter unit may be spaced from at least one of the base units at a preset distance, may mechanically, electrically, and/or magnetically couple with at least one of the base units, may define an unitary article with at least one of the base units, and the like. The counter unit may be retained by at least one support while maintaining its shape while emitting the harmful waves or, in the alternative, may vary its shape while emitting the counter waves.

The configuration and/or disposition of the counter unit may be determined based on whether the counter unit is to match a configuration of at least one of the base units or to match at least one of the wavefronts of the harmful waves. The counter unit may define the shape identical to, similar to or different from that of at least one of the base units, that of the wave source, and the like. The counter unit may define a shape of the wire, strip, sheet, tube, coil, spiral, mesh, mixture of at least one of the shapes, combination thereof, and/or array thereof, where the array may form a bundle of at least two of the shapes, a braid thereof, a coil thereof, a mesh thereof, and the like. The shape of the counter unit may (or may not) conform to that of at least one of such base units, that of the wave source, and the like. The counter unit may form the 1-D, 2-D, and/or 3-D analogs of at least one of the base units, of the wave source, and the like. A single counter unit may define only one of the analogs or at least two of the analogs or, alternatively, at least two of multiple counter units may define only one of such analogs or at least two of such analogs. The analog may maintain a similarity with at least one of the base units, with the wave source, and the like. At least two of the analogs as a whole may maintain a similarity with at least one of the base units, wave source, and the like. At least two portions of the counter unit and/or at least two counter units may define the same shape of different sizes, different shapes of similar or different sizes, and the like. Such a counter unit may define at least substantially uniform shape and/or size along at least a substantial portion thereof along its longitudinal axis or may have the shape and/or size varying along the portion and/or axis. The size of the counter unit may (or not) conform to that of at least one of the base units, wave source, and the like. Such counter units may be disposed in the arrangement which may be identical to, similar to or different from the shape of at least one of the base units, shape of the wave source, arrangement of at least two of the base units, and/or arrangement of the wave sources. At least two of the counter units may be disposed in an arrangement which may (or not) conform to the shape of at least one of the base units, the shape of the wave source, the arrangement of at least two of such base units, the arrangement of at least two of multiple wave sources, and the like. The counter units may be disposed in a symmetric (or an asymmetric) arrangement with respect to each other, at least one of the base units, the wave source, and the like. The counter unit may be aligned with (or misaligned from) the direction of propagation of the harmful waves, the direction of the electric energy (i.e., current or voltage), the longitudinal axis of at least one of the base units, the short axis of at least one of such base units, one of the axes of the wave source, and the like. All of (or only some of, one of, none of) such counter units may be aligned with (or misaligned from) at least one of the directions and/or axes. The counter unit and at least one of the base units may be disposed at an identical (or similar) distance from the target space. At least a portion of the counter unit and/or at least one of such base units may be disposed in another of the counter and/or base units or, in the alternative, the counter unit and at least one of the base units may be axially disposed along a single common axis of at least two of the counter and/or base units, and the like. The counter units may be in an angular arrangement which is defined around the longitudinal axis of at least one of the base units, wave source, and the like. The counter unit may be movably or stationarily disposed closer to (or farther away from) the target space than at least one of such base units, wave source, and the like. The counter unit and at least one of the base units may be disposed on the same side of the target space or, in the alternative, the counter unit may instead be disposed on opposite sides of the target space. The counter unit may conform to only one of the base units or at least two of the base units or, in the alternative, at least two of such counter units may conform to only one of the base units or at least two of the base units.

A single counter unit may counter the harmful waves irradiated by only one of the first paths, second paths, pixels, electric or electronic components of the system, and the like. A single counter unit may counter the harmful waves irradiated by at least two of the first paths, second paths, pixels, electric or electronic components of the system, and the like. The system may include multiple counter units each of which may counter the harmful waves irradiated by each one of the first paths, second paths, pixels, electric or electronic components of the system, and the like. The system may include multiple counter units at least one of which may counter the harmful waves irradiated by at least two of the first paths, second paths, pixels, electric and/or electronic components of such a system, and the like. The system may include multiple counter units each of which may be disposed closer to each one (or at least two) of the first paths, second paths, pixels, electric and/or electronic components of the system, and the like.

The counter unit may be disposed on an exterior (or interior) of and/or embedded into at least one of the base units, the wave source, and the like. The counter unit may be disposed on, in, and/or inside the screen, a front (or rear) of the screen, a top (or bottom) of the screen, and the like. At least a (or an entire) portion of at least one of the base units may be exposed through the wave source or may be disposed inside the wave source. At least a (or an entire) portion of the counter unit may be exposed through the screen or, alternatively, may instead be disposed inside the screen. The counter unit may be directly coupled to the screen, at least one of the base units, and/or other parts of such a system, may be indirectly coupled thereto through at least one coupler, and the like. The counter unit and at least one of the base units may be made of and/or include therein at least one common material, may be made of or include therein at least one similar materials, may not include any common material, and the like. The counter unit may also be arranged to emit the counter waves using a least amount of material, while consuming a least amount of the current and/or voltage, and the like.

The base units may further be supplied with the source electrical energy (i.e., source electric current and/or source electric voltage, where such source current and/or voltage may be supplied to the counter unit as the counter electrical energy (i.e., counter electric current and/or counter electric voltage), where only a portion of such source current and/or voltage may be supplied to the counter unit as the counter current and/or voltage, where amplitude and/or direction of at least a portion of the source current and/or voltage may be altered and supplied to the counter unit as the counter current and/or voltage, where external current or voltage may be externally provided and synchronized with the source current or voltage and supplied to the counter unit as the counter current or voltage, and the like. The counter unit and at least one of the base units may electrically couple with each other in a series mode, parallel mode or hybrid mode or, alternatively, may not directly couple with each other. The system may include multiple counter units which may be supplied with similar or identical counter currents or voltages, with different counter currents or voltages, and the like. The counter units may be electrically coupled to each other in a series mode, parallel mode or hybrid mode or, alternatively, may not be directly coupled to each other. All (or only some) of the counter units may be electrically coupled to at least one of the base units in the same mode or, in the alternative, none of such counter units may be electrically coupled to at least one of the base units in the same mode.

The counter waves may define amplitudes which are greater than, similar to or less than those of the harmful waves depending upon the disposition thereof with respect to at least one of the base units. The counter unit and at least one of the base units may define substantially identical, similar or different resonance frequencies. At least a portion of a single counter unit and/or at least one of the multiple counter units may define resonance frequencies different from those of the rest thereof.

The system may include at least one of such magnetic shields described hereinabove or in the co-pending Applications. The magnetic shields may be disposed in, on, over, around, and/or through at least one of the counter and/or base units. The magnetic shields may define shapes which may at least partially conform to the shapes of the counter and/or base units or, in the alternative, may define shapes which may be at least partially different from shapes of the counter and/or base units. Such magnetic shield may have at least one path member with a relative magnetic permeability greater than 1,000, 10,000, 100,000, 1,000,000, and the like. The magnetic shield may include at least one magnet member defining at least one South pole. The magnetic shield may include at least one shunt member which may be directly or indirectly coupled to the magnet member. The shunt member may define the relative magnetic permeability which may be greater than 1,000, 10,000, 100,000, 1,000,000, and the like. The magnetic shield described hereinabove or disclosed in the co-pending applications may be incorporated into any of such EMC systems described hereinabove. The system may also include at least one of the electric shields described hereinabove or in the co-pending Applications. The electric shields described hereinabove or disclosed in the co-pending Applications may be incorporated to any of the EMC systems described hereinabove. Such magnetic and/or electric shields may form shapes and/or sizes which may be uniformly maintained along the longitudinal axis of the counter and/or base units or which may vary therealong. The shapes and/or sizes of the magnetic and/or electric shields may be identical to, similar to or different from those of the counter and/or base units. Such a system may also include multiple magnetic and/or electric shields. At least two of the magnetic and/or electric shields may shield against the magnetic waves and/or electric waves of such harmful waves of the same or different frequencies in same or different extents. The magnetic and/or electric shields may be disposed over at least a portion (or entire portion) of the counter and/or base units.

In another aspect of the present invention, a method may be provided so as to counter harmful electromagnetic waves which are irradiated by multiple base units of at least one wave source of an EMC display system by emitting counter electromagnetic waves therefrom, by manipulating shapes of the counter waves, and by suppressing the harmful waves with the counter waves from propagating toward a target space and/or canceling the harmful waves by the counter waves in the target space, where the wave source includes an anode, a cathode, multiple pixels each electrically coupled to the anode and cathode, an electric component of the EMC system, and/or an electronic component of the EMC system, where such base units are arranged to include only portions of the wave source which are responsible for irradiating the harmful waves and/or affecting therethrough paths of propagation of the harmful waves, where the target space is defined between an user of the EMC system and at least one of the base units, where the counter waves define at least one first wavefront during their propagation, where the harmful waves define at least one second wavefront in their propagation, and where the EMC system includes at least one screen which is made up of the pixels and then displays a visual image thereon by manipulating the pixels with the anode and cathode.

In one exemplary embodiment of this aspect of the invention, a method may have the steps of: providing at least one counter unit for emitting such counter waves (the "first providing" hereinafter); extending the counter unit to be wider (or longer) than at least one of the base units of a single wave source; disposing the counter unit between at least one of such base units and user while aligning a width (or length) of the counter unit with at least a portion of the second wavefront; and emitting the counter waves aligned with and at least partially similar to the harmful waves due to such extending and disposing, thereby countering the harmful waves therewith in the target space. Such extending and disposing may be replaced by the steps of: extending the counter unit to be wider (or longer) than at least two of the base units of at least two different wave sources; and disposing the counter unit between at least one of the base units and user while aligning a width (or length) of the counter unit with at least a portion of the second wavefront. Such extending and disposing may also be replaced by the steps of: extending the counter unit to be narrower (or shorter) than at least one of the base units; and disposing the counter unit on an opposite side of the space relative to at least one of such base units while aligning a width (or a length) of the counter unit with at least a portion of the second wavefront.

In another exemplary embodiment of this aspect of the invention, a method may have the steps of: providing a single counter unit for emitting such counter waves; assessing at least one location in the target space where at least a portion of the first wavefront best matches at least a portion of the second wavefront; and disposing the counter unit in the location to emit the counter waves, thereby countering the harmful waves with the counter waves in the target space.

In another exemplary embodiment of this aspect of the invention, a method may have the steps of: providing at least two counter units each capable of emitting the counter waves; emitting from the counter units the counter waves having phase angles similar (or identical) to each other while forming a first sum of the first wavefronts of the counter waves emitted by the counter units; finding a relation between a distance between such counter units and an increase in a radius of curvature of the first wavefront of such a first sum; selecting the distance between the counter units for a preset radius of curvature; assessing at least two locations for the counter units in the target space where at least a portion of the first sum matches at least a portion of the second wavefront; and disposing the counter units in the locations spaced by the distance, thereby countering the harmful waves with the counter waves in the target space. Such emitting and finding may be replaced by the steps of: emitting from the counter units the counter waves having phase angles at least partially opposite to each other and defining a first sum of the first wavefronts of the counter waves emitted from such counter units; and then finding a relation between a distance between such counter units and a decrease in a radius of curvature of the first wavefront of the first sum.

In another aspect of the present invention, a method may be provided so as to counter harmful electromagnetic waves which are irradiated by multiple base units of at least one wave source of an EMC display system by matching at least one feature of at least one of the base units with at least a portion of the system and by suppressing the harmful waves from propagating toward a target space and/or canceling the harmful waves in the target space, where the wave source includes an anode, a cathode, multiple pixels each electrically coupled to the anode and cathode, an electric component of the EMC system, and/or an electronic component of the system, where the base units are arranged to include only those portions of the wave source responsible for irradiating such harmful waves and/or affecting paths of propagation of the harmful waves therethrough, where the target space is defined between at least one of such base units and an user of the system, where the feature is a shape, a size, and/or an arrangement, and where the EMC system includes at least one screen which is made up of the pixels and displays a visual image thereon by manipulating the pixels with both of the anode and cathode.

In one exemplary embodiment of this aspect of the invention, a method may have the steps of: providing at least one counter unit capable of emitting counter electromagnetic waves; configuring the counter unit to match the feature of at least one of such base units of a single wave source; emitting the counter waves similar to the harmful waves due to the configuring; and disposing the counter unit in a location for best matching the harmful waves in the target space with the counter waves, thereby countering the harmful waves with the counter waves therein. Such configuring may be replaced by one of the steps of: configuring the counter unit to match the feature of at least two of the base units of at least two different wave sources; configuring the counter unit to define a configuration which is simpler than that of at least one of such base units of a single wave source while keeping the feature; configuring the counter unit to define a configuration simpler than that of at least two of the base units of at least two different wave sources while maintaining the feature; configuring the counter unit to define a configuration more complex than that of at least one of the base units while at least minimally maintaining the feature; configuring the counter unit to have a dimension defined by a less number of unit axes than at least one of such base units while at least minimally keeping the feature; configuring the counter unit to have a dimension which is defined by a greater number of unit axes than that of at least one of the base units while at least minimally maintaining the feature, and the like.

In another exemplary embodiment of this aspect of the invention, a method may have the steps of: providing a single counter unit capable of emitting counter electromagnetic waves; configuring the counter unit to define a configuration simpler than that of only one of the base units while maintaining the feature; emitting the counter waves which are similar to the harmful waves due to the configuring; and disposing the counter unit in a location for best matching such harmful waves in the target space with the counter waves, thereby countering the harmful waves with the counter waves therein. The above configuring may also be replaced by one of the steps of: configuring the counter unit to have a configuration simpler than that of at least two of the base units of at least two different wave sources while maintaining the feature; configuring the counter unit to define a configuration similar (or identical) to an arrangement of all (or at least two but not all) of such base units of a single wave source while keeping the feature; configuring the counter unit to have a configuration which is similar (or identical) to an arrangement of all (or at least two but not all) of such base units of at least two different wave sources while keeping the feature; configuring the counter unit to be formed in a dimension which is defined by a less number of mutually orthogonal unit axes than an arrangement of all (or at least two but not all) of the base units while maintaining the feature; configuring the counter unit to be formed in a dimension defined by a greater number of mutually orthogonal unit axes than an arrangement of all (or at least two but not all) of the base units while maintaining the feature, and the like.

In another exemplary embodiment of this aspect of the invention, a method may have the steps of: providing multiple counter units each capable of emitting counter electromagnetic waves; arranging at least two of the counter units in a configuration simpler than that of only one of the base units while maintaining the feature; emitting the counter waves similar to the harmful waves due to the arranging; and disposing such counter units in locations for matching the harmful waves in the target space with the counter waves, thereby countering the harmful waves by the counter waves therein. The above arranging may also be replaced by one of the steps of: arranging at least two of the counter units in a configuration simpler than that of at least two of the base units of at least two different wave sources while maintaining the feature; arranging at least two of such counter units in a configuration which is similar (or identical) to an arrangement of all (or at least two but not all) of such base units of a single wave source while keeping the feature; arranging at least two of the counter units in a configuration which is similar (or identical) to an arrangement of all (or at least two but not all) of such base units of at least two different wave sources while maintaining the feature; arranging the counter units in an arrangement defining a dimension which is formed by a less number of mutually orthogonal unit axes than an arrangement of at least one of the base units while maintaining the feature; and arranging the counter units in an arrangement with a dimension formed by a greater number of mutually orthogonal unit axes than an arrangement of at least one of the base units while maintaining the feature.

In another exemplary embodiment of this aspect of the invention, such a method may have the steps of: providing a smaller number of the counter units than the base units of a single wave source; arranging such counter units while approximating an arrangement of all (or at least two but not all) of the base units and while maintaining the feature; emitting the counter waves which are similar to the harmful waves due to the arranging; and then disposing the counter unit in a location for matching the harmful waves in the target space with the counter waves, thereby countering the harmful waves by the counter waves therein. Such providing and arranging may be replaced by the steps of: providing a smaller number of the counter units than the base units of at least two different wave sources; and arranging such counter units while approximating an arrangement of all (or at least two but not all) of the base units and while maintaining the feature. Such providing and arranging may also be replaced by the steps of: providing a greater number of the counter units than the base units of a single wave source; and arranging the counter units while disposing at least two of such counter units around at least one of the base units and while maintaining the feature. Such providing and arranging may also be replaced by the steps of: providing a greater number of the counter units than the base units of at least two different wave sources; and arranging the counter units while disposing at least two of the counter units around at least one of the base units and while maintaining the feature.

In another exemplary embodiment of this aspect of the invention, a method may have the steps of: providing at least one counter unit capable of emitting counter electromagnetic waves; configuring the counter unit to move with respect to at least one of the base units; emitting such counter waves by the counter unit; finding a relation between a distance between the counter unit and at least one of the base units and matching between the counter and harmful waves; assessing a location in which the counter waves best match the harmful waves; and then moving the counter unit to the location to match the harmful waves in the target space with the counter waves, thereby countering the harmful waves by the counter waves therein.

In another aspect of the present invention, a method may be provided so as to counter harmful electromagnetic waves which are irradiated by multiple base units of at least one wave source of an EMC display system by emitting therefrom counter electromagnetic waves and matching such harmful waves therewith and by suppressing the harmful waves by the counter waves from propagating to a target space and/or canceling the harmful waves with the counter waves in the target space, where the wave source includes an anode, a cathode, multiple pixels each of which is electrically coupled to the cathode and anode, an electric component of the EMC system, and/or an electronic component of the system, where the base units are arranged to represent only portions of the wave source which are responsible for irradiating the harmful waves and/or affecting paths of propagation of the harmful waves therethrough, where the target space is defined between an user of the system and at least one of the base units, where the counter waves are arranged to define at least one first wavefront during their propagation, where the harmful waves define at least one second wavefront during their propagation, and where the EMC system includes at least one screen which is made up of the pixels and also displays a visual image thereon by manipulating the pixels with the cathode and anode.

In one exemplary embodiment of this aspect of the invention, a method may have the steps of: the first providing; disposing the counter unit along at least a portion of the second wavefront of such harmful waves irradiated from only one of the base units; and then emitting the counter waves while matching at least a portion of the second wavefront with at least a portion of the first wavefront in the target space due to such disposing, thereby countering the harmful waves with such counter waves therein. Such disposing may be replaced by one of the steps of: disposing the counter unit along at least a portion of the second wavefront of the harmful waves irradiated by all (or at least two but not all) of such base units; disposing the counter unit along at least a portion of the second wavefront of the harmful waves irradiated by at least one of the base units of a single wave source; and disposing the counter unit along at least a portion of the second wavefront of the harmful waves irradiated by at least two of the base units of at least two different wave sources.

In another exemplary embodiment of this aspect of the invention, a method may have the steps of: the first providing; configuring the counter unit to match a shape and/or arrangement thereof with a shape and/or arrangement of the first wavefront; disposing the counter unit along (or across) at least a portion of the second wavefront; and emitting such counter waves while matching at least a portion of the second wavefront with at least a portion of the first wavefront in the target space due to such configuring and disposing, thereby countering the harmful waves by the counter waves therein. The above configuring and disposing may also be replaced by the steps of: configuring the counter unit to define a shape and/or arrangement at least partially different from (or not conforming to) at least one of a shape and an arrangement of the first wavefront; and then disposing the counter unit across (or along) at least two different and spaced apart portions of the second wavefront.

In another exemplary embodiment of this aspect of the invention, a method may have the steps of: the first providing; disposing multiple counter units in an arrangement along at least a portion of the second wavefront; configuring the counter units to match its arrangement with an arrangement of the first wavefront; and then emitting such counter waves while aligning at least a portion of the second wavefront with at least a portion of the first wavefront in the target space due to such disposing and configuring, thereby countering the harmful waves by the counter waves therein. The disposing and configuring may also be replaced by the steps of: disposing multiple counter units in an arrangement across (or along) at least two different portions of the second wavefront; and configuring the counter units to mismatch the arrangement thereof with an arrangement of the first wavefront.

In another exemplary embodiment of this aspect of the invention, a method may have the steps of: the first providing; placing the counter unit between the target space and at least one of such base units; comparing a shorter radius of curvature of the first wavefront to a longer radius of curvature of the second wavefront; and then disposing the counter unit in a location of the target space where the radii of curvature of the first and second wavefronts best match each other, thereby countering such harmful waves with the counter waves therein. Such placing and comparing may be replaced by the steps of: placing the counter unit on an opposite side of the target space with respect to at least one of the base units; and then comparing a longer radius of curvature of the first wavefront to a shorter radius of curvature of the second wavefront.

In another exemplary embodiment of this aspect of the invention, a method may have the steps of: the first providing; configuring the counter unit to move relative to at least one of such base units; finding a relation between a distance between the counter unit and at least one of the base units and matching between radii of curvature of the first and second wavefronts; assessing a location where the first and second wavefronts match each other; and then moving the counter unit to the location for matching the harmful waves in the target space with the counter waves, thereby countering such harmful waves with the counter waves therein.

In another aspect of the present invention, a method may be provided so as to counter harmful electromagnetic waves which are irradiated by multiple base units of at least one wave source of an EMC display system by emitting counter electromagnetic waves from at least one counter unit of such a system and propagating the counter waves in a preset direction toward the harmful waves, where the wave source includes an anode, a cathode, multiple pixels each electrically coupled to the anode and cathode, an electric component of the system, and/or an electronic component of thereof, where the base units are arranged to include only portions of the wave source responsible for irradiating the harmful waves and/or affecting propagation paths of the harmful waves therethrough, where such a target space is defined between an user of the system and at least one of the base units, and where the system includes at least one screen made up of the pixels and displays a visual image thereon by manipulating the pixels with the anode and cathode.

In one exemplary embodiment of this aspect of the invention, a method may have the steps of: configuring the counter waves to define shapes similar to those of the harmful waves and to have at least partially opposite phase angles (the "first configuring" hereinafter); enclosing at least a portion of at least one of the base units by (or in) at least a portion of the counter unit; and emitting such counter waves while enclosing the harmful waves in the target space, thereby countering the harmful waves with the counter waves therein. The above enclosing may also be replaced by the step of: disposing multiple counter units around at least one of the base units.

In another exemplary embodiment of this aspect of the invention, a method may have the steps of: the first configuring; disposing at least a portion of the counter unit inside at least one of such base units; and emitting the counter waves while being enclosed by the harmful waves in the target space, thereby countering the harmful waves by the counter waves therein. The disposing may be replaced by the step of: enclosing at least a portion of the counter unit by at least two of the base units.

In another exemplary embodiment of this aspect of the invention, a method may have the steps of: the first configuring; disposing the counter unit lateral to at least one of the base units; and emitting the counter waves to the target space along with the harmful waves, thereby countering the harmful waves with the counter waves therein. Such disposing may also be replaced by one of the steps of: disposing the counter unit along a longitudinal axis of at least one of such base units and also away therefrom; and enclosing at least a portion of one of the counter unit and at least one of the base units by another of the units.

In another exemplary embodiment of this aspect of the invention, a method may have the steps of: the first configuring; aligning the counter unit in a direction of propagation of such harmful waves; and emitting the counter waves to the target space along with the harmful waves, thereby countering the harmful waves by the counter waves therein. Such aligning may be replaced by one of the steps of: aligning the counter unit along a direction of electric current and/or voltage applied to at least one of the base units; aligning the counter unit with a longitudinal axis of at least one of the base units; and aligning the counter unit with a short axis of at least one of the base units.

In another exemplary embodiment of this aspect of the invention, a method may have the steps of: the first configuring; disposing the counter unit between at least one of such base units and target space; emitting by the counter unit the counter waves with amplitudes less than those of the harmful waves; and propagating the counter waves toward the target space along with the harmful waves, thereby countering the harmful waves with the counter waves therein. Such disposing and emitting may be replaced by the steps of: disposing the counter unit on an opposite side of the target space with respect to at least one of the base units; and emitting by the counter unit with the counter waves defining amplitudes greater than those of the harmful waves.

In another exemplary embodiment of this aspect of the invention, a method may have the steps of: the first configuring; disposing the counter unit between at least one of such base units and target space; extending the counter unit to a width greater than that of at least one of the base units along a direction normal to a direction of propagation of the harmful waves; and emitting such counter waves toward the target space along with the harmful waves, thereby countering the harmful waves by the counter waves therein. Such disposing and extending may be replaced by the steps of: disposing the counter unit on an opposite side of the target space with respect to at least one of the base units; and extending the counter unit to a width less than that of at least one of such base units along a direction normal to a direction of propagation of the harmful waves.

In another aspect of the present invention, a method may be provided so as to counter harmful electromagnetic waves which are irradiated by multiple base units of at least one wave source of an EMC display system by emitting counter electromagnetic waves and by canceling the harmful waves by the counter waves in a target space and/or suppressing the harmful waves by the counter waves from propagating to the target space, where the wave source includes an anode, a cathode, multiple pixels each of which is electrically coupled to both of the anode and cathode, an electric component of the EMC system, and/or an electronic component of the system, where the base units are arranged to include only portions of the wave source which a responsible for irradiating such harmful waves and/or affecting propagation paths of the harmful waves therethrough, where such a target space is defined between an user of the system and at least one of the base units, and where such a system includes at least one screen which is made up of the pixels and also displays a visual image thereon by manipulating the pixels with the anode and cathode.

In one exemplary embodiment of this aspect of the invention, a method may have the steps of: providing a single counter unit for emitting the counter waves; the first configuring; and countering the harmful waves which are irradiated from only one of the base units by the counter waves.

In another exemplary embodiment of this aspect of the invention, a method may have the steps of: providing a single counter unit for emitting the counter waves; the first configuring; and countering a sum of the harmful waves irradiated from all (or at least two but not all) of the base units of a single wave source with the counter waves. Such countering may be replaced by the step of: countering a sum of the harmful waves irradiated by all (or at least two but not all) of the base units of at least two different wave sources with the counter waves.

In another exemplary embodiment of this aspect of the invention, a method may have the steps of: providing multiple counter units for emitting the counter waves; the first configuring; and countering the harmful waves which are irradiated from only one of the base units by a sum of all of the counter waves emitted by all of the counter units.

In another exemplary embodiment of this aspect of the invention, a method may have the steps of: providing multiple counter units for emitting the counter waves the first configuring; and countering a sum of the harmful waves irradiated from all (or at least two but not all) of the base units of a single wave source with a sum of the counter waves emitted from at least two of such counter units. Such countering may be replaced by the step of: countering a sum of the harmful waves irradiated from all (or at least two but not all) of the base units of at least two different wave sources with a sum of the counter waves emitted from at least two of the counter units.

In another exemplary embodiment of this aspect of the invention, a method may have the steps of: providing at least two counter units for emitting the counter waves; configuring at least one of the counter units to move with respect to the other thereof; the first configuring; and moving such at least one of the counter units relative to at least one of the base units in the emitting, thereby countering the harmful waves irradiated by only one of the base units by the counter waves emitted from a different number of the counter units.

In another aspect of the present invention, a method may be provided so as to counter harmful electromagnetic waves which are irradiated by multiple base units of at least one wave source of an EMC display system by emitting counter electromagnetic waves toward such harmful waves, where the wave source includes an anode, a cathode, multiple pixels each of which electrically couples with the anode and cathode, an electric component of the EMC system, and/or an electronic component of the EMC system, where the base unit is arranged to be shaped as at least one curvilinear wire which is a part of a network of multiple wires, and where the system includes at least one screen made up of the pixels at least one of which electrically couples with the wire and then displays a visual image thereon by manipulating the wire.

In one exemplary embodiment of this aspect of the invention, a method may have the steps of: the first providing; shaping the counter unit into a wire, strip, and/or sheet; disposing the counter unit along and close to the wire; and supplying electric energy to the base unit of the wire and counter unit in opposite directions while emitting the counter waves by the counter unit for countering the harmful waves by the counter waves (the "first supplying" hereinafter). Such disposing may be replaced by the step of: braiding the counter unit around and close to the wire.

In another exemplary embodiment of this aspect of the invention, a method may have the steps of: providing multiple counter units each of which is shaped as a wire, strip, and/or sheet; disposing the counter units around and also close to the wire; and the first supplying. The above disposing may be also replaced by the step of: braiding each of the counter units around and close to the wire in the same or different directions.

In another exemplary embodiment of this aspect of the invention, a method may have the steps of: the first providing; shaping the counter unit into at least one coil and/or spiral; winding the counter unit around the wire; and the first supplying. Such shaping and winding may be replaced by the steps of: shaping the counter unit into a sheet and/or a mesh; and winding the counter unit around the wire. Such shaping and winding may instead be replaced by the steps of: shaping the counter unit into an annular tube with a lumen; and disposing the wire inside the lumen of the counter unit.

In another exemplary embodiment of this aspect of the invention, a method may have the steps of: identifying multiple wavefronts of such harmful waves defined around the wire; disposing at least one counter unit along at least one of the wavefronts; and emitting by such a counter unit the counter waves of multiple wavefronts similar (or identical) to the wavefronts of the wire, thereby countering the harmful waves with the counter waves.

In another aspect of the present invention, a method may be provided so as to counter harmful electromagnetic waves which are irradiated by multiple base units of at least one wave source of an EMC display system by emitting counter electromagnetic waves toward such harmful waves, where the wave source includes an anode, a cathode, multiple pixels each of which electrically couples with the anode and cathode, an electric component of the EMC system, and/or an electronic component of the EMC system, where the base unit is arranged to be shaped into at least one curvilinear strip which is included in a network of multiple the strips, and where the EMC system includes at least one screen made up of the pixels at least one of which electrically couples with such a strip and displays a visual image thereon by manipulating strip wire.

In one exemplary embodiment of this aspect of the invention, a method may have the steps of: the first providing; shaping the counter unit as a wire, a strip, and/or a sheet; and supplying electric energy to the base unit of the strip (or sheet) and counter unit in opposite directions while emitting the counter waves by the counter unit in order to counter the harmful waves by the counter waves (the "second supplying" hereinafter). Such shaping may be replaced by one of the steps of: disposing the counter unit along and close to the strip (or sheet); and braiding the counter unit around and close to the strip (or sheet).

In another exemplary embodiment of this aspect of the invention, a method may have the steps of: providing multiple counter units each of which is shaped into a wire, strip, and/or sheet; disposing the counter units around and close to the strip (or sheet); and the second supplying. Such disposing may be replaced by the step of: braiding each counter unit around and close to the strip (or sheet) in one of same and different directions.

In another exemplary embodiment of this aspect of the invention, a method may have the steps of: the first providing; shaping the counter unit into at least one coil and/or spiral; winding the counter unit around the strip (or sheet); and the second supplying. The shaping and winding may be replaced by the steps of: shaping the counter unit into a sheet and/or a mesh; and winding such a counter unit around the strip (or sheet). Such shaping and winding may be replaced by the steps of: shaping the counter unit as a pair of strips (or sheets); and disposing the wire between the strips (or sheets).

In another exemplary embodiment of this aspect of the invention, a method may have the steps of: identifying multiple wavefronts of the harmful waves around the strip (or sheet); disposing at least one counter unit along at least one of the wavefronts; and emitting from the counter unit such counter waves of multiple wavefronts similar (or identical) to such wavefronts of the strip (or sheet), thereby countering the harmful waves with the counter waves.

In another aspect of the present invention, a method may be provided so as to counter harmful electromagnetic waves which are irradiated by multiple base units of at least one wave source of an EMC display system by emitting counter electromagnetic waves toward such harmful waves, where the wave source includes an anode, a cathode, multiple pixels each of which is electrically coupled to the anode and cathode, an electric component of the EMC system, and/or an electronic component of the EMC system, where the base unit is arranged to be shaped as at least one curvilinear coil included in a network of at least two coils, and where the EMC system includes at least one screen made up of such pixels at least one of which is electrically coupled to the coil and displays a visual image thereon by manipulating the coil.

In one exemplary embodiment of this aspect of the invention, a method may have the steps of: the first providing; shaping the counter unit as a toroid by disposing opposing ends of the coil close to each other; supplying the electric energy in the coil; and supplying electric energy to the wave source of the coil and counter unit in opposite directions while emitting the counter waves by the counter unit for countering the harmful waves by the counter waves.

In another exemplary embodiment of this aspect of the invention, a method may have the steps of: the first providing; shaping the counter unit as a wire, a strip, and/or a spiral which is smaller than the coil of the base unit; winding the coil of the base unit around the counter unit; and then the fourth supplying. Such shaping and winding may be replaced by the steps of: shaping the counter unit as another coil smaller than the coil of the base unit; and then winding the coil of the base unit around the counter unit.

In another exemplary embodiment of this aspect of the invention, a method may have the steps of: the first providing; shaping the counter unit as another coil; disposing the coils of the counter and base units adjacent to each other; and the fourth supplying. Such disposing may be replaced by the step of: braiding the coils of the counter and base units.

In another exemplary embodiment of this aspect of the invention, a method may have the steps of: identifying multiple wavefronts of the harmful waves formed around the coil; disposing at least one counter unit along at least one of the wavefronts; and emitting by the counter unit the counter waves of multiple wavefronts which are similar or identical to the wavefronts of the tube, thereby countering the harmful waves with the counter waves.

Embodiments of such method aspects of the present invention may include one or more of the following features, and configurational and/or operational variations and/or modifications of the above methods also fall within the scope of the present invention.

Such countering may include the step of: suppressing and/or canceling the harmful waves by the counter waves while minimizing adverse effects from the countering upon actuating operations of the actuator of the system. Such countering may include one of the steps of: countering the harmful waves irradiated by the base units of only one of such wave sources; countering the harmful waves irradiated by the base units of at least two but not all of the wave sources; and countering the harmful waves irradiated by the base units of all of the wave sources. Such countering may include at least one of the steps of: suppressing at least a portion of the harmful waves from propagating toward the target space with the counter waves; and canceling the portion of the harmful waves by the counter waves in the target space.

The countering may also include at least one of the steps of: countering the harmful waves of frequencies less than about 50 Hz to 60 Hz; countering the harmful waves of frequencies less than about 300 Hz; countering the harmful waves of frequencies less than about 1 kHz, and the like. The countering may include at least one of the steps of: countering the harmful waves of frequencies less than about 10 kHz; countering the harmful waves of frequencies less than about 100 kHz; countering the harmful waves having frequencies less than about 1 MHz, 10 MHz, 100 MHz, 1 GHz, 10 GHz, 100 GHz, 1 THz, and the like. The countering may also include at least one of the steps of: countering the harmful waves in only a portion of one of such frequency ranges while preserving the rest thereof; countering magnetic waves of the harmful waves; and/or countering an entire portion of the harmful waves. The affecting may include at least one of the steps of: including a permanent magnet and/or a highly magnetically permeable material; applying the electric voltage; and flowing the electric current.

Such extending may include one of the steps of: lengthening the counter unit along its length; widening the counter unit along its width, and the like. The providing may include at least one of the steps of: forming the counter unit into a shape of a wire, a strip, a sheet, a tube, a coil, a spiral, and a mesh; forming the counter unit into one of a mixture of the shapes, a combination of the shapes, and an array of the shapes, and the like. The forming may include at least one of the steps of: enclosing at least a portion of at least one of the base units with an array (or a bundle) of multiple wires of the counter unit; enclosing the portion of at least one of the base units by an array (or bundle) of multiple strips of the counter unit; enclosing therein the portion of at least one of the base units by an array (or bundle) of multiple sheets of the counter unit; enclosing the portion of at least one of the base units by an array (or bundle) of multiple tubes of the counter unit; winding with at least one coil of the counter unit about the portion of at least one of the base units; winding the portion of at least one of the base units by an array (or bundle) of multiple coils; enclosing the portion of at least one of the base units by at least one annular mesh of the counter unit, and the like. The forming the counter unit may include at least one of the steps of: extending a single wire for at least a portion of the counter unit; extending an array (or bundle) of multiple wires for the portion; extending a single strip for the portion; extending an array (or bundle) of multiple strips for the portion; extending a single sheet therefor; extending an array (or bundle) of multiple sheets for such a portion; extending a single tube therefor; extending a bundle (or array) of multiple tubes therefor; winding a single coil therefor; winding a bundle (or array) of multiple coils therefor; extending a single annular mesh therefor; and extending an array (or bundle) of multiple annular meshes therefor.

The providing may include one of the steps of: exposing the counter unit through the base unit; hiding the counter unit under (or inside) the base unit, and the like. The providing may include at least one of the steps of: fixedly disposing the counter unit; movably disposing the counter unit, and so on. The providing may include one of the steps of: forming the base and counter units of a same material; forming the base and counter units of different materials; including at least one but not all of materials in the base and counter units, and the like. The providing may include one of the steps of: arranging the base and counter units to have similar (or identical) resonance frequencies; arranging the base and counter units to define different resonance frequencies, and the like.

The disposing may include at least one of the steps of: disposing the counter unit laterally (or side by side) with at least one of the base units; enclosing at least one of the counter and base units with another of the units; axially aligning the base and counter units, and the like. Such enclosing may include one of the steps of: disposing the counter unit indirectly over (or around) at least one of such base units; disposing the counter unit directly on and/or around at least one of the base units, and the like. The enclosing may include at least one of the steps of: arranging at least two of the counter units concentrically; electrically coupling the counter units in one of a series mode, a parallel mode, a hybrid mode, and the like. The aligning may also include one of the steps of: aligning the counter unit with the longitudinal axis of at least one of the base units; aligning such a counter unit with the short axis of at least one of such base units; aligning the counter unit along the direction of the current flowing in (or voltage applied across) at least one of the base units, aligning such a counter unit with the direction of propagation of the harmful waves, and the like.

The configuring the counter unit may include at least one of the steps of: controlling a shape of the counter unit; controlling a size thereof; and controlling an arrangement thereof. The defining such a second wavefront may also include at least one of the steps of: forming the second wavefront with the harmful waves irradiated from only one of the base units; forming the second wavefront with the harmful waves irradiated from at least two but not all of the base units; forming the second wavefront with the harmful waves irradiated from all of the base units, and the like. The defining such a second wavefront may also have at least one of the steps of: forming the second wavefront with the harmful waves irradiated from only one of the wave sources; forming the second wavefront with the harmful waves irradiated from at least two but not all of such wave sources; forming the second wavefront with the harmful waves irradiated from all of the wave sources, and the like. Such configuring and/or arranging may be performed to the harmful waves irradiated by only one of the base units, by at least two but not all of the base units, and/or by all of the base units. The configuring and/or arranging may be performed to the harmful waves irradiated by only one of the wave sources, irradiated by at least two but not all of the wave sources, irradiated by all of the wave sources, and the like.

The disposing may include at least one of the steps of: controlling an orientation of the counter unit with respect to at least one of the base units (or target space); controlling an alignment of such a counter unit with respect thereto; controlling a first distance between the counter unit and base unit (or target space); and controlling a second distance between the counter units. Such disposing may be performed to the harmful waves irradiated from only one of the base units, irradiated from at least two but not all of the base units, irradiated by all of the base units, and the like. The disposing may be performed to the harmful waves irradiated from only one of the wave sources, irradiated from at least two but not all of the wave sources, irradiated from all of the wave sources, and the like.

The emitting may also include one of the steps of: manipulating the phase angles of the counter waves to be at least similar (or identical) to those of the harmful waves when the counter and harmful waves propagate in at least partially opposite directions; manipulating the phase angles of the counter waves to be at least opposite to those of such harmful waves when the counter and harmful waves propagate along at least similar directions; and manipulating the phase angles of the counter waves to be transverse to those of the harmful waves when the counter and harmful waves propagate along directions which may be transverse to each other. The emitting may include at least one of the steps of: controlling amplitudes of the counter waves to be greater or less than those of the harmful waves when measured in the target space; manipulating such amplitudes of the counter waves to be similar or identical to those of the harmful waves when measured at the base unit, and the like. The emitting may include at least one of the steps of: propagating the counter waves in the same direction as that of the harmful waves; propagating the counter waves in a direction different from that of the harmful waves irradiated by each of base units but along the same direction as that of a sum of such harmful waves from the base units, and so on. The emitting may include the step of: controlling phase angles of the counter waves to be at least partially (or substantially) opposite to those of the harmful waves.

Such matching may include one of the steps of: matching the counter waves with the harmful waves irradiated by only one of the base units; matching the counter waves with the harmful waves irradiated by at least two but not all of such base units; matching the counter waves with the harmful waves irradiated by all of the base units, and the like. Such matching may include one of the steps of: matching the counter waves with the harmful waves irradiated from only one of such wave sources; matching the counter waves with the harmful waves irradiated by at least two but not all of the wave sources; and matching the counter waves with the harmful waves irradiated by all wave sources.

The method may also include one of the steps of: flowing the current in an entire portion of the base unit; flowing the current in only a portion of the base unit; applying the voltage across an entire portion of the base unit; and applying the voltage across only a portion of the base unit. The method may include one of the steps of: flowing the current in a single direction through the base or counter units; flowing the current in different directions along different portions of the base or counter units; applying the voltage in a single direction through the base or counter units; applying the voltage along different directions along different portions of the base or counter units, and the like. The method may include the step of: providing multiple base units for the harmful waves, and the flowing may include one of the steps of: flowing the currents with the same amplitudes along a same direction in all of the base (or counter) units; flowing the currents of the same amplitudes in different directions along the base (or counter) units; flowing the currents of different amplitudes in the same direction in all of the base (or counter) units; flowing the currents of different amplitudes in different directions in the base (or counter) units, and the like. The method may include the step of: providing multiple base units for the harmful waves, while the applying may include one of the steps of: applying the voltages of the same amplitudes along a same direction in all of the base (or counter) units; applying the voltages of the same amplitudes in different directions along the base (or counter) units; applying the voltages of different amplitudes in the same direction in all of the base (or counter) units; applying the voltages of different amplitudes in different directions in the base (or counter) units, and the like.

Such flowings may include one of the steps of: flowing the currents of the same (or different) amplitudes in the counter unit; flowing in the counter unit another current which may not be derived from the current supplied to the base unit but may have a temporal pattern at least partially similar to that of the current supplied to the base unit; flowing along the counter unit another current which may be derived not from the current to the base unit and may have a temporal pattern different from that of the current to the base unit, and the like. The flowing such currents may include one of the steps of: flowing the currents in the base unit and in the counter unit; flowing such currents in the counter unit and in the base unit; and flowing the currents at least simultaneously in the base and counter units.

In another aspect of the present invention, an EMC display system may include therein at least one counter unit and at least one one wave source including multiple base units and may be capable of countering harmful electromagnetic waves which are irradiated by at least one of the base units of the wave source by emitting counter electromagnetic waves toward the harmful waves, by adjusting at least one configuration of the counter unit, and by suppressing the harmful waves with the counter waves from propagating to a target space and canceling the harmful waves by the counter waves in the target space, where the wave source includes an anode, a cathode, multiple pixels each of which is electrically coupled to the anode and cathode, an electric component of the EMC system, and/or an electronic component of the system, where the base units are arranged to include only portions of the wave source responsible for irradiating such harmful waves and/or affecting paths of propagation of the harmful waves therethrough, where the target space is defined between an user of the system and at least one of the base units, and where the system includes at least one screen made up of the pixels and displays a visual image thereon by manipulating the pixels using the anode and cathode.

In one exemplary embodiment of this aspect of the invention, such a system may be made by a process including the steps of: arranging at least one counter unit to have a width longer than that of the base unit; disposing the counter unit between the wave source and user while aligning its width with at least a portion of a wavefront of the harmful waves; configuring the counter unit to emit such counter waves defining wave characteristics similar to the harmful waves but having at least partially opposite phase angles thereto; and aligning the counter unit to propagate the counter waves toward the target space, thereby countering the harmful waves by the counter waves therein (to be referred to as the "first aligning" hereinafter). Such arranging and disposing may be replaced by the steps of: arranging at least one counter unit to define a width narrower than the base unit; and disposing the counter unit on an opposite side of the target space with respect to the wave source while aligning its width with at least a portion of a wavefront of the harmful waves.

In another exemplary embodiment of this aspect of the invention, a system may be made by a process including the steps of: identifying multiple wavefronts of the harmful waves; configuring a single counter unit to emit the counter waves defining multiple wavefronts which have phase angles at least partially opposite to those of the harmful waves and which are also capable of matching the wavefronts of the harmful waves when disposed at a preset distance from the base unit; disposing the counter unit in the distance from the base unit; and the first aligning.

In another exemplary embodiment of this aspect of the invention, a system may be made by a process including the steps of: providing at least two counter units; configuring such counter units to emit the counter waves which define similar (or identical) phase angles and have a first set of multiple wavefronts each corresponding to a sum of at least two wavefronts generated by the counter units; finding a relationship between a distance between such counter units and an increase in a radius of curvature of each of the wavefronts of the first set; identifying a second set of multiple wavefronts of the harmful waves; configuring the counter units to match the radii of curvature of the wavefronts of the first set with those of the wavefronts of the second set when disposed at preset distances from the base unit; disposing the counter units in the distances; and then the first aligning. The above configuring and finding may also be replaced by the steps of: configuring the counter units to emit the counter waves defining at least partially opposite phase angles and a first set of multiple wavefronts each corresponding to a sum of at least two wavefronts generated by the counter units; and finding a relationship between a distance between the counter units and a decrease in a radius of curvature of each of the wavefronts of the first set.

In another aspect of the present invention, an EMC display system may include therein at least one wave source with multiple base units and may be capable of countering harmful electromagnetic waves which are irradiated by at least one of the base units of the wave source by emitting counter electromagnetic waves to the harmful waves, by matching at least one feature of at least a portion of the system with that of at least one of the base units, and by at least one of suppressing the harmful waves with the counter waves from propagating to a target space and canceling the harmful waves with such counter waves in the target space, where the wave source includes an anode, a cathode, multiple pixels each of which electrically couples with the cathode and anode, an electric component of the system, and/or an electronic component of the system, where such base units are arranged to include only those portions of the wave source responsible for irradiating the harmful waves and/or affecting therethrough propagation paths of the harmful waves, where the target space is defined between at least one of the base units and an user of the system, and where aid system includes at least one screen made up of the pixels and displays a visual image therein by manipulating the anode and cathode.

In one exemplary embodiment of this aspect of the invention, such a system may be made by a process including the steps of: arranging at least one counter unit to match such a feature of the base unit; configuring the counter unit to emit the counter waves similar (or identical) to the harmful waves due to the arranging but having phase angles at least partially opposite to those of the harmful waves (to be referred to as the "second countering" hereinafter); and the first aligning. The above arranging may be replaced by one of the steps of: arranging at least one counter unit to define a configuration simpler than that of the base unit while at least minimally maintaining the feature; arranging at least one counter unit to define a configuration more complex than that of the base unit while at least minimally maintaining such a feature; arranging at least one counter unit to have a dimension defined by a less number of unit axes than the base unit while at least minimally maintaining the feature; and arranging at least one counter unit to have a dimension which is defined by a greater number of unit axes than that of the base unit while at least minimally maintaining the feature.

In another exemplary embodiment of this aspect of the invention, a system may be made by a process including the steps of: arranging a single counter unit to define a configuration simpler than that of a single base unit while maintaining the feature; the second countering; and the first aligning. The above arranging may be replaced by one of the steps of: arranging a single counter unit to define a configuration similar (or identical) to an arrangement of multiple base units while maintaining such a feature; arranging a single counter unit to define a dimension formed by less mutually orthogonal unit axes than an arrangement of multiple base units while maintaining the feature; and arranging a single counter unit to define a dimension formed by more mutually orthogonal unit axes than a dimension of multiple base units while maintaining the feature.

In another exemplary embodiment of this aspect of the invention, a system may be made by a process including the steps of: providing multiple counter units; arranging at least two of the counter units in a configuration simpler than that of a single base unit while maintaining the feature; configuring the counter units to emit the counter waves similar to (or identical to) the harmful waves due to such arranging but to defining phase angles at least partially opposite to those of such harmful waves; and aligning the counter units to propagate the counter waves to the target space, thereby countering the harmful waves by the counter waves therein. The above arranging may be replaced by one of the steps of: arranging at least two of the counter units in a configuration which is similar (or identical) to an arrangement of multiple base units while maintaining such a feature; arranging the counter units in an arrangement defining a dimension which is formed by less mutually orthogonal unit axes than a dimension of a single base unit while maintaining such a feature; and arranging the counter units in an arrangement defining a dimension formed by more mutually orthogonal unit axes than a dimension of multiple base units while maintaining the feature.

In another exemplary embodiment of this aspect of the invention, a system may be made by a process including the steps of: providing less counter units than such base units; approximating an arrangement of the base units by the counter units while maintaining such a feature; configuring such counter units to emit the counter waves which are similar to (or identical to) the harmful waves due to the approximating but define phase angles at least partially opposite to those of the harmful waves; and aligning the counter units to propagate the counter waves to the target space, thereby countering the harmful waves by the counter waves therein. The above providing and approximating may also be replaced by the steps of: providing more counter units for less base units; and approximating an arrangement of the base units by the counter units while disposing at least two of the counter units around at least one of the base units and maintaining the feature.

In another exemplary embodiment of this aspect of the invention, a system may be made by a process including the steps of: arranging at least one counter unit to move with respect to the base unit; configuring the counter unit to emit the counter waves similar (or identical) to the harmful waves but defining phase angles at least partially opposite to those of the harmful waves; finding a relation between a distance from the counter unit to the base units and an extent of matching between such counter and harmful waves; and then moving the counter unit a location where the extent attains its maximum, thereby countering the harmful waves by the counter waves in the target space.

In another aspect of the present invention, an EMC display system may include therein at least one wave source with multiple base units and may be capable of countering harmful electromagnetic waves which are irradiated by at least one of the base units of the wave source by emitting counter electromagnetic waves toward the harmful waves and matching such harmful waves therewith, and by suppressing the harmful waves with such counter waves from propagating toward a target space and/or canceling the harmful waves with the counter waves in the target space, where such a wave source includes an anode, a cathode, multiple pixels each of which electrically couples to the anode and cathode, an electric component of the system, and/or an electronic component thereof, where the base units are arranged to include only portions of the source responsible for irradiating such harmful waves and/or affecting propagation paths therethrough, where the target space is defined between an user of the system and at least one of the base units, and where the system includes at least one screen made up of such pixels and then displays a visual image thereon by manipulating the cathode and anode.

In one exemplary embodiment of this aspect of the invention, such a system may be made by a process including the steps of: identifying a first set of multiple wavefronts of such harmful waves; disposing at least one counter unit along at least one of the wavefronts; configuring the counter unit to emit the counter waves forming a second set of multiple wavefronts similar to (or identical to) the first set of the wavefronts in the target space due to the disposing; and the first aligning.

In another exemplary embodiment of this aspect of the invention, a system may be made by a process including the steps of: identifying multiple wavefronts of such harmful waves; configuring at least one counter unit to emit the counter waves defining multiple wavefronts similar to a shape and/or an arrangement of the counter unit; disposing the counter unit along at least one of the wavefronts of the harmful waves; and arranging the counter unit to emit such counter waves of which wavefronts are aligned with those of the harmful waves in the target space based upon the configuring, thereby countering the harmful waves by the counter waves therein. The above configuring and disposing may be replaced by the steps of: configuring at least one counter unit to emit the counter waves with multiple wavefronts different from at least one of a shape and an arrangement of the counter unit; and disposing such a counter unit across (or along) at least two of the wavefronts of the harmful waves based on the configuring.

In another exemplary embodiment of this aspect of the invention, such a system may be made by a process including the steps of: identifying multiple wavefronts of the harmful waves; disposing multiple counter units in an arrangement along at least one of the wavefronts; configuring the counter units to emit such counter waves with multiple wavefronts similar to the arrangement of the counter units; and arranging the counter units to emit such counter waves of which wavefronts are aligned with those of the harmful waves in the target space based on the configuring, thereby countering the harmful waves by the counter waves therein. The above disposing and configuring may be replaced by the steps of: disposing multiple counter units in an arrangement across (or along) at least two of the wavefronts; and configuring the counter units to emit the counter waves with multiple wavefronts different from the arrangement of the counter units.

In another exemplary embodiment of this aspect of the invention, a system may be made by a process including the steps of: identifying multiple wavefronts of such harmful waves; configuring at least one counter unit to emit such counter waves with multiple wavefronts each defining a radius of curvature; locating the counter unit between the base unit and target space; comparing shorter radii of curvature of the wavefronts of such counter waves with longer radii of curvature of the harmful waves; and configuring the counter unit to be disposed in a location where the radii of curvature of the wavefronts of the counter waves are configured to match those of the wavefronts of the harmful waves in the target space, thereby countering the harmful waves by the counter waves therein. The above locating and comparing may further be replaced by the steps of: locating the counter unit on an opposite side of the target space relative to the base unit; and comparing longer radii of curvature of the wavefronts of the counter waves to shorter radii of curvature of the harmful waves.

In another exemplary embodiment of this aspect of the invention, a system may be made by a process including the steps of: arranging at least one counter unit to move with respect to the base unit; configuring the counter unit to emit the counter waves similar (or identical) to the harmful waves but have phase angles at least partially opposite to those of the harmful waves; finding a relationship between a distance between the counter and base units and matching between radii of curvature of the counter waves and those of the harmful waves; assessing a location in which the wavefronts of the counter and harmful waves best match each other; and moving the counter unit to the location for best matching the harmful waves in the target space by such counter waves, thereby countering the harmful waves by the counter waves therein.

In another aspect of the present invention, an EMC display system may include therein at least one wave source with multiple base units and may be capable of countering harmful electromagnetic waves which are irradiated from at least one of such base units of the wave source by canceling the harmful waves in a target space and/or suppressing the harmful waves from propagating toward the target space, where the wave source includes an anode, a cathode, multiple pixels each electrically coupling with the anode and cathode, an electric component of the EMC system, and/or an electronic component thereof, where such base units are arranged to include only portions of the wave source responsible for irradiating the harmful waves and/or affecting therethrough propagation paths of such harmful waves, where the target space is defined between at least one of the base units and an user of the system, and where the EMC system includes at least screen made up of the pixels and displays a visual image thereon by manipulating the cathode and anode.

In one exemplary embodiment of this aspect of the invention, such a system may be made by a process including the steps of: arranging at least one counter unit to have a shape which is identical (or similar) to the base unit and to emit counter electromagnetic waves, and configuring such counter waves to have phase angles at least partially opposite to those of the harmful waves, to define wave characteristics at least partially similar to those of the harmful waves due to the shape and, therefore, to counter the harmful waves due to the opposite phase angles in the target space (to be referred to as the "third configuring" hereinafter).

In another exemplary embodiment of this aspect of the invention, a system may be made by a process including the steps of: arranging a single counter unit to define a shape of an 1-D (or 2-D, 3-D) analog of the base unit and to emit counter electromagnetic waves; and the third countering. Such arranging may be replaced by the step of: arranging a single counter unit to define a shape of an 1-D (or 2-D, 3-D) analog of at least two of multiple base units and to emit counter electromagnetic waves.

In another exemplary embodiment of this aspect of the invention, a system may be made by a process including the steps of: arranging multiple counter units at least two of which are configured to define shapes of 1-D (or 2-D, 3-D) analogs of such a base unit and to emit counter electromagnetic waves; and the third countering. The above arranging may also be replaced by one of the steps of: arranging multiple counter units at least two of which are configured to define shapes of 1-D (or 2-D, 3-D) analogs of at least two but not all of multiple base units and then to emit counter electromagnetic waves; and arranging multiple counter units at least two of which are configured to define shapes of 1-D (or 2-D, 3-D) analogs of each of multiple base units and to emit counter electromagnetic waves.

More product-by-process claims may be constructed by modifying the foregoing preambles of the apparatus and/or method claims and by appending thereonto such bodies of the apparatus and/or method claims. In addition, such process claims may include one or more of the above features of the apparatus and/or method claims of the present invention.

As used herein, the term "units" collectively refers to both of a "base unit" and a "counter unit" of an electromagnetically-countered display system of the present invention, where such a system is to be abbreviated as the "EMC display system," the "EMC system," or simply the "system" hereinafter. Such a classification between the "units" is primarily based upon their intended functions. That is, the "base unit" represents various parts of such an "EMC display system" for performing various intended functions of the system such as, e.g., displaying the visual image on its screen using its pixels, and so on. It is appreciated that all "base units" irradiate such harmful waves while performing the intended functions and that such "base units" are always incorporated in the above EMC system and in various prior art devices for similar purposes. In contrary, the "counter unit" refers to those parts of the EMC system which are to accomplish countering functions such as, e.g., canceling at least a portion of the harmful waves in the target space and/or suppressing and/or preventing such a portion of the harmful waves from propagating toward the target space. When desirable, such a "counter unit" may also be arranged to perform various functions intended for the "base unit" and, accordingly, serve as an extra "base unit" which not only serves as one of the electrodes (or a part thereof) or one of the pixels but also performs the countering function. Within the scope of this invention, however, such an unit is to be deemed as the "counter unit" throughout this description unless otherwise specified. Based upon this context, the "base unit" is omnipresent in any prior art display panels and/or devices, whereas the "counter unit" is neither physically not functionally present in these prior art devices.

The "base unit" is to be distinguished from a "wave source" within the scope of this invention. More particularly, the "wave source" collectively refers to portions of the EMC system irradiating such harmful waves, whereas the "base unit" specifically refers only to the portions of the "wave source" which are directly responsible for irradiating the harmful waves and/or affecting propagation paths of the harmful waves. For example, the anode and cathode of the EMC display system correspond to its "wave sources," while the "base units" of the EMC system generally include, e.g., those wires and/or strips of conductive materials. In addition, the pixels of the EMC display system may correspond to the "wave source," while portions of the pixels in which the source electric current flows and/or across which the source electric voltage is applied correspond to its "base units." Furthermore, other electric and/or electronic parts of the EMC display system may correspond to such "wave sources," whereas various electric and/or electronic components of such parts may serve as their "base units." A body, a case, and a coupler of the EMC system, however, may qualify as portions of such "wave sources" but may not qualify as the "base units," for these parts neither irradiate the harmful waves nor affect the propagation paths of such harmful waves. Therefore, a shape of the "wave source" is different from that of the "base unit," where the "base unit" may define the shape simpler or more complex than that of the "wave source." However, the "base unit" is generally deemed as a subset of the "wave source" and, therefore, the "base unit" almost always defines a size which is smaller than or at most equal to that of its "wave source."

It is appreciated that various counter units of this invention may be included in various display panels and/or various display devices with such panels. Accordingly, such panels and/or devices may be respectively converted into the EMC display panels and/or EMC display systems by various counter units. For the EMC display panels, their main intended functions are to display the visual image on their screen, where their waves sources and their base units have been enumerated above. For the EMC display systems, however, their intended functions include not only generating such visual images on their screens but also generating audio signals accompanying such images. Accordingly, the wave sources of these EMC systems may include various speakers in addition to those of the EMC display panels, where not only the details of the speakers and their waves sources but also various counter units therefor have been disclosed in the above co-pending Applications. Unless otherwise specified, the EMC display system includes therein its EMC display panel within the scope of this invention.

As used herein, the term "configuration" collectively refers a shape, size, and/or arrangement, while the term "disposition" collectively includes orientation, alignment, and/or distance. Accordingly, the "configuration" of the (counter or base) unit may refer to the shape of the unit, the size of the unit, and/or arrangement of the unit with respect to the other of the base and counter units. Similarly, the "disposition" of the unit may refer to the orientation and/or alignment of such a unit with respect to the other of the base and counter units, to the target space, to a direction of propagation of the harmful or counter waves, to a direction of the electric current flowing in or voltage applied across such a unit or the other of the base and counter units, and the like. The "disposition" of the unit may also refer to the distance to the other of the base and counter units therefrom, to the target space, and the like. When the system include multiple counter units, the "disposition" thereof may include the distance between at least two of such counter units.

Within the scope of the present invention, the term "wire" collectively refers to an article with a shape of a wire, a fiber, a filament, a rod, and/or a strand, and shapes of any other similarly elongated articles each of which may be straight or curved (i.e., curvilinear), and each of which may be formed into a loop, a coil, a roll, a spiral, a mesh, and the like. The term "strip" collectively refers to an article with a shape of a strip, a bar, a pad, and/or a tape, and shapes of any other planar or curved articles with large aspect ratios (i.e., ratios of lengths to widths or heights), each of which may be arranged straight or curved, each of which may be arranged in a two- or three-dimensional configuration, each of which may be arranged into a loop, a coil, a roll, a spiral, a mesh, and the like. In addition, the term "sheet" collectively refers to an article with a shape of a sheet, a slab, a foil, a film, a plate, and/or a layer, and shapes of any other articles which are wider than the "strip," each of which may be planar (i.e., two-dimensional or 2-D) or curved (i.e., three-dimensional or 3-D), each of which may be formed in a segment, a roll, and the like. The term "tube" collectively refers to an article which may define any of the shapes described hereinabove and to be described hereinafter and forming at least one lumen therethrough. Such a "tube" may be arranged straight or curved, may be arranged into a loop, a coil, a roll, a spiral, a mesh, and the like. The term "coil" collectively refers to an article defining a shape of a helix and/or a spring, and shapes of any other articles winding around an object along a longitudinal or short axis of such an object at a constant distance from the object, and the like. The "coil" may be arranged straight or curved, may also be arranged into a loop (such as a toroid), a coil, a roll, a spiral, a mesh, and the like. The term "spiral" collectively refers to an article defining a shape of another helix and/or spring which may, however, expand or shrink along the longitudinal or short axis of an object, and shapes of any other articles winding around such an object at varying distances, and the like. It is appreciated that a planar "spiral" may be formed on a single curvilinear plane which is normal to the longitudinal or short axis of the object. The term "mesh" collectively refers to an article with a shape a mesh, a net, a screen, a quilt, a fabric, and/or a garment, and shapes of any other articles which may be formed into a networking structure, a woven structure, an interwoven structure, and the like. The term "bundle" collectively refers to an article defining a shape of two or more of the same or different elongated shapes which are aligned side by side or laterally in such a manner that a cross-section of the "bundle" or a "bundled article" may include at least two of such shapes therein. The term "braid" collectively refers to an article with a shape of two or more of the same of different elongated shapes which are braided in such a manner that the "braid" or a "braided article" may consist of at least two of such shapes in a cross-section normal to a longitudinal and/or short axis thereof, where examples of such articles may include, but not be limited to, a thread, a yarn, any other articles made by prior art braiding techniques, and the like. It is to be understood that at least a portion of each of such articles formed according to the above terms in this paragraph may be arranged to be solid, hollow or porous such as, e.g., a foam, a sponge, and the like. It is also appreciated that each of such articles formed according to the foregoing terms of this paragraph may be arranged to include (or define) at least one hole, gap or opening.

Similarly and as used herein, the term "mixture" collectively refers to a liquid, a solution, a sol, a gel, an emulsion, a suspension, a slurry, and/or a powder, each of which may include therein multiple particles, particulates, grains, granules, filings, fragments, and/or pellets each of which may also have shapes of spheres, ellipsoids, cylinders, flakes, "wires," "strips," and the like, and each of which may be in a range of millimeters, microns or nanometers. When appropriate, such a "mixture" may include at least one solvent, at least one chemically, electrically, and/or magnetically inert filler for the purpose of providing mechanical strength and/or integrity thereto, and so on.

In addition, the term "combination" refers to a collection of different shapes examples of which may include, but not be limited to, the above wire, strip, sheet, tube, coil, spiral, mesh, their braid, and their bundle. The term "array" similarly refers to the collection of such shapes. However, the "array" refers to the "collection" which in addition forms multiple holes or openings therethrough.

As used herein, the terms "axial," "radial," and "angular" will be used in reference to a center axis of the system. Based thereupon, the term "axial direction" refers to a direction along the center axis of the system, while the term "radial direction" means another direction which is normal to such an "axial direction" and, therefore, which represents a direction extending away and outwardly from the center of the system. It is appreciated that such a "radial direction" may be other directions which extend away and outwardly from the center of the system and may be transverse but not necessarily perpendicular to the "axial direction." The term "angular direction" refers to another direction revolving about the "axial direction" in a clockwise or counterclockwise manner.

It is appreciated that definitions related to various electric and magnetic shields of this invention are similar to those as have been provided in the aforementioned co-pending Applications. Therefore, such definitions are deleted herein for simplicity of illustration.

Unless otherwise defined in the following specification, all technical and scientific terms used herein have the same meaning as commonly understood by one of ordinary skill in the art to which the present invention belongs. Although the methods or materials equivalent or similar to those described herein can be used in the practice or in the testing of the present invention, the suitable methods and materials are described below. All publications, patent applications, patents, and/or other references mentioned herein are incorporated by reference in their entirety. In case of any conflict, the present specification, including definitions, will control. In addition, the materials, methods, and examples are illustrative only and not intended to be limiting.

Additional aspects and/or advantages of the invention will be set forth in part in the description which follows and, in part, will be obvious from the description, or may be learned by practice of the invention.

BRIEF DESCRIPTION OF THE DRAWINGS

These and/or other aspects and advantages of the invention will become apparent and more readily appreciated from the following description of the embodiments, taken in conjunction with the accompanying drawings of which.

DETAILED DESCRIPTION OF THE EMBODIMENTS

Figure 1A:
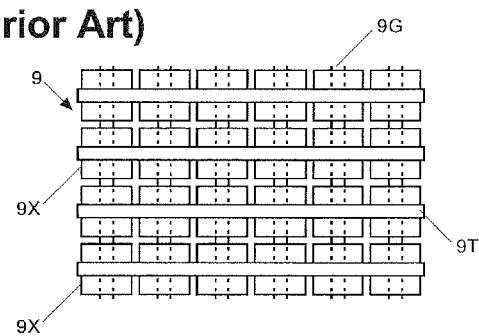
FIGS. 1A to 1F are top views of various prior art display units each including multiple pixels and electrodes supplying electrical energy thereto.

Reference will now be made in detail to the present embodiments of the present invention, examples of which are illustrated in the accompanying drawings, wherein like reference numerals refer to the like elements throughout. The embodiments are described below in order to explain the present invention by referring to the figures.

The present invention relates to an electromagnetically-countered display system with at least one wave source irradiating harmful electromagnetic waves and at least one counter unit for emitting counter electromagnetic waves and for countering the harmful waves by the counter waves, e.g., by canceling at least a portion of the harmful waves with the counter waves in a target space and/or by suppressing the harmful waves with such counter waves from propagating toward the target space. More particularly, the present invention relates to counter units for the electromagnetically-countered display systems and to various mechanisms for countering the harmful waves irradiated by various base units of the wave source with the counter units. Accordingly, the counter unit may be shaped, sized, and/or arranged for matching its configuration with that of at least one of the base units of the wave source, thereby emitting such counter waves which automatically match wave characteristics of the harmful waves. In the alternative, the counter unit may be shaped, sized, and/or disposed in an arrangement which is defined along one or more wavefronts of such harmful waves, thereby emitting the counter waves automatically matching wave characteristics of such harmful waves. The present invention also relates to various counter units provided as analogs of at least one of the base units of the wave source, where the analog approximates (or simplifies) at least one of the base units which is more complex than the counter unit, where the three- or two-dimensional base unit is simplified (or approximated) as the two- or one-dimensional analog, and the like. The present invention also relates to multiple counter units simpler than at least one of such base units but disposed in an arrangement approximating such a shape and/or arrangement of the base unit. The present invention also relates to the counter unit which may be shaped and/or sized according to the configuration of at least one of the base units and disposition thereof. In addition, the present invention relates to various countering modes where a single counter unit may counter a single base unit or all (or at least two but not all) of multiple base units, where multiple counter units may counter a single base unit, a greater number of the base units or a less number of multiple units, and the like. The present invention further relates to various electric and/or magnetic shields which may be used either alone or in conjunction with at least one of the counter units to minimize irradiation of the harmful waves by at least one of the base units.

The present invention relates to various methods of countering such harmful waves irradiated by various base units of multiple wave sources of the EMC display system by the counter waves by the source or wave matchings. More particularly, the present invention relates to various methods of forming the counter unit as an analog of at least one of the base units and emitting the counter waves matching such harmful waves, various methods of approximating at least one of the base units by the simpler counter unit for the countering, and various methods of approximating at least one of the base units by multiple simpler counter units. The present invention relates to various methods of disposing the counter unit along the wavefronts of the harmful waves and emitting the counter waves matching the wavefronts of the harmful waves, and various methods of disposing multiple counter units along the wavefronts of the harmful waves and emitting the counter waves with the counter units matching the wavefronts. The present invention also relates to various methods of adjusting the wavefronts of the counter waves by disposing the counter unit closer to and/or farther away from the target space with respect to at least one of the base units, various methods of controlling radii of curvature of such wavefronts of the counter waves by incorporating one or multiple counter units emitting such waves with the same or opposite phase angles, and various methods of manipulating such wavefronts of the counter waves by disposing one or multiple counter units of the shape similar to or different from that of at least one of the base units. The present invention also relates to various methods of countering the harmful waves irradiated from a single or multiple base units with the counter waves emitted by a single or multiple counter units. Accordingly, the present invention also relates to various methods of emitting the counter waves by a single counter unit to counter the harmful waves irradiated by one or more base units and various methods of emitting the counter waves emitted from two or more counter units for countering such harmful waves irradiated from a single or multiple base units. In addition, the present invention also relates to various methods of minimizing irradiation of such harmful waves by incorporating the electric shields, by incorporating the magnetic shields, by incorporating one or both of such shields in conjunction with the above counter units, and the like.

The present invention further relates to various processes for providing various counter units for such EMC display systems and various EMC systems incorporating therein one or multiple counter units. More particularly, the present invention relates to various processes for providing such counter units capable of emitting the counter waves defining such wavefronts similar to (or different from) the shapes of the counter units, various processes for forming the counter units as the above analogs of at least one of such base units, various processes for providing the counter units emitting the counter waves having the similar or opposite phase angles, various processes for providing the counter units defining the wavefronts shaped similar to such harmful waves, and various processes for disposing the counter units in a preset arrangement and emitting thereby the counter waves of the wavefronts similar to such an arrangement. The present invention also relates to various processes for assigning a single counter unit in order to counter the harmful waves irradiated by a single base unit for the local countering or to counter the harmful waves irradiated by multiple base units for the global countering, various processes for assigning multiple counter units to counter the harmful waves irradiated from a single base unit for the global countering, and to counter the harmful waves irradiated by multiple base units for the local and/or global countering depending on numbers of the counter and base units. The present invention also relates to various processes for including such electric and/or magnetic shields for minimizing the irradiation of the harmful waves and various processes for minimizing the irradiation of such harmful waves by employing such shields and/or the above counter units.

The basic principle of the counter units of the EMC display systems of the present invention is to emit the counter waves defining the wavefronts similar (or identical) to those of the harmful waves but defining the phase angles at least partially opposite to those of the harmful waves. Therefore, by propagating the counter waves toward the target space, the counter waves may effectively counter the harmful waves in the target space by, e.g., canceling at least a portion of the harmful waves with the counter waves therein, suppressing the harmful waves with the counter waves from propagating theretoward, and the like. To this end, such counter units preferably emit the counter waves defining the wavefronts matching those of the harmful waves by various mechanisms. In one example, such counter units are shaped similar (or identical) to at least one of the base units of the waves sources, or arranged similar (or identical) to the base unit and, accordingly, emit the counter waves capable of countering the harmful waves in the target space. In another example, the counter units are disposed along or across a single or multiple wavefronts of the harmful waves, emit the counter waves similar (or identical) to the harmful waves and, therefore, counter the harmful waves in the target space. In these examples, the counter units emit the counter waves forming the wavefronts similar (or identical) to the shapes of the counter units themselves, and those counter waves define the phase angles at least partially opposite to the phase angles of the harmful waves. In another example, such counter units are shaped differently from at least one of the base units, but rather disposed in an arrangement in which the counter waves emitted thereby match the harmful waves in the target space. In another example, the counter units are disposed across different wavefronts of such harmful waves but emit the counter waves similar (or identical) to the harmful waves, thereby, countering the harmful waves in the target space. In these last two examples, the counter units may be arranged to emit the counter waves defining such wavefronts which may or may not be similar (or identical) to the shapes of the counter units themselves, while the counter waves have the phase angles which are at least partially opposite to those of the harmful waves.

The basic principle of various generic counter units of the EMC display system of the present invention may be implemented to various conventional devices for minimizing irradiation of the harmful waves therefrom. For example, the counter units may be implemented to any base units of electrically conductive wires, coils, and/or sheets of the EMC display system or, alternatively, to any electrically semiconductive and/or insulative wires, coils, and/or sheets of the EMC display system for minimizing the irradiation of the harmful waves by countering the harmful waves by the counter waves, e.g., by canceling at least a portion of the harmful waves in the target space and/or suppressing such harmful waves from propagating to the target space, where the counter units may be made of and/or include at least one electrically conductive, insulative or semiconductive material. Such counter units may be implemented to any of the base units of the shapes which may be formed by including one or multiple wires, coils, and/or sheets, by modifying such shapes of one or multiple wires, coils, and/or sheets, where a few examples of the modified shapes may include a solenoid and toroid each of which may be formed by modifying the shape of the coil. Therefore, such counter units may be implemented into various display units of the EMC systems such as cathode ray tube display units, liquid crystal display units, organic and/or inorganic light emitting display units, plasma display units, and other display units which include multiple pixels and is also capable of emitting visible light rays when supplied with the source electrical energy.

It is appreciated that various counter units of such EMC display systems of this invention may be implemented to any display devices each including at least one of the base units and, accordingly, may irradiate such harmful waves including electric waves (to be abbreviated as "EWs" hereinafter) and magnetic waves (to be abbreviated as "MWs" hereinafter) of frequencies ranging about 50 to 60 Hz and/or other EWs and MWs of higher frequencies. It is appreciated that the EMC display systems of this invention may also be incorporated to any display devices and/or units of portable or stationary electric and/or electronic devices which include at least one base unit examples of which have been provided heretofore. It is further appreciated that the counter units may be provided in a micron-scale and included in semiconductor chips and circuits such as LSI and VLSI devices for such EMC display systems, that the counter units for the EMC display systems may also be formed in a nano-scale and incorporated to various nano devices including at least one base unit which may be a single molecule or a compound, or may be a cluster of multiple molecules or compounds, and so on.

Various aspects and/or embodiments of various systems, methods, and/or processes of this invention will now be described more particularly with reference to the accompanying drawings and text, where such aspects and/or embodiments thereof only represent different forms. Such systems, methods, and/or processes of this invention, however, may also be embodied in many other different forms and, accordingly, should not be limited to such aspects and/or embodiments which are set forth herein. Rather, various exemplary aspects and/or embodiments described herein are provided so that this disclosure will be thorough and complete, and fully convey the scope of the present invention to one of ordinary skill in the relevant art.

Unless otherwise specified, it is to be understood that various members, units, elements, and parts of various systems of the present invention are not typically drawn to scales and/or proportions for ease of illustration. It is also to be understood that such members, units, elements, and/or parts of various systems of this invention designated by the same numerals may typically represent the same, similar, and/or functionally equivalent members, units, elements, and/or parts thereof, respectively.

FIGS. 1A to 1F show top views of various prior art display units each including multiple pixels and electrodes supplying electrical energy thereto, where each display unit is arranged to emit visual light rays upwardly from the sheet. Based on this definition, the pixels of the display units of FIGS. 1A to 1E receive the electrical energy in a direction at least partially perpendicular to the sheet (i.e., along a direction coinciding with or opposite to a direction of the visible light rays), whereas the pixels of the display unit of FIG. 1F receives the electrical energy in a direction at least partially parallel to the sheet (i.e., in a direction transverse to the direction of visible light rays). Accordingly, examples of the prior art display units of FIGS. 1A to 1E may include the conventional organic or inorganic light emitting diode units, plasma display units, and other display units where light emitting or transmitting elements of the pixels receive the energy along the direction parallel or opposite the direction of such light rays, while examples of the prior art display unit of FIG. 1F may include the prior art liquid crystal display units and other display units where light emitting or transmitting elements of the pixels receive the energy along the direction transverse to the direction of the light rays. It is appreciated that various display units of the following figures may include other parts not included therein, where examples of such parts may include, but not be limited to, substrates on which such pixels are provided, external circuits or drivers manipulating routes and directions of the electrical energy supplied to those pixels, energy sources supplying such electrical energy, and the like.

In one example of FIG. 1A, a conventional display unit 9 includes multiple pixels 9X arranged in an array with multiple rows and columns. The display unit 9 also includes at least one first electrode and a second electrode, where the former serves as one of an anode and a cathode, while the latter serves as the other of the anode and cathode. The first electrode also includes multiple first electric conductive paths 9G which vertically extend parallel to each other and electrically couple with bottom portions of the pixels 9X, whereas the second electrode includes multiple second electric conductive paths 9T horizontally extending parallel to each other and electrically coupling with top portions of the pixels 9X. The display unit 9 includes at least one external circuitry or a circuit driver (not included in the figure) which operatively couples with each of the first and second conductive paths 9G, 9T and directs the electrical energy to one or more selected pixels 9X by delivering the energy (e.g., electric current and/or voltage) to those first and second paths 9F, 9T coupling with such pixels 9X. It is to be understood that the display unit 9 in this arrangement is generally termed as a "passive-matrix" display unit 9 in that the pixels 9X are selected sequentially by the driver.

In operation, the driver selects one or more pixels 9X to be turned on. Based upon locations of the pixels 9X, the driver delivers the electrical energy to the corresponding first and second paths 9G, 9T so that the electric energy is applied vertically to the pixels 9X. In one example, such a display unit 9 corresponds to a conventional organic light emitting diode unit (to be abbreviated as the "OLED" unit hereinafter), where the second electrode and its second conductive paths 9T serve as the cathode, while the first electrode and its first conductive paths 9G serve as the anode. Each pixel 9X includes two or more layers each including specific organic molecules, where one of such layers serves as a conductive layer, while another of such layers serves as an emissive layer. When the energy source applies the electrical energy between such cathode and anode and applies the electric voltage across the pixel 9X, the electrical current begins to flow from the cathode to the anode through such organic layers. The cathode gives electrons to the emissive organic layer, while the anode removes electrons from the conductive layer of organic molecules or gives electron holes to the conductive layer. At a boundary between the emissive and conductive organic layers, such electrons find the electron holes and fill the holes by falling into lower energy levels and giving up the energy in the form of photons of light lays through a process called "electro-phosphorescence". Accordingly, such an OLED unit 9 may emit the visible light rays through the transparent cathode (i.e., a top emitting OLED) or through both of the transparent cathode and anode (i.e., a transparent OLED). In general, a color of such visible light rays depends on the type of organic molecules in the emissive layer, where an intensity or brightness of the light depends on an amount of the electric current applied. Further details of such OLED display units 9 are well documented in various references and well known to those skilled in the relevant art. In another example, the display unit 9 may correspond to a prior art inorganic (or small molecule) light emitting diode unit which is generally similar to the OLED unit but includes inorganic small molecules in the conductive and/or emissive layers. Other configurational and/or operational characteristics of the inorganic light emitting diode unit are similar or identical to those of the OLED unit. In another example, the display unit 9 corresponds to a conventional plasma display panel (to be abbreviated as the "PDP" unit hereinafter), where the second electrode and its second conductive paths 9T serve as a display electrode, where the first electrode and its first conductive paths 9G serve as an address electrode, and where the electrodes and paths 9G, 9T serve as the cathode and anode. Each pixel 9X forms a cavity defined between a rib of the unit 9 and open through its top, includes ionizing gases such as neon, xenon, and/or their mixture, is coated with phosphor materials, and is also covered by additional layers such as, e.g., a conductive layer, a dielectric layer, a protective layer, and the like. To charge a specific pixel 9X, the driver delivers the electrical energy from the energy source through the selected address and display electrodes. As the intersecting electrodes are charged with the voltage gradient therebetween, the electric current flows through the ionizing gases which are trapped inside the pixel 9X. The ionizing gases stimulated by the current create a rapid flow of charged particles and release ultraviolet photons which interact with the phosphor material coated over an inner wall of the pixel 9X. As the ultraviolet photon hits the phosphor atom in the pixel 9X, one of the phosphor's electrons jumps to a higher energy level as the phosphor atom is heated up. When the electron falls back to its normal level, however, it releases energy in the form of a visible light photon. Therefore, the PDP unit 9 emits the visible light rays from its millions of pixels 9X and then transmits such rays through the transparent display electrode. In general, a color of the visible light rays depends on the type of the ionizing gases trapped in each pixel 9X, where an intensity or brightness of such light rays depends on an amount of the electric current applied. Further details of the prior art PDP units 9 are well documented in various references and well known to those skilled in the relevant art. In another example, such a display unit 9 corresponds to a prior art liquid crystal display unit (to be abbreviated as the "LCD" unit hereinafter), where each pixel 9X includes at least two transparent filter layers of polarizing materials sandwiching therein a pair of transparent planar cathode and anode which in turn interpose therebetween a layer of liquid crystals. In this LCD unit, it is important to align axes of polarity of a pair of polarizing filters to be normal to each other, to form parallel microscopic grooves on the electrodes, i.e., the cathode and anode, and to align the grooves of the electrodes to be perpendicular to each other. Before the driver delivers the electrical energy thereto, the liquid crystals are generally in their relaxed state. The liquid crystal molecules begin to align themselves with the grooves provided on both electrodes in a helical structure or, in other words, twist the crystals. Light emitted from a light source and passing through one polarizing filter is then rotated as it passes through the liquid crystals, allowing it to pass through the second polarizing filter. One half of the light is absorbed by the first polarizing filter, but otherwise the entire LCD unit 9 is maintained transparent. When the driver supplies the electrical energy through the electrodes, the liquid crystal molecules are pulled parallel to the electric fields generated between the electrodes, thus reducing a rotation of the entering light. When the liquid crystals are completely untwisted, the light passing through the liquid crystals will be polarized perpendicular to the second polarizing filter. Therefore, such a pixel 9X is completely blocked and appears unlit. By controlling the twist of the liquid crystal molecules in each pixel 9X, light may be allowed to pass through the LCD unit 9 in varying amounts, correspondingly illuminating the pixel 9X. It is normal to align the polarizing filters so that pixels are transparent when relaxed and become opaque in the presence of the electric fields, however the opposite is sometimes done for special effect. Further details of the prior art LCD units 9 are well documented in various references and well known to those skilled in the relevant art.

Figure 1D:
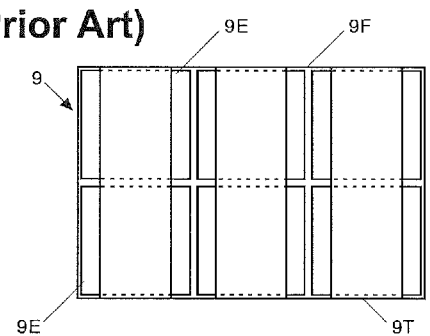
Figure 1B:
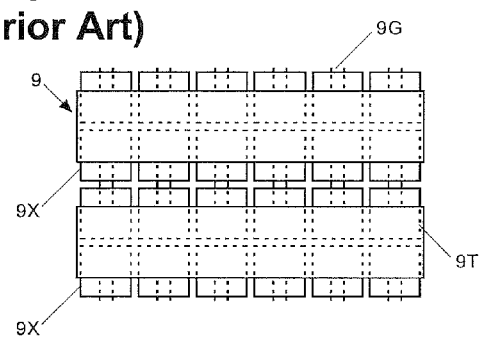

In another example of FIG. 1B, a conventional display unit 9 similarly includes multiple pixels 9X arranged in an array with multiple rows and columns, at least one first electrode including multiple first paths 9G, and at least one second electrode with multiple second paths 9T, where the first paths 9G vertically extend parallel to each other and are electrically coupled to bottom portions of the pixels 9X, whereas the second paths 9T horizontally extend parallel to each other and are electrically coupled to top portions of the pixels 9X. In contrary to those of FIG. 1A, each second path 9T is arranged to sit over multiple rows of pixels 9X so that the external circuit may supply the electrical energy to multiple pixels 9X intersected by such first and second paths 9G, 9T. The display unit 9 in this arrangement is another passive matrix display unit 9. It is to be understood that the first and second electrode may be interchanged in such a manner that the display unit 9 include the second paths 9T identical to those of FIG. 1A and that each first path 9G contacts a pair of adjacent pixels 9X. Other configurational and/or operational characteristics of the display unit 9 of FIG. 1B are similar or identical to those of the display unit of FIG. 1A.

Figure 1E:
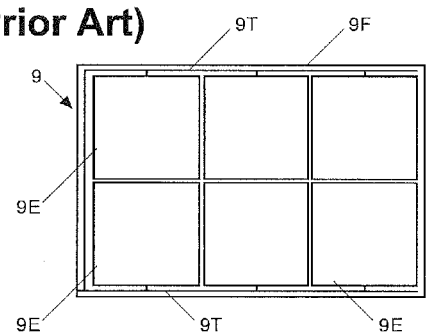
Figure 1C:
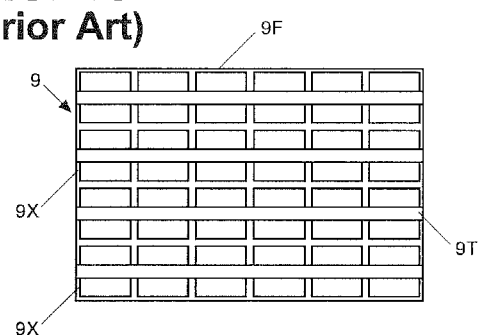

In another example of FIG. 1C, a conventional display unit 9 similarly includes multiple pixels 9X and second electrode with multiple second paths 9T each identical to those of FIG. 1A. In contrary to those of FIGS. 1A and 1B, however, the first electrode 9E has a planar configuration and is arranged to electrically contact all or at least a substantial number of pixels 9X. Accordingly, such a driver may deliver the electrical energy to and select multiple pixels 9X sitting on a single or multiple rows thereof. It is appreciated that the first and second electrodes are interchanged in such a mode that the display unit 9 include the first electrode 9F identical to those of FIG. 1A and that the second electrode defines the planar configuration and contacting all or at least a substantial number of pixels 9X. Such second paths 9T may further be replaced by the wider counterparts of FIG. 1B. Other configurational and/or operational characteristics of the display unit 9 of FIG. 1C are similar or identical to those of the display units of FIGS. 1A and 1B.

In another example of FIG. 1D, a conventional display unit 9 also includes multiple pixels which are arranged in an array with multiple rows and columns. In contrary to those of FIGS. 1A to 1C, such pixels are rather grouped in multiple sets 9E of pixels which also define an array of multiple rows and columns, where each pixel set 9E may include therein a preset number of columns and another preset number of rows of such pixels. The display unit 9 also includes the planar first electrode 9F which is similar to that of FIG. 1C as well as a second electrode consisting of multiple second conductive paths 9T each of which extends vertically parallel to each other and electrically couple with a top portion of each pixel set 9E. Unless the circuit driver is given another provision, the driver may only supply the electrical energy to the set 9E of pixels intersected by the second path 9T selected thereby. It is to be understood that such first and second electrodes are interchanged in a manner that the display unit 9 include the first planar electrode 9F with multiple first paths horizontally or vertically coupling with the pixel sets 9E and the second planar electrode, that at least one second path 9T may electrically couple with multiple pixel sets 9E, that the first electrode 9F may be similar to that of FIGS. 1A and 1B, and the like. Other configurational and/or operational characteristics of the display unit 9 of FIG. 1D are similar or identical to those of the display units of FIGS. 1A to 1C.

In another example of FIG. 1E, a conventional display unit 9 also includes multiple pixels which are arranged in an array with multiple rows and columns and which are also grouped in multiple sets 9E of pixels similar to those of FIG. 1D. The display unit 9 includes the planar first electrode 9F which is similar to that of FIG. 1C but includes multiple controllers which are coupled on top of each set 9E of pixels and arranged to manipulate the supply of the electrical energy to each pixel included in the set 9E. In general, such controllers are formed in a very small thickness, e.g., as thin-film transistors. The display unit 9 also has at least one second electrode including multiple second conductive paths 9T to supply the electrical energy to each controller and each pixel set 9E controlled by such a controller. It is appreciated that the display unit 9 in such an arrangement is generally termed as an "active-matrix" display unit in that the pixels of each set 9E may be independently selected by its own controller. It is to be understood that such first and second electrodes are interchanged in a manner that the display unit 9 include the first electrode 9F with multiple first paths horizontally or vertically coupling with such controllers for multiple pixel sets 9E and includes the second planar electrode, that the first electrode may be replaced by the first electrode of FIG. 1A or by the second electrode of FIG. 1B, and the like. Further configurational and/or operational characteristics of the display unit 9 of FIG. 1E are similar or identical to those of the display units of FIGS. 1A to 1D.

Figure 1F:
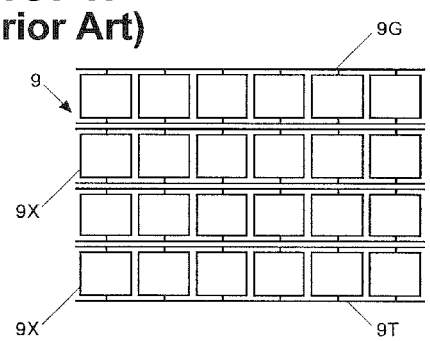

In another example of FIG. 1F, a conventional display unit 9 similarly includes multiple pixels 9X which are arranged in an array of multiple rows and columns, at least one first electrode, and at least one second electrode. Contrary to such electrodes of FIGS. 1A to 1E, the first and second electrodes includes multiple first and second electric conductive paths 9G, 9T, respectively, both of which extend laterally and parallel to each other. In addition, the first paths 9G electrically couple with side portions of the pixels 9X, while the second paths 9T electrically couple with opposite side portions of the pixels 9X. The display unit 9 includes the external circuitry or circuit driver operatively coupling with each of the first and second paths 9G, 9T and directing the electrical energy to one or more selected pixels 9X by delivering the energy (e.g., electric current and/or voltage) along those first and second paths 9F, 9T coupling with such pixels 9X. It is to be understood that the display unit 9 is another passive-matrix display unit 9 in that the pixels 9X are selected sequentially by the driver.

In operation, the driver selects one or more pixels 9X to be turned on. Based upon locations of the pixels 9X, the driver delivers the electrical energy to the corresponding first and second paths 9G, 9T so that the electrical energy is applied vertically to the pixels 9X. In general, the display unit 9 may be any of the conventional OLED units, IOLED units, PDP units, LCD units, and so on, where the above first and second paths 9G, 9T of the cathodes and anodes couple with the pixels 9X on their sides. It is to be understood that all of the above display units require the electrical energy to be applied across the height of their pixels 9X. Therefore, the coupling arrangement of FIG. 1F may be used when such display units include the conductive paths 9G, 9T which couple with the sides of the pixels 9X, where the light emitting and/or transmitting elements of such pixels 9X may receive the electrical energy from the paths 9G, 9T by other conductive portions which are not parts of the paths 9G, 9T. Alternatively, the coupling arrangement of FIG. 1F may be deemed as an approximation of that of FIG. 1A, in which a total length of the first and second paths 9G, 9T which are not disposed directly over the pixels 9X or, in other words, a total length of such paths 9G, 9T extending between the pixels 9X may significantly exceed a total length of such paths 9G, 9T disposed directly over the pixels 9X. It is appreciated that the arrangement of FIG. 1F may be modified and applied to other electrodes as exemplified in FIGS. 1A to 1E, including the active-matrix arrangement of FIG. 1E and its modifications or variations exemplified hereinabove. Further configurational and/or operational characteristics of the display unit 9 of FIG. 1F are similar or identical to those of the display units of FIGS. 1A to 1E.

The prior art display units may include variations and/or modifications of those described in the above figures. In one example, the display unit may include any desirable number of any of the above pixels arranged in any number of rows and/or columns, where exact numbers may be determined by various factors such as, e.g., a desirable size of the display unit, a size of each pixel, a size of a gap to be provided between the adjoining pixels, and the like. Therefore, such pixels may be arranged to define the display unit of a preset aspect ration which may be, e.g., 4:3, 5:3, 5:4, 7:5, 7:3, 9:4, 9:5, 9:7, 16:9, 25:9, 25:16, and the like, where the pixels may define any of the above OLED, IOLED, PDP, LCD, DLP, and/or SED display units. In another example, such pixels of any of such display units may also be grouped into any desirable number of pixels sets each of which may include any desirable number of pixels therein, where sizes of the pixel sets and/or the number of pixels in such sets of pixels may be identical to each other or, in the alternative, may be different from each other. In another example, the pixels of any of the above display units may be arranged in a regular rectangular or square matrix or in a staggered matrix in which pixels of a given row (or column) may be located between the pixels of the adjacent row (or column). In another example, the drivers of such display units may drive their pixels in various modes such as, e.g., a non-progressive mode where only a limited number of pixels are turned on at any given moment, a progressive mode where all or at least a substantial number of pixels are turned on, an ALIS mode (representing "alternate lighting of surfaces") where only one half of the pixels are turned on, and the like. In another example, the pixels may be formed as the cavities or cells each of which is individually defined on the screen of the display unit. Alternatively, the pixels may be formed as elongated troughs along each of which multiple pixels are defined by the electrodes extending thereover or therebelow. In another example, the pixels may also include multiple subpixels so that each pixel described in such figures may in fact consist of multiple subpixels. One example of this arrangement may be used to emit and/or transmit the visible color rays, where each pixel includes a red subpixel, a green subpixel, and a blue subpixel and where each of these subpixels may also be driven by separate paths which operate similar to the conductive paths.

As described hereinabove, the prior art display units may include various wave sources such as, e.g., the first and second electrodes (also referred to as top and bottom electrodes or display and address electrodes), pixels of various passive and/or active-matrix OLED units, pixels of the passive and/or active-matrix inorganic light emitting diode units which will be abbreviated as the "IOLED" units hereinafter, pixels of the passive and/or active-matrix PDP units, pixels of the passive and/or active-matrix LCD units, and phosphor pixels of the CRT units. Although not exemplified in the above figures, the wave sources may further include the electrodes and pixels of other prior art display units which may include, but not limited to, digital light processing units which will be referred to as the "DLP" units hereinafter, surface-conduction electron-emitting devices which will be referred to as the "SED" units hereinafter, and other display units including multiple pixels capable of emitting and/or transmitting the visible light rays therethrough in response to the electrical energy (i.e., electric current and/or voltage) applied thereto either vertically or transversely. In addition, such wave sources may include the beam generators and steering coils of the CRT units. Moreover, the wave sources of the display units may also include various electric and/or electronic parts thereof. As described hereinabove, each of such wave sources includes various base units such as, e.g., a single or multiple conductive paths of each of the first and second electrodes, pixels of the above display units, various electric and/or electronic components of various parts of such units, and the like. Although not exemplified in the figures, such display units may also include the prior art cathode ray tube units (to be referred to as the "CRT" units hereinafter), and the wave sources of the CRT units may include their electron beam generators and steering units.

The base units of these wave sources almost always irradiate such extremely low-frequency harmful electromagnetic waves in the frequency ranges of, e.g., less than about 100 kHz, 50 kHz, 10 kHz, 5 kHz, 1 kHz or less. It is to be understood that the frequencies of these harmful waves may be dependent not only on the frequency of the electrical energy provided from the energy source to the display unit but also on the frequency of the electrical energy supplied to those pixels by the driver or external circuit, where the latter may constitute the "primary" base units in many circumstances. More particularly, various electrodes and their conductive paths which may be shaped into (extremely) thin wires and/or strips may constitute the primary base units of a prior art display unit of a particular type, for such electrodes and/or path must cover an entire area of a screen of the display unit both on and below such a screen. It is true that the pixels emitting or transmitting the visible light rays therethrough also have to cover the entire or at least a substantial area of the screen. As described hereinabove, however, the pixels of most conventional display units (probably except those of the CRT units) are designed to receive the electric current and/or voltage perpendicular to the screen (or to the sheet of FIGS. 1A to 1 F0 while irradiating such harmful waves propagating primarily along directions parallel to the screen (or sheet). In contrary, the electrodes and their conductive paths generally extend parallel to the screen (or sheet), and receive the electric current and/or voltage therealong, thereby irradiating such harmful waves primarily propagating along directions perpendicular to the screen (or sheet). In this context, such electrodes and their conductive paths generally qualify as the primary base units of various display units, whereas the pixels may serve as the secondary base units of the display units. It is also probable that the pixels may irradiate the harmful waves while emitting the visible light rays, in which the pixels may have to be regarded as the primary base units as well. In the CRT display units, however, various components of the beam generators as well as various coils of the steering units may serve as the primary base units, where the phosphor materials coated on its screen may also be considered as the primary base units when such materials irradiate the harmful waves while emitting the visible light rays. In addition, other conductive, semiconductive, and/or insulative parts of various display units may also serve as the primary or secondary units based on the intensity of the harmful waves irradiated therefrom. In any rate, it is to be reminded that various counter units of the present invention are designed to counter both of such primary and secondary base units. Therefore, when the counter unit is arranged to simplify (or approximate) only one of the above primary (or secondary) base units, the counter unit may be shaped and/or sized as one or more of various analogs simplifying (or approximating) one of the base units for countering the harmful waves irradiated from only one of such base units. When desirable, two or more of such analogs may be disposed in various locations around at least one of such primary (or secondary) base units or, in the alternative, may mechanically and/or electrically couple with each other, supplied with the electric energy in a preset pattern, and/or disposed in a preset location for countering the harmful waves irradiated by two or more of the base units. The counter units may also be provided as an unitary article which approximates two or more of such primary base units.

In order to counter such harmful waves irradiated from various base units of the conventional display units, various counter units are implemented for emitting counter electromagnetic waves (to be abbreviated as the "counter waves" hereinafter) and to counter the harmful waves therewith, e.g., by suppressing the harmful waves with such counter waves from propagating toward the target space, canceling at least a portion of the harmful waves with such counter waves in a target space, and the like. Thereby, the conventional display units incorporated with one or more of such counter units may be converted into the EMC display systems (or simply EMC systems) of the present invention. Various counter units and their countering mechanisms will now be enumerated. It is appreciated, however, that following counter units and countering mechanisms therefor of this invention may be embodied in many other different forms as well and, accordingly, should not be limited only to the following counter units and/or countering mechanisms thereof to be set forth herein. Rather, various exemplary counter units and various countering mechanisms described hereinafter are provided so that this disclosure is thorough and complete, and fully conveys the scope of this invention to one of ordinary skill in the art. It is further appreciated that various counter units and their countering mechanisms which have been described hereinabove and which are to be disclosed hereinafter may also apply to any conventional display units exemplified in the above figures, to other prior art display devices which have not been exemplified in such figures but have been disclosed in conjunction therewith as their modifications or variations, to other prior art display units including electrodes and/or pixels both of which may also be provided from those of the aforementioned prior art display units, and the like. Therefore, any of such conventional display units may be converted into such EMC systems of this invention by incorporating thereinto one or more of the counter units operating in one or more of the countering mechanisms.

As described above, various counter units of the present invention may be incorporated to the above prior art display devices and/or their display units in order to convert such into the EMC display systems and EMC display units, respectively. Alternatively, various counter units may be incorporated into at least one set of pixels of the prior art display units such that such a pixel set may be converted into the EMC pixel set and, therefore, the display unit incorporating such a pixel set may be converted into the EMC display unit.

In a generic aspect of the present invention, an EMC display system generally includes therein multiple wave sources and at least one counter unit, and counters harmful electromagnetic waves (to be abbreviated as the "harmful waves" hereinafter) which are irradiated from the wave sources with counter electromagnetic waves (to be abbreviated as the "counter waves" hereinafter) emitted by the counter unit. Each of such wave sources includes at least one base unit which is the real source of the harmful waves, i.e., irradiating the harmful waves, affecting paths of propagation of such harmful waves while maintaining or altering their amplitudes and/or phase angles, and so on, where examples of such base units may include, but not be limited to, a conductive or semiconductive article such as a wire, a strip, a plate, a sheet, a ring thereof, a coil thereof, a spiral thereof, a mesh thereof, and so on, all of which emit the harmful waves when electric current flows therein, an insulative article such as a wire, a strip, a plate, a sheet, a ring thereof, a coil thereof, a spiral thereof, and a mesh thereof all of which may not carry the electric current but emit the harmful waves when electric voltage is applied thereacross, a permanent magnet which affects the direction, paths, and/or amplitudes of the harmful waves, and so on. Each wave source may include at least one optional part mechanically supporting or retaining its base units but neither irradiating nor affecting the paths of propagation of such harmful waves, where examples of the optional parts may include, but not be limited to, a case enclosing one or more of its base units, a protective cover, a coupler, any parts thereof in which the electric current does not flow, any parts thereof across which the voltage is not applied, and so on. The counter unit is arranged to emit the counter waves capable of countering such counter waves, e.g., by canceling the harmful waves and/or by suppressing the harmful waves from propagating in a specific direction. The counter unit may be arranged to counter the harmful waves in every direction from at least one of the base units of the wave source, e.g., above, below and around at least one of the base units. This embodiment, however, may be costly, may not be feasible, and/or may not be necessary, particularly when the EMC display system is to be disposed in a specific orientation by an user to be protected from the harmful waves. In such a case, the counter is arranged to counter the harmful waves only in or around a specific target space (or area) which is generally defined between at least one of the base units and the user (or a specific body part thereof).

In order for the counter waves to counter (i.e., cancel and/or suppress) such harmful waves, there are a few prerequisite which the counter waves must satisfy. The first is the phase angles of the counter waves. In general, the counter waves preferably define the phase angles which are at least partially or substantially opposite to those of the harmful waves so that the counter waves may cancel and/or suppress the harmful waves when propagated to the target space from the same side as at least one of the base units. In the alternative, the counter waves may define the phase angles at least partially similar (or identical) to those of the harmful waves so that the counter waves cancel and/or suppress the harmful waves when propagated to the target space from an opposite side of at least one of the base units. When such an EMC display system includes multiple counter units, each of the counter units may emit the counter waves defining the same, similar or different phase angles. The next is the amplitudes of the counter waves. In contrary to their phase angles which must satisfy the preset relation to those of the harmful waves, the counter waves may have any amplitudes which effectively counter the harmful waves in the target space. When disposed closer to the target space than at least one of the base units, e.g., the counter unit has only to emit such counter waves with the amplitudes less than those of the harmful waves. Conversely, the counter unit disposed farther from at least one of the base units has to emit such counter waves of the amplitudes greater than those of the harmful waves, whereas the counter unit disposed flush with at least one of the base units with respect to the target space has to emit the counter waves with the similar or same amplitudes as the harmful waves. When the EMC display includes multiple counter units, all of its counter units may be disposed in similar distances from at least one of the base units and/or target space or, alternatively, at least two of the counter units may be disposed in different distances from at least one of the base units and/or target space. In addition to the distances and/or dispositions thereof, the counter waves may have various intensities depending upon whether the counter waves counter the harmful waves throughout an entire portion of the target space or only in preset positions inside such a target space. For example, the counter unit preferably emits such counter waves capable of countering the harmful waves throughout the target space as the user may be situated anywhere therein. When the user is to be situated only in preset positions of the target space, however, the counter may then be shaped, sized, arranged, and disposed to emit the counter waves which best counter the harmful waves only in such positions but not with such an efficiency in other positions of the target space.

Once the counter unit is arranged to emit the counter waves defining proper phase angles and amplitudes, such a counter unit may be shaped, sized, arranged, and disposed in order to counter the harmful waves depending on detailed countering mechanisms.

In one example, the counter unit may be shaped, sized, and/or arranged similar (or identical) to at least one of such base units, where such a mechanism is to be referred to as a "source matching" hereinafter. The basic concept of the "source matching" is that the counter unit may emit the counter waves defining wavefronts similar to its configuration (i.e., its shape, size, and/or arrangement), that wavefronts of such counter waves may automatically match wavefronts of the harmful waves, and that the counter waves counter the harmful waves due to the similarity between the configurations of the counter unit and at least one of such base units. When the system includes multiple base units, a single counter unit may then be arranged to emit the counter waves capable of countering the harmful waves irradiated by one of the base units or, alternatively, capable of countering a sum of the harmful waves irradiated by all (or at least two but all) of such base units. When the system includes multiple counter units, the counter units may emit the counter waves capable of countering the harmful waves irradiated by a single base unit or multiple base units. When the system includes multiple counter units and multiple base units, the counter waves emitted by each counter unit may also counter the harmful waves irradiated by each base unit, a sum of the counter waves emitted by at least two counter units may counter the harmful waves irradiated by one of the base units, the counter waves emitted by a single counter unit may counter a sum the harmful waves irradiated by at least two base units, a sum of the counter waves from all of the counter units may counter a sum of the harmful waves irradiated by all (or at least two but not all) of the base units, and so on. It is preferred in this "source matching" that the counter unit emit the counter waves defining the wavefronts with a configuration (or pattern) similar to the configuration (or pattern) of itself. However, it is also possible that the counter unit emits the counter waves defining the wavefronts with a configuration (or pattern) different from that of the counter unit, that the wavefronts of a sum of the counter waves emitted by multiple counter units may form the configuration different from that of each counter unit and/or define the arrangement different from that of multiple counter units, as long as the counter waves may effectively counter the harmful waves in the target space.

In another example, the counter unit may be disposed (i.e., oriented, aligned, and/or positioned) in a manner that at least one wavefront of such counter waves may match at least one wavefront of the harmful waves, where this mechanism is to be referred to as a "wave matching" hereinafter. The basic concept of the "wave matching" lies in the fact that the counter waves may counter the harmful waves when the counter unit is incorporated in a disposition to match the wavefronts of the counter waves with the wavefronts of the harmful waves as far as the configuration of the counter unit may be properly manipulated in order to operate on such "wave matching." When the EMC display system includes multiple base units, a single counter unit may be arranged to emit the counter waves which are capable of matching and countering the harmful waves irradiated by only one of the base units or, alternatively, matching and countering a sum of the harmful waves irradiated by all (or at least two but not all) of the base units. When the system includes multiple counter units, the counter units may emit the counter waves capable of countering the harmful waves irradiated by a single base unit or all (or at least two but not all) of the base units. When the system includes multiple counter units and multiple base units, the counter waves emitted by each counter unit may counter the harmful waves irradiated by each base unit, a sum of the counter waves emitted by at least two counter units may counter the harmful waves irradiated by one of the base units, the counter waves from a single counter unit may counter a sum the harmful waves irradiated by at least two base units, a sum of the counter waves emitted by all of the counter units may then counter a sum of the harmful waves irradiated by all of the base units, and the like, as long as at least a portion of at least one of such wavefronts of the counter waves may match and then counter at least a portion of at least one of the wavefronts of the harmful waves in the target space.

Various counter units constructed based on the source matching and/or wave matching are to be disclosed hereinafter. It is appreciated in the source matching that there does not exist any one-to-one correlations between the configuration of such a counter unit and the configuration of the counter waves emitted thereby. That is, the counter waves of certain configuration (or wave characteristics) may be obtained by a single counter unit which defines a certain shape and size and is provided in a certain arrangement, by another counter unit which defines a similar shape and size but is provided in another arrangement, by another counter unit which has a different shape and size but is provided in a similar arrangement, by at least two counter units defining preset shapes and sizes and provided in a preset arrangement, by the same number of counter units defining different shapes and/or sizes or in a different arrangement, by a different number of counter units defining similar shapes and/or sizes or in a similar arrangement. It is similarly appreciated in the above wave matching that there does not exist an one-to-one correlation between the disposition of the counter unit and the wavefronts of the counter waves emitted by the counter unit. In other words, the wavefronts with certain shapes may be obtained by a single counter unit which defines a certain configuration and is disposed in a certain position with respect to at least one of such base units and/or target space, by another single counter unit defining another configuration and also disposed in another position, by at least two counter units defining preset configurations and disposed in preset positions, by the same number of counter units defining different configurations and disposed in different positions, by a different number of counter units defining different configurations and disposed in different positions, and the like. Therefore, It is appreciated that such counter units may be embodied in many other different forms and should not be limited to following aspects and/or their embodiments which are to be set forth herein. Rather, various exemplary aspects and/or embodiments described herein are provided so that this disclosure will be thorough and complete, and fully convey the scope of the present invention to one of ordinary skill in the relevant art.

In another aspect of the present invention, a single generic counter unit may be provided for a single generic base unit to counter the harmful waves from the base unit by the counter waves from the counter unit. FIGS. 2A to 2F show top schematic views of exemplary electromagnetic countering mechanisms in each of which a single counter unit emits the counter waves capable of countering the harmful waves which are irradiated from a single base unit of a single wave source according to the present invention, where the base unit is a point source in FIGS. 2A to 2C and 2F, while the base unit is an elongated source in FIGS. 2D and 2E. It is appreciated that these figures, however, may also be interpreted in different perspectives. For example, such figures may be interpreted as the top cross-sectional views, where the base units of FIGS. 2A to 2C and 2F are wires extending perpendicular to the sheet, and the base units of FIGS. 2D and 2E are strips or rectangular rods also extending normal to the sheet. In another example, the figures may be interpreted as sectional views of more complex articles, where the base units of FIGS. 2A to 2C and 2F may correspond to sections of coils, spirals, meshes, and the like, while the base units of FIGS. 2D and 2E may similarly correspond to sections of curvilinear rods or strips. It is also appreciated in these figures that such base units are enclosed in the wave sources which may be cases or other parts of such a system which do not irradiate such harmful waves. It is further appreciated in all of these figures that the EMC systems are disposed in such a way that the target space is formed to the right side of the counter and base units.

Figure 2A:
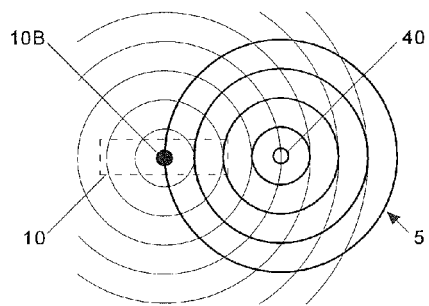
FIGS. 2A to 2F are top schematic views of exemplary electromagnetic countering mechanisms in each of which a single counter unit emits counter waves to counter harmful waves irradiated by a single base unit of a single wave source according to the present invention.
Figure 2D:
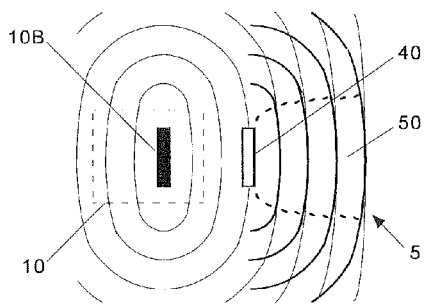

In one exemplary embodiment of such an aspect of the invention and as described in FIG. 2A, an EMC system 5 includes a single rectangular wave source 10 and a single counter unit 40, where the source 10 includes therein a single base unit 10B defining a shape of a point source. The counter unit 40 is similarly shaped as another point source and disposed to the right side of the base unit 10B. In this arrangement, the counter unit 40 emits the counter waves of which wavefronts are identical to those of the harmful waves irradiated by the base unit 10B. Because the counter unit 40 is disposed closer to a hypothetical target space on the right side of the figure, such counter wavefronts always define radii of curvature smaller than those of the harmful wavefronts. Accordingly, the counter unit 40 may counter (i.e., cancel or suppress) the harmful waves only along a line connecting the counter and base units 40, 10B or in its vicinity. It is appreciated that such an embodiment corresponds to the source matching which turns out to be ineffective due to a discrepancy in the radii of curvature of the wavefronts of the counter and harmful waves.

Figure 2B:
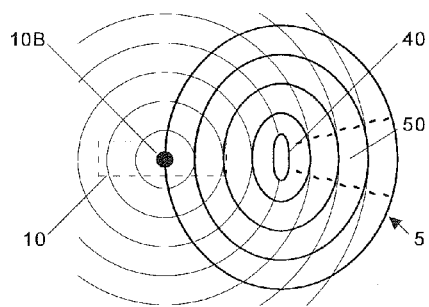
Figure 2E:
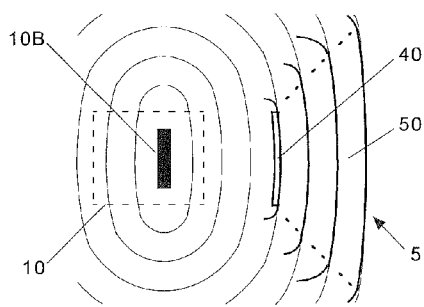

In another exemplary embodiment of this aspect of the invention and as depicted in FIG. 2B, an EMC system 5 includes a single counter unit 40 and a single rectangular wave source 10 with a single base unit 10B disposed therein. The base unit 10B is similar to that of FIG. 2A, however, the counter unit 40 is elongated, oriented vertically along its length, and disposed on the right side of the base unit 10B. Due to its elongated shape, the counter unit 40 emits the counter waves whose wavefronts are also elongated vertically and, therefore, define the radii of curvature which are greater than those of FIG. 2A and which match those of the harmful waves. Accordingly, such a counter unit 40 defines a target space 50 across which the counter waves counter the harmful waves to a preset extent. It is to be understood that such an embodiment corresponds to the wave matching mechanism in that the counter unit 40 is shaped similar to one of the harmful wavefronts.

Figure 2C:
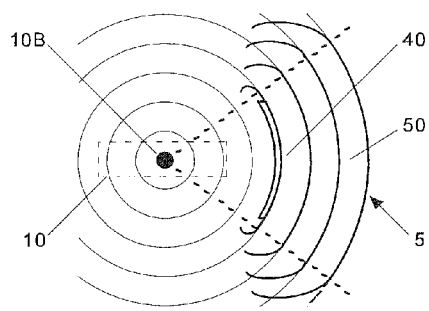

In another exemplary embodiment of this aspect of the invention and as depicted in FIG. 2C, an EMC system 5 includes a single counter unit 40 and a single rectangular wave source 10 with a single base unit 10B disposed therein. The base unit 10B is similar to that of FIG. 2A, however, the counter unit 40 is shaped and sized to conform to one wavefront of such harmful waves. That is, the counter unit 40 is shaped as an arc and disposed in an orientation concave to the right side of the figure or to the target space 50. Because of its arcuate shape, such a counter unit 40 emits the counter waves of which wavefronts are also arcuate and, therefore, define the radii of curvature which are similar or identical to those of the harmful waves. Therefore, the counter unit 40 defines a target space 50 across which the counter waves counter the harmful waves to a preset extent. It is appreciated that such an embodiment corresponds to another wave matching mechanism and that the counter waves emitted form this arcuate counter unit 40 better match such harmful wavefronts and define the target space 50 which expands over a wider angle around the base unit 10B than those of FIGS. 2A and 2B.

In another exemplary embodiment of this aspect of the invention and as depicted in FIG. 2D, an EMC system 5 includes a single counter unit 40 and a single rectangular wave source 10 with a single base unit 10B. Contrary to those of the above, this base unit 10B is rectangular and oriented vertically along its length or its long axis, and irradiates the harmful waves of which wavefronts define vertical and relatively straight portions which are attributed to the length or long axis of the base unit 10B. The counter unit 40 is shaped and sized similar or identical to the base unit 10B, and disposed in the same orientation as the base unit 10B. This orientation may be viewed to dispose the counter unit 40 along the vertical straight portions of the wavefronts of the harmful waves. The counter unit 40 also emits the counter waves whose wavefronts define vertical and relatively straight portions, similarly due to the length or long axis thereof. Because such portions of the counter wavefronts match those of the harmful wavefronts, the counter unit 40 forms the target space 40 to the right side. This embodiment corresponds to the source matching, wave matching or their combination. It is to be understood that the counter unit of FIG. 2A is shaped and sized as the base unit but ineffective due to a discrepancy in the radii of curvature between the wavefronts of the counter and source waves. The counter unit 40 of this embodiment is similarly shaped and sized as the base unit 10B but efficiently counter such harmful waves in the target space 50. The primary reason of this countering lies in the fact that both of the harmful and counter waves define along their wavefronts the vertical straight portions which generally do not depend upon the radii of curvature thereof. Otherwise, configuring the counter unit 40 similar to the base unit 10B and then disposing such a counter unit 10 between the base unit 10B and target space generally do not provide an efficient countering, where further details of this front arrangement are to be provided below. It is appreciated that such an embodiment corresponds to the source matching in which the counter unit 40 is shaped, sized, and/or arranged similar (or identical) to the base unit 10B.

In another exemplary embodiment of this aspect of the invention and as depicted in FIG. 2E, an EMC system 5 includes a single counter unit 40 and a single rectangular wave source 10 with a single base unit 10B which is similar to that shown in FIG. 2D. The counter unit 40, however, is shaped and sized to conform to one wavefront of such harmful waves. Similar to that of FIG. 2C, the counter unit 40 is shaped as an arc and disposed in an orientation concave to the right side of the figure or target space 50. Because of its arcuate shape, such a counter unit 40 emits such counter waves of which wavefronts are also arcuate and, therefore, define the radii of curvature which are similar or identical to those of the harmful waves, not only along their vertical straight portions but also along their curved portions, mainly due to the arcuate shape of the counter unit 40. Accordingly, such a counter unit 40 defines a target space 50 which also expands over a wide angle therearound and across which the counter waves effectively counter such harmful waves. It is to be understood that this embodiment corresponds to another wave matching mechanism.

Figure 2F:
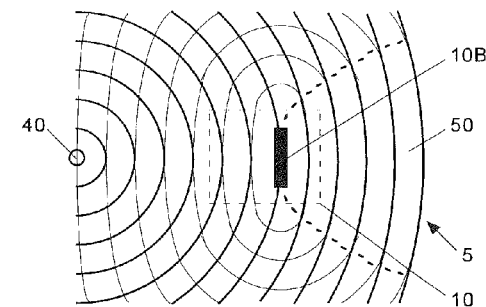

In another exemplary embodiment of this aspect of the invention and as depicted in FIG. 2F, an EMC system 5 includes a single counter unit 40 and a single rectangular wave source 10 which has a single base unit 10B therein. Both of the counter and base units 40, 10B are identical to those of FIG. 2A. However, the counter unit 40 is disposed on an opposite side of a target space 50 with respect to the base unit 10B and aligned with the base unit 10B as are the cases with the preceding figures. In this arrangement, the counter unit 40 emits the counter waves of which wavefronts are identical to those of the harmful waves irradiated by the base unit 10B. Because the counter unit 40 is disposed farther away from the target space 50, such counter wavefronts define the radii of curvature which approach and then match those of the harmful wavefronts when disposed at a proper distance from the base unit 10B. Accordingly, the counter unit 40 disposed in this rear arrangement may effectively counter the harmful waves and defines the target space 50 expanding over a wide angle around the base unit 10B. It is appreciated that the sole difference between the counter units of FIGS. 2A and 2F is their dispositions, i.e., one disposed in the "front arrangement" of FIG. 2A and another disposed in the "rear arrangement" of FIG. 2F. It is also appreciated that the rear arrangement is not necessarily superior to the front arrangement and that further details of selecting the proper arrangement are to be provided below. It is further appreciated that this embodiment corresponds to the wave matching in which the counter unit 40 is disposed at the position for matching the harmful wavefronts with the counter wavefronts.

Although not included in the figures, a single counter unit may be disposed in an arrangement flush with the base unit with respect to the target space, flush with a direction of propagation of the harmful waves, flush with another direction along which electric current flows in the base or counter unit, flush with another direction in which electric voltage is applied across the base or counter units, and so on. In this "lateral" arrangement, the radii of curvature of the counter wavefronts automatically match those of the harmful wavefronts and, therefore, the counter waves effectively match and then counter the harmful waves in the target space. For this arrangement, however, the wave source has to provide a space in which the counter unit may be incorporated. Therefore, the counter unit may be implemented inside the wave source and close to the base unit thereof when applicable. Otherwise, the counter unit may instead be disposed over, below or beside the wave source and as close to the base unit as possible. It is appreciated, however, that the counter unit disposed next to the base unit may propagate the counter waves onto the base unit and obstruct normal operation of the base unit. Accordingly, the lateral arrangement is preferably selected only when such an arrangement may not obstruct the normal operation of the base unit, wave source including such or EMC system including such. When the lateral arrangement does not affect the operation of the base unit but the counter unit may not be disposed close to the base unit due to space limitations, two or more counter units may be disposed on opposing sides (e.g., left and right, top and bottom, front and rear, and the like) of such a base unit and as close to the base unit as possible. Such counter units may also be arranged to emit the counter waves a sum of which may be symmetric or skewed toward a preset direction based on the wave characteristics of the harmful waves.

In another aspect of the present invention, multiple generic counter unit may be provided for a single generic base unit for countering the harmful waves irradiated by the base unit with the counter waves emitted by all of such counter units or emitted by at least two but not all of such counter units. FIGS. 2G to 2L are top schematic views of exemplary electromagnetic countering mechanisms in each of which multiple counter units emit counter waves to counter harmful waves irradiated from a single base unit of a single wave source according to the present invention, where the base unit is a point source in FIGS. 2G to 2K, while the base unit is an elongated source in FIG. 2L. It is appreciated that these figures, however, may also be interpreted in different perspectives. For example, such figures may be viewed as the top cross-sectional views, where the base units of FIGS. 2G to 2K are wires extending perpendicular to the sheet, and the base unit of FIG. 2L is a strip or a rectangular rod also extending normal to the sheet. In another example, the figures may be interpreted as sectional views of more complex articles, where the base units of FIGS. 2G to 2K may correspond to sections of coils, spirals, meshes, and the like, whereas the base unit of FIG. 2L may similarly correspond to sections of curvilinear rods or strips. It is also appreciated in these figures that such base units are enclosed in the wave sources which may be cases or other parts of such a system which do not irradiate such harmful waves. It is further appreciated in all of these figures that the EMC systems are disposed in such a way that the target space is formed to the right side of the counter and base units.

Figure 2G:
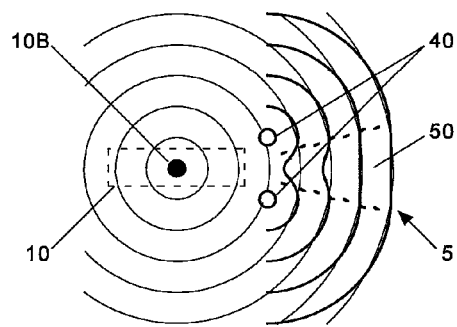
FIGS. 2G to 2L are top schematic views of exemplary electromagnetic countering mechanisms in each of which multiple counter units emit counter waves to counter harmful waves irradiated by a single base unit of a single wave source according to the present invention.
Figure 2J:
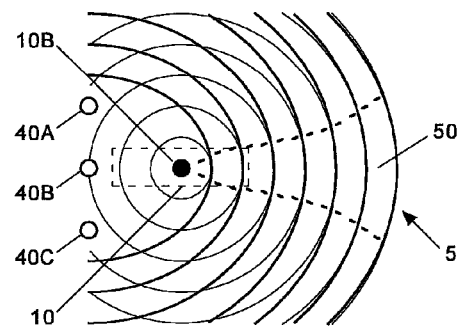

In one exemplary embodiment of such an aspect of the invention and as described in FIG. 2G, an EMC system 5 includes two counter units 40 and a single wave source 10 including a single base unit 10B. The base unit 10B is similar to those of FIGS. 2A to 2C, while a pair of counter units 40 are disposed between the base Ni 10B and a target space 50. Such counter units 40 are also disposed symmetric to the base unit 10B and flush with each other with respect thereto, i.e., the counter units 40 are disposed at an equal distance from the base unit 10B and/or target space 50. Such counter units 40 are arranged to emit the counter waves of the same phase angles so that the wavefronts of the counter waves from each counter unit 40 are superposed onto each other while increasing their amplitudes. As the counter waves propagate, their wavefronts which correspond to a sum of each set of wavefronts from each counter unit 40 increase their radii of curvature as if they are emitted by the elongated counter units of FIGS. 2B to 2E. Therefore, the counter wavefronts match the harmful wavefronts, and the pair of counter units 40 match and counter the base unit 10B while defining the target space 50 expanding over a limited angle therearound. It is to be understood that disposing two or more counter units 40 result in flattening the wavefronts of the counter waves and increasing the radii of curvature of the superposed portions of the counter wavefronts. It is further appreciated that this arrangement corresponds to the wave matching in which multiple counter units 40 are disposed along one wavefront of the harmful waves.

Figure 2H:
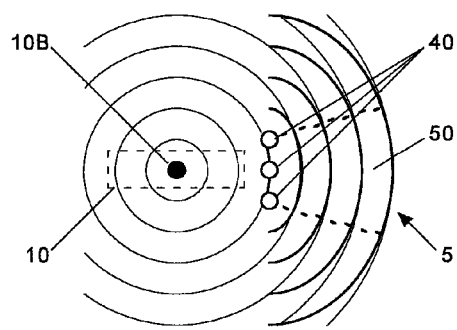
Figure 2K:
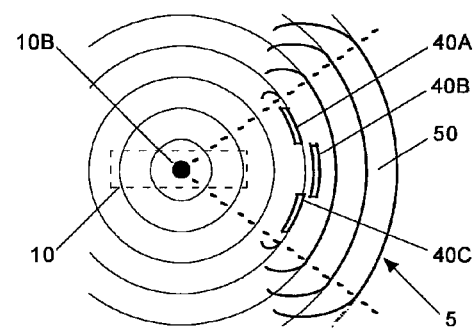

In another exemplary embodiment of this aspect of the invention and as depicted in FIG. 2H, an EMC system 5 includes three counter units 40 and a single wave source 10 enclosing therein a single base unit 10B. The base unit 10B is similar to those of FIGS. 2A to 2C, while the counter units 40 are similar to those of FIG. 2G such that all counter units 40 are disposed between the base unit 10B and target space 50 and flush with the base unit 10B. However, the system 5 includes one more counter unit 40 so that an array of three counter units 40 approximate the wavefronts of such harmful waves better than those of FIG. 2G. Accordingly, the counter units 40 emit the counter waves which better counter the base unit 10B and define the target space 50 expanding over a wider angle therearound than those of FIG. 2G. It is appreciated that disposing three counter units 40 result in further flattening the superposed wavefronts of the counter waves and also result in increasing the radii of curvature of such portions of the wavefronts of the counter waves. It is also appreciated that this arrangement is another wave matching where all three counter units 40 are disposed along one wavefront of the harmful waves.

Figure 2I:
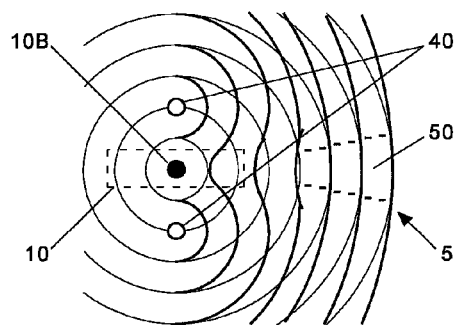
Figure 2L:
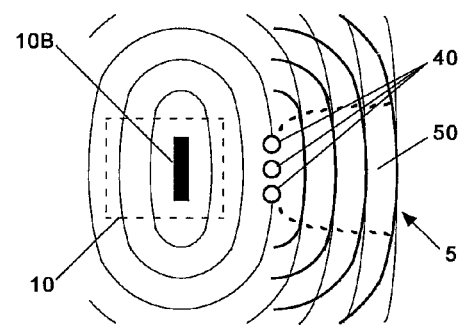

In another exemplary embodiment of this aspect of the invention and as depicted in FIG. 2I, an EMC system 5 includes two counter units 40 and a single wave source 10 including a single base unit 10B which is similar to those of FIGS. 2A to 2C. Two counter units 40 are disposed on opposite sides of the base unit 10B at an equal distance therefrom and also flush with the base unit 10B with respect to a target space 50. Similar to those of all of the preceding embodiments, such counter units 40 emit the counter waves defining the similar or identical phase angles so that the counter waves emitted by each of such counter units 40 superpose onto each other for not only increasing their amplitudes but also flattening the superposed portions of their wavefronts while increasing the radii of curvature of such wavefronts. Accordingly, the counter units 40 counter the harmful waves and define the target space 50 spanning around a rather limited angle therearound. It is appreciated that this arrangement is rather the source matching than the wave matching in that the counter units 40 are disposed in the symmetric arrangement and effect the elongated counter unit arranged flush with the base unit 10B.

In another exemplary embodiment of this aspect of the invention and as depicted in FIG. 2J, an EMC system 5 includes three counter units 40 and a single wave source 10 enclosing therein a single base unit 10B which is similar to those of FIGS. 2A to 2F. Contrary to those of FIG. 2H, three counter units 40 are disposed on an opposite side of a target space 50 with respect to the base unit 10B. The counter units 40 are arranged flush with each other relative to the base unit 10B and target space 50 and also spaced away from each other at an equal distance. Similar to those of FIGS. 2G to 2I, both of outer counter units 40A, 40C are arranged to emit the counter waves defining the phase angles at least partially opposite to those of the harmful waves so that superposed portions of the wavefronts of the counter waves are flattened while increasing their radii of curvature. Contrary to those of the preceding figures, a middle counter unit 40B is arranged to emit the counter waves defining the phase angles which are at least partially similar to those of such harmful waves and opposite to those of the counter waves emitted by the outer counter units 40A, 40C. Therefore, a net effect of incorporating the middle counter unit 40B is to sharpen the curvature of the superposed portions of the wavefronts of a sum of the counter waves and to define the target space 50 expanding around a narrower angle around the base unit 10B, as manifest in a comparison between the target spaces 50 of FIGS. 2F and 2J. That is, by incorporating multiple counter units 40A-40C emitting the counter waves of the phase angles opposite to each other, it is feasible to precisely manipulate the wavefronts of the sum of such counter waves and their radii of curvature for better matching the wavefronts of the harmful waves. It is appreciated that such an embodiment may corresponds to the source matching, wave matching or a combination thereof.

The counter units 40A-40C of this embodiment may be incorporated in different arrangements. For example, only two counter units may be included to emit the counter waves with opposite phase angles, where resulting wavefronts of the sum of the counter waves are not symmetric but skewed to one or an opposite side. In addition, the distances between the counter units may be manipulated to adjust the wavefronts of a sum of the counter waves regardless of the number of the counter units. Moreover, the counter units emitting the counter waves defining the phase angles similar to those of the harmful waves may be employed as the outer units to further sharpen the superposed portions of the counter waves.

In another exemplary embodiment of this aspect of the invention and as depicted in FIG. 2K, an EMC system 5 includes three counter units 40 and a single wave source 10 enclosing therein a single base unit 10B which is similar to those of FIGS. 2A to 2C. The counter units 40A-40C are also similar to those of FIG. 2H so that all of such counter units 40A-40C are disposed between the base unit 10B and target space 50 and similar to each other, that the counter units 40A-40C emit the counter waves of the same or similar phase angles, and so on. However, each counter unit 40A-40C is arranged to form an arcuate article shaped and sized to match a portion of a wavefront of the counter waves. In addition, both of upper and lower counter units 40A, 40C are spaced away from each other and also disposed along one wavefront of the harmful waves, whereas a middle counter unit 40B is disposed between the upper and lower counter units 40A, 40C and along an adjacent wavefront of the harmful waves in such a manner that superposed portions of the wavefronts of a sum of the counter waves are flattened while defining larger radii of curvature and match the wavefronts of the harmful waves, thereby forming a target space 50 which expands over a wide angle around the base unit 10B. It is to be understood that this arrangement is another wave matching where all three counter units 40A-40C are disposed along multiple wavefront of the harmful waves.

In another exemplary embodiment of this aspect of the invention and as depicted in FIG. 2L, an EMC system 5 includes three counter units 40 and a single wave source 10 enclosing therein a single base unit 10B. While the base unit 10B is similar to those of FIGS. 2D and 2E, the counter units 40 are similar to those of FIG. 2H and emit the counter waves which are flattened and define vertical straight portions therealong. Therefore, the counter waves match the vertical straight portions of the harmful waves and define a target space 50 similar to that of FIG. 2D. It is appreciated that this embodiment is another source matching in which three counter units 40 approximate the elongated base unit 10B.

In another aspect of the present invention, a single generic counter unit may also be provided for multiple generic base units for countering the harmful waves from such base units by the counter waves from the counter unit. In one example, such a counter unit may be arranged to counter a sum of the harmful waves irradiated by each base units, where detailed disposition of the counter unit may depend upon configurations and/or dispositions of the base units, amplitudes and/or directions of the harmful waves irradiated by such base units, and the like. Based thereupon, the counter unit may be disposed symmetrically to all or at least some of the base units, may be incorporated in the front, rear or lateral arrangement, and the like, where such arrangements are generally referred to an "global or overall countering" hereinafter. In another example, the counter unit is rather arranged to counter the harmful waves irradiated by only one of multiple base units, where such an arrangement is generally referred to as "local or individual countering" hereinafter. This local countering may only be effective when other uncountered base units irradiate negligible amounts of such harmful waves, when other uncountered base units irradiate non-negligible amounts of the harmful waves to other directions than the target space, and the like. Otherwise, it is preferred to manipulate the counter unit to counter the harmful waves of the uncountered base units, to include additional counter units for countering those harmful waves, and the like.

It is appreciated that various countering mechanisms described hereinabove for a single base unit may equally be applied to the system with multiple base units in the global countering mechanism. That is, the above countering mechanisms may be applied not to such harmful waves irradiated by the single base unit but to a sum of the harmful waves irradiated by multiple base units. When the system is to operate in the local countering mechanism, the aforementioned mechanisms may also be applied to each of multiple base units regardless of an exact number of such base units.

In another aspect of the present invention, multiple counter units may be provided for multiple base units for countering the harmful waves irradiated from such base units with the counter waves emitted by the counter units. In one example, multiple counter units are provided in the same number as the base units and each counter unit is arranged to counter only one of such base units in the local countering mechanism. Alternatively, at least one of such counter units may counter only one of such base units in the local countering mechanism, whereas at least one another of such counter units may counter at least two of the base units in the global countering mechanism. In another example, a less number of counter units are provided so that each counter unit is arranged to counter at least two of the base units in the global countering mechanism, that at least one of the counter units counters one of such base units in the local countering mechanism while at least one another of such counter units counters at least two of such base units in the global countering mechanism, and the like. In another example, a greater number of counter units are provided so that each base unit may be countered by at least two of the counter units, that at least one of the counter units counters one of the base units in the local countering mechanism while at least one another of the counter units may counter at least two of such base units in the global countering mechanism, and so on. In all of these examples, any of the above front, rear, and lateral countering mechanisms may be used by the counter units, where such countering mechanisms may be same or different for each counter unit.

Configurational and/or operational variations of such EMC systems and their counter units as well as configurational and/or operational modifications of such EMC systems and their counter units as exemplified in FIGS. 2A to 2L and/or as disclosed hereinabove without any accompanying figures also fall within the scope of the present invention.

As described above, a typical EMC system includes at least one wave source and at least one counter unit, where the wave source includes or encloses therein at least one of the base units and where the counter unit may include at least one optional electric connector such as a lead wire and at least one optional coupler for coupling the counter unit to other parts of the system. The EMC system may include at least one body which encloses at least a portion of the base units, at least a portion of the counter unit, and the like. Alternatively, an entire portion of the counter and/or at least one of such base units may be exposed with or without such a body.

More specifically, the counter unit consists of various parts such as at least one body, at least one optional support, and at least one insert. The body of the counter unit qualitatively corresponds to the base unit of the wave source in that such a body is the sole component of the counter unit which emits the counter waves when the electric current flows therein, when the electric voltage is applied thereacross, and the like. Therefore, such a body may preferably be made of and/or include at least one electric conductor when the electric current is to flow therein, may be made of and/or include any electrically conductive, semiconductive or insulative material when the electric voltage is to be applied thereacross, and the like. The support serves to mechanically support the above body and/or retain such a body therein for mechanical protection and/or electrical isolation. The insert is typically used to augment amplitudes of the counter waves, particularly when the counter unit includes at least one coil of conductive wire into which such an insert is disposed. The insert may be made of and/or include various magnetic materials such as, e.g., ferromagnetic materials, paramagnetic materials, diamagnetic materials, and ferrimagnetic materials, where the ferromagnetic materials are the preferred ones. It is appreciated that the counter unit is generally arranged to maintain its configuration while emitting such counter waves, where this fixed configuration may be embodied by defining the body of the counter unit of rigid materials, by fixedly coupling the body of the counter unit to the support, and so on. In the alternative, the counter unit may be arranged to change its shape while emitting such counter waves, where this variable configuration may be embodied by defining the body of the counter unit of elastic or deformable materials, by movably coupling the body of the counter unit to the support, and the like. It is appreciated that the counter unit emitting such counter waves is to be opposed by at least one of the base units irradiating the harmful waves of an opposite magnetic polarity. Therefore, the counter unit tends to move while emitting the counter waves, where a special provision may also have to be implemented when it is desirable to fix the counter unit during its wave-emitting operation.

The counter may be provided in various configurations which typically refer to shapes, sizes, arrangements, and the like. In general, the configuration of the counter unit depends upon the above countering modes (such as, e.g., the source or wave matching) and/or countering mechanisms (such as, e.g., the front, rear or lateral arrangement, local or global matching, and the like), which generally depend on the configurational characteristics of at least one of such base units, wave characteristics of the harmful waves, and the like. In addition, the configuration of the counter unit depends upon the shapes, sizes, orientation, and/or dispositions of the target space which are to be formed on one side of and/or around the counter unit.

The shape of the counter unit may also be arranged to be identical (or similar) to the shape of at least one of the base units, where the counter unit is to be constructed to emit the counter waves which match the harmful waves automatically. The shape of the counter unit may be arranged to be different from the shape of at least one of the base units as well, where such a counter unit may be provided in other shapes, may be wound around at least one of the base units, may enclose therein at least a portion of at least one of such base units, may be enclosed by at least a portion of at least one of the base units, and the like. The counter unit may define a shape of a wire, a strip, a sheet, a tube, a coil thereof, a spiral thereof, and/or a mesh thereof, may form a combination of two or more of such shapes without defining any holes or openings therethrough, may define an array of two of more of such shapes while defining multiple holes and/or openings therethrough, and the like, where examples of the combinations and/or arrays may include, but not be limited to, a bundle including multiple identical or different shapes bundling each other, a braid of multiple identical or different shapes braided along each other, and the like. The counter unit may also be made of a mixture which includes at least two materials and which are also provided in any of the above shapes, combinations, and/or arrays. It is appreciated that the coil (including a solenoid or a toroid), the spiral, the mesh, and the arrays thereof may be particularly useful in the wave matching as will be described below. It is also appreciated that all of multiple counter units may define the same shape or that at least two but not all of such counter units may define the same shape. In the alternative, each counter unit may define a different shape.

The counter unit may further be shaped to conform to at least one of the base units so that the counter waves emitted from the counter unit better match the harmful waves, where the counter unit may conform to the at least one of the base units while approximating such or providing further details thereto. Alternatively, the counter unit may be shaped to not conform to at least one of the base units while manipulating such counter waves to match the harmful waves. This arrangement may be used when a single counter unit counters multiple base units or when multiple counter units counter a single base unit. It is appreciated in this arrangement that the counter unit(s) may receive desirable electrical energy (e.g., current and/or voltage) to emit such counter waves capable of matching and countering the harmful waves in the target space. It is also appreciated that all of the counter units may conform to a single base unit, to at least two but not all of multiple base units, or to each (or all) of multiple base units, that at least two but not all of the counter units may conform to a single base unit, to at least two but not all of multiple base units, or to each (or all) of multiple base units, and so on. In the alternative, all of the counter units may not conform to any of the base units.

When at least one counter unit is shaped similar (or identical) to at least one base unit, such a counter unit is preferably arranged to approximate a single base unit, at least two but not all of multiple base units or all of the base units. When the base unit forms a three-dimensional (or 3-D) shape, the counter unit may be provided as a three-dimensional analog of a similar and/or simpler shape, a two-dimensional (or 2-D) analog or an one-dimensional (or 1-D) analog. When the base unit defines a 2-D shape, the counter unit may be formed as a 2-D analog of a similar or simpler shape or an 1-D analog. When the base unit forms an 1-D shape, the counter unit may be provided as another 1-D analog of a similar or simpler shape. When a single counter unit is to counter multiple base units, the counter unit may approximate only one major base unit as one of the analogs, may approximate at least two of the base units into one of such analogs, and the like. When multiple counter units are to counter a single base unit, each counter unit may approximate only a portion of the base unit or may redundantly form the analog of such a base unit. When multiple counter units are to counter multiple counter units, such counter units may also approximate the base units into the analogs of the same dimension or different dimensions. It is appreciated that those analogs conform to the base units and, accordingly, that such analogs may define rather straight or curved shapes depending upon the shapes of the base units. It is also appreciated that such analogs preferably maintain similarity with at least one of the base units, where the similarity is maintained in terms of lengths of the counter and/or base units, widths thereof, heights thereof, thicknesses thereof, diameters or radii thereof, radii of curvature thereof, numbers of revolutions or turns thereof, ratios of such lengths, ratios of such widths, ratios of such thicknesses or heights, ratios of such diameters or radii, ratios of such numbers, and the like. When a single base unit is countered by a single counter unit, such configurational parameters are defined in each of the base and counter units. When a single counter unit counters multiple base units, such configurational parameters are defined in the counter unit, in an array of all of such base units, in an array of at least two but not all of such base units, and the like. When multiple counter units counter a single base unit, such configurational parameters are defined in the base unit, in an array of all of the counter units, in an array of at least two but not all of the counter units, and the like. When multiple counter units are to counter the same or different number of base units, such configurational parameters are also defined individually or in arrays as described above.

When a single counter unit or multiple counter units are shaped similar (or identical) to a single base unit or multiple base units, the counter units may be arranged to provide details to at least one of the base units, not in the sense of adding structures not present in the base units but in the context of streamlining or smoothening the wavefronts of the counter waves to better match the wavefronts of such counter waves with those of the harmful waves. For example, a single or multiple small counter units may be disposed around (or inside) one or multiple major counter units for streamlining outer (or inner) edges of the wavefronts of a sum of the counter waves emitted by the major counter units. In another example, a single or multiple small counter units may be disposed closer to (or farther away from) one or multiple major counter units to manipulate radii of curvature of the wavefronts of a sum of the counter waves emitted by the major counter units. These small or minor counter units may be disposed in various relations to one or more major counter units for other purposes as well, as far as incorporation of the minor counter units may improve such matching between the counter and harmful waves in the target space. Therefore, when the system includes multiple counter units, at least one (or all, at least two but not all) of the counter units may be arranged to approximate at least one (or all, at least two but not all) of such base units, at least one (or all, at least two but not all) of the counter units may also be arranged to provide details to at least one (or all, at least two but not all) of the base units, and the like.

The counter unit may be arranged to form various cross-sections along a longitudinal (or long) axis thereof, its short axis which may be perpendicular or otherwise transverse to the long axis, and the like. In one example, the counter unit is arranged to define an uniform cross-section along at least one of such axes so that the counter waves emitted thereby also define the wavefronts defining the same shapes along one of such axes. In another example, the counter unit may be provided to vary its cross-section along at least one of such axes so that the counter waves emitted therefrom define the wavefronts varying their shapes along at least one of such axes. When the system has multiple counter units, all of such units may define the same shape or at least two of such counter units may define different shapes.

The counter unit may be arranged to define various sizes while emitting the counter waves of proper amplitudes capable of effectively countering the harmful waves. For example, the counter unit disposed in the front arrangement may define a size smaller than that of at least one of the base units due to its closer disposition to the target space. In contrary, another counter unit disposed in the rear arrangement may instead have a size larger than that of at least one of the base units due to a greater distance to the target space. However, the size of the counter unit may be decided by other factors such as, e.g., the shape of the counter unit, amplitudes of electric energy (i.e., current and/or voltage) supplied thereto, and the like. Accordingly, the counter unit in the front arrangement may define a size larger than that of at least one of such base units while emitting a less amount of the counter waves per its unit area, while the counter unit in the rear arrangement may have a size smaller than that of at least one of the base units while emitting a greater amount of the counter waves per its unit area, and the like. That is, the size of the counter unit may be deemed as a secondary parameter which may be decided by other factors such as, e.g., the shape of the counter unit, amplitudes of the electric energy supplied thereto, distances to at least one of the base units and/or target space, arrangement of such counter unit(s), orientation thereof, and the like.

The counter unit may also be arranged to have various sizes along its longitudinal and/or short axes. In one example, the counter unit is arranged to form an uniform size along the long and/or axes such that the counter waves emitted thereby form the wavefronts of the same shapes along the long and/or short axes when the same amount of the energy is supplied thereto. In another example, such a counter unit may be provided to vary its size along the long and/or short axes such that the counter waves emitted thereby form the wavefronts varying their shapes along one of such axes. In addition, the counter unit may maintain the same size along the long and/or short axes while varying its shape therealong. When the system includes multiple counter units, such counter units may define the same size or at least two of such units may define different sizes.

Multiple counter units may be incorporated in various arrangements, where such counter units are arranged to emit the counter waves capable of automatically matching the harmful waves due to such an arrangement. In one example, the counter units may be in an arrangement conforming to the shape of a single base unit or conforming to an arrangement of multiple base units so that the counter waves match the harmful waves in the target space. In another example, the counter units may be in an arrangement which may not conform to the shape of the single base unit or to the arrangement of multiple base units. These arrangements may be embodied when multiple counter units are to counter a single base unit or when multiple counter units counter a different number of multiple base units. It is to be understood in these arrangements that the counter units may receive the electrical energy (e.g., current and/or voltage) to emit the counter waves which are capable of matching and countering the harmful waves in the target space. The counter units may be in an arrangement symmetric to at least one of the base units and/or target space so that the counter waves emitted therefrom may match the symmetric harmful waves. Conversely, the counter units may be disposed in an arrangement which is asymmetric to at least one of the base units and/or target space such that the asymmetric counter waves emitted therefrom may match and counter the asymmetric harmful waves in the target space. The single counter unit or multiple counter units may be in an arrangement enclosing therein at least a portion of one or multiple base units. Conversely, the single counter unit or multiple counter units may be in an arrangement in which at least a portion of the counter unit may be enclosed by one or multiple base units. It is appreciated that these arrangements generally connote a pattern of multiple counter units but that these arrangements may mean an orientation and/or alignment of a single counter unit.

The counter may also be provided in various dispositions which generally refer to orientations, alignments, distances, mobilities, and the like. The disposition of the counter unit generally depends on the countering modes (such as the source or wave matching), countering mechanisms (such as the front, rear or lateral arrangement, local or global countering, and so on), configurations of the counter unit, and the like, each of which generally depend on the configurational characteristics of at least one of the base units, wave characteristics of the harmful waves, and so on. In addition, the dispositions of the counter unit also depend upon the shapes, sizes, orientation, and/or dispositions of the target space defined on one side of and/or around the counter unit. Although not always correct, it is to be understood as heuristic rules that at least one counter unit is disposed closer to at least one base unit in the local countering mechanism and that at least one counter unit is disposed farther away from at least one base unit in the global countering mechanism.

The counter unit may be incorporated in various orientations for orienting such counter waves to the harmful waves. In one example, the counter unit may be disposed in an orientation defined with respect to a propagation direction of such harmful waves, e.g., by orienting its long and/or short axes normal to the direction of the propagation. In another example, the counter unit may be disposed in an orientation defined with respect to a direction of the electric energy (i.e., current and/or voltage), e.g., by orienting its long and/or short axes parallel to, normal to or in a preset angle relative to the direction of the electric energy. In another example, the counter unit may be disposed in an orientation defined with respect to the long and/or short axes of at least one of the base units. It is appreciated that such orientations of the counter unit may also depend upon other configurations of at least one of the base units, particularly when such a base unit irradiates the harmful waves along a direction different from at least one of its axes, different from a winding direction of its coil or other parts, and the like. When the system includes multiple counter units, all of such counter units may also be disposed in the same orientation, each counter unit may be disposed in a different orientation, at least two but not all of the counter units may be disposed in the same orientation, and the like.

The counter unit may be incorporated in various alignments for aligning such counter waves to the harmful waves. In one example, the counter unit may be aligned in one or more of the above axes and/or directions, may be wound in the same direction as at least one of such base units, and the like. In another example, such a counter unit may be misaligned with at least one of the above axes and/or directions, may be wound in a direction different from that of at least one of the base units, and so on. When the system includes multiple counter units, all of such counter units may be aligned in the same direction and/or axis, each counter unit may be aligned in a different direction and/or axis, at least two but not all of the counter units may be aligned in the same direction and/or axis, and the like. When the system includes multiple counter units, all of the counter units may be disposed in the same alignment, each counter unit may be disposed in a different alignment, at least two but not all of the counter units may be aligned in the same alignment, and the like.

The counter unit may also be disposed in a lateral, axial or a concentric alignment. In the lateral alignment, one or multiple counter units may be disposed laterally and also side by side with respect to at least one of the base units or, in the alternative, may be disposed between at least two of the base units and along the long and/or short axes of at least one of the base units. In the axial alignment, one or multiple counter units may instead be disposed along a direction of such long and/or short axes and in a preset distance from at least one of such base units. In the concentric alignment, one or multiple counter units may be disposed inside a single base unit, may be surrounded by all (or at least two but not all) of multiple base units, may enclose the single or multiple base units, and the like.

A single counter unit or multiple counter units may also be disposed in various distances from at least one of the base units and/or target space. In one example, such a counter unit may be fixedly incorporated in such an EMC display system in a preset distance from at least one of the base units in order to emit such counter waves of the wavefronts matching those of such harmful waves. When desirable, the counter unit may be arranged to receive variable electrical energy (i.e., current and/or voltage) so that the amplitudes of such counter waves may vary for countering the harmful waves of varying amplitudes, to define different target spaces, and the like. In another example, the counter unit may be movably coupled to the EMC display system and to translate and/or to rotate between at least two positions for emitting the counter waves and then propagating their wavefronts toward different portions of the wavefronts of the harmful waves with or without varying the amplitudes or directions of the counter waves. Accordingly, the counter waves may vary characteristics of their wavefronts based on the position of the counter unit with respect to at least one of such base units and/or target space. In another example, the EMC system may include multiple counter units and control the wave emitting operation of each of the counter units. By properly recruiting some or all of the counter units with or without manipulating the amplitudes and/or directions of the counter waves, the system may counter the harmful waves while defining the target space in various locations with respect to at least one of the base units. When the system includes multiple counter units, all of such counter units may be fixedly incorporated thereinto, all of such counter units may be movably incorporated therein, or at least two but not all of such counter units may be movable incorporated therein.

The disposition of the counter unit may be assessed in terms of the distances measured along the longitudinal axis of at least one of the base units, along the short axis thereof, around at least one of the axes, and so on. The counter unit may be disposed closer to the target space than at least one of the base units as in the front arrangement, farther away from the target space than at least one of the base units as in the rear arrangement or flush with the target space as in the lateral arrangement. When the system includes multiple counter units, all of the counter units may be disposed in the same arrangement or at least two of such units may be disposed in different arrangements. In addition, all of the counter units may be disposed in an equal distance from the base units or, alternatively, at least two of such counter units may be disposed in different distances therefrom. It is appreciated that the counter unit is preferably disposed on the same side of at least one of the base units with respect to the target space. Even when the counter unit is disposed on an opposite side of at least one of such base units with respect to the target space, the counter unit may still be able to counter such harmful waves, although such a disposition may not be the preferred embodiment.

The counter unit may be incorporated into various parts of the system and disposed in various exposures as well. When the system includes the body, the counter unit may be disposed on or over an exterior surface of the body, on or below an interior surface of the body, inside the body, and/or embedded into the body. The counter unit may instead be disposed on or over an exterior surface of the wave source, on or below an interior surface of such a wave source, embedded between such surfaces of the wave source, inside the wave source, and so on. The counter unit may be disposed on or over an exterior surface of at least one of such base units, on or below an interior surface of at least one of the base units, embedded between such surfaces of at least one of the base unit, inside at least one of the base units, and the like. In addition, the counter unit may be disposed and enclosed by at least a portion of at least one of the base units. Similarly, at least a portion or an entire portion of the counter unit may also be exposed through the system, through its body, through its wave source, through at least one of the base units, and the like. Moreover, the counter unit may fixedly or movably couple with one or more existing parts of the system, wave source, and/or base unit or, alternatively, may couple therewith by a coupler. Similarly, the counter unit may be spaced away from the system, its wave source, and/or at least one of its base units or may form an unitary article therewith.

The counter unit may be made of and/or include various materials in order to emit the counter waves having proper amplitudes in response to the electric energy supplied thereto and matching the harmful waves. In one example, the counter and base units may be made of and/or include the same materials so that such units may emit the same amount of the counter and harmful waves per an unit amount of such electric energy. In another example, the counter and base units may include at least one common material and at least one different material so that such units may emit the similar but not identical amount of the counter and harmful waves per the unit amount of the electric energy. In yet another example, the counter and base units may be made of and/or include different materials so that the counter and base units emit different amounts of waves per the unit amount of the electric energy. In general, various characteristics of the counter and base units determined by their compositions may be electric resistance or conductivity, magnetic permittivity, resonance frequency, and the like. Thus, the counter unit may be arranged to define the same, similar or different conductivity, permittivity, and resonance frequency based on its composition. An entire portion of the counter unit may be arranged to have an identical composition or, alternatively, various portions of the counter unit may be arranged to have different compositions which may vary along the long or short axis thereof. When the system includes multiple counter units, all of such counter units may have the same composition, at least two but not all of the counter units may have the same composition, or all of such counter units may have different compositions, thereby also maintaining or varying the above properties therealong.

As described hereinabove, precisely matching the phase angles (either opposite or similar) of such counter and harmful waves is a prerequisite for countering the harmful waves irradiated by at least one of the base units with the counter waves emitted by the counter unit. This phase matching may be attained by supplying proper electric energy (i.e., electric current or voltage) to the base and counter units and also optionally electrically coupling the counter and base units with each other. For illustration purposes, the electric energy supplied to such base units is to be referred to as a "source energy" hereinafter, and the electric current and voltage of the "source energy" are to be referred to as "source current" and "source voltage" hereinafter, respectively. In one example, identical source current or voltage may be supplied to the base and counter units either sequentially or simultaneously so that the phase angles of such harmful and counter waves are properly synchronized. In another example, the counter unit is supplied with only a portion of the source current or voltage sequentially or simultaneously, where the phase angles of such harmful and counter waves are still synchronized as well. In another example, the base units are first supplied with the source current or voltage, while the system thereafter modifies the amplitudes and/or directions of such source current or voltage and then supplies the modified current or voltage to the counter unit. As long as the phase angles of such source energy is maintained during modification, such counter and harmful waves are properly phase synchronized. In another example, the base units are first supplied with the source energy, and the system provides an analog of such source energy and supplies the analog energy to the counter unit with or without modifying the amplitudes and/or directions thereof, where such a system may employ various electronic components, circuits, and/or controllers to provide such an analog. As long as the phase angles of the electric energy is kept in the analog energy, such counter and harmful waves are phase synchronized as well. In another example, the counter unit is electrically coupled to such base units in a series mode, in a parallel mode or in a hybrid mode, where the counter unit is supplied with such source energy, modified source energy or analog energy as described hereinabove and where the counter unit may be supplied with such energy sequentially or simultaneously with the base units. When the system has multiple counter units, all of such counter units may be supplied with the same energy, at least two but not all of such units may be supplied with the same energy, each unit may be supplied with different energy, and the like. When the system includes multiple base units which are supplied with different source energies, the single counter unit may be supplied with only one of such energies, with a combination of at least two of such energies, and the like. When the system includes multiple counter units, such counter units may couple with the single or multiple base units in the same mode or different modes, the counter units may instead be supplied with the same energy or different energies sequentially or simultaneously, and the like. It is appreciated in all of the above examples, that the phase matching also depends upon other configurations and/or dispositions of the counter unit so that a direction of winding of the counter unit, orientation of the counter unit, and/or alignment thereof may have to be considered to accomplish the proper phase matching.

Further details of the source and wave matching are to be provided hereinafter. As described above, it is appreciated in such source matching that there does not exist any one-to-one correlations between the configuration of the counter unit and the configuration (or wave characteristics) of such counter waves. That is, the counter waves defining a certain configuration (or wave characteristics) may be obtained by a single counter unit which defines a certain shape and size and is provided in a certain arrangement, by another counter unit which defines a similar shape and size but is provided in another arrangement, by another counter unit which has a different shape and size but is provided in a similar arrangement, by at least two counter units defining preset shapes and sizes and provided in a preset arrangement, by the same number of counter units defining different shapes and/or sizes or in a different arrangement, by a different number of counter units defining similar shapes and/or sizes or in a similar arrangement, and the like. It is appreciated in such wave matching that there does not exist any one-to-one correlation between the disposition of the counter unit and the wavefronts of the counter waves emitted by the counter unit. In other words, the wavefronts with certain shapes may be obtained by a single counter unit which defines a certain configuration and is disposed in a certain position with respect to at least one of such base units and/or target space, by another single counter unit which defines another configuration and is disposed in another position, by at least two counter units which define preset configurations and are disposed in preset positions, by the same number of counter units having different configurations and disposed in different positions, by a different number of counter units defining different configurations and disposed in different positions, and so on. There are, however, a few heuristic rules which may apply not only to such source matching but also to the wave matching. The first rule is that the counter unit incorporated in the front arrangement preferably has a characteristic dimension which is greater than that of at least one of the base units, when other things being equal, to increase the radii of curvature of the wavefronts of the counter waves and to attain better matching between the counter and harmful waves. The second rule is the reverse of the first rule and dictates that the counter unit which is disposed in the rear arrangement preferably has a characteristic dimension less than that of at least one of the base units so as to decrease the radii of curvature of the wavefronts of the counter waves and to attain better matching between the counter and harmful waves. In order to match the amplitudes of such counter and harmful waves, however, the longer or wider counter unit in the front arrangement is arranged to emit the counter waves of the amplitudes less than those of the harmful waves. Similarly, the shorter or narrower counter unit in the rear arrangement is arranged to emit such counter waves of the amplitudes greater than those of the harmful waves. The third rule says that disposing multiple counter units emitting the counter waves of the same or similar phase angles tends to flatten the wavefronts of a sum of the counter waves and to increase the radii of curvature of the wavefronts of the counter waves. The fourth rule is then the reverse of the third rule and says that disposing a less number of counter units tends to sharpen the wavefronts of the sum of the counter waves and to further decrease the radii of curvature of the wavefronts of the counter waves. The fifth rule says that the wavefronts of the sum of the counter waves may be sharpened and the radii of curvature of such wavefronts may be decreased when at least one but not all of multiple counter units may emit the counter waves of the phase angles opposite to those of other counter units. It is appreciated that these rules do not generally apply to the counter units emitting the counter waves with the wavefronts defining the shapes different from the shape of the counter unit, and that those rules do not generally apply to the counter units with the non-uniform emitting power either which will be described in greater detail below.

A main purpose of the source matching is to manipulate the configuration of the counter unit to match that of at least one of the base units such that the counter waves emitted from the counter unit better match the harmful waves irradiated from the base unit. When a system preferentially depends upon the source matching to counter the harmful waves, its counter unit may preferably be disposed in a preset or reasonable distance from at least one of the base units, for any advantages which may be obtainable by the similarly configured counter unit may be lost otherwise. It is appreciated that the source matching is most useful when at least one of the base units defines a simple and/or symmetric configuration or when it is reasonably feasible to provide a replica of at least one of the complex base units. When the system has a single wave source with multiple base units or multiple waves sources each including at least one base unit, a single counter unit may be arranged to accomplish the source matching with respect to multiple base units or, alternatively, multiple counter units may be arranged to accomplish the source matching with respect to multiple base units. The source matching may include a shape matching, size matching, arrangement matching, disposition matching, intensity matching, and other configurational matching.

Some details of the shape matching have been disclosed heretofore. For example, the counter unit may be provided as a 3-D or bulk analog which corresponds to a replica or an approximation of a single or multiple 3-D base units, may be provided as a 2-D or planar analog which is an approximation of a single or multiple 3-D or 2-D base units or which is a replica of a single or multiple 2-D base units, may be formed as an 1-D or linear analog which is an approximation of a single or multiple 3-D, 2-D or 1-D base units or which is a replica of a single or multiple 1-D base units, and so on. Similarly, multiple counter units may be constructed as 3-D analogs which are the replica or approximation of a single or multiple 3-D base units, may be fabricated as the 2-D analogs which are the approximation of a single or multiple 3-D or 2-D base units or which are the replica of a single or multiple 2-D base units, may be fabricated as the 1-D analogs which are the approximation of a single or multiple 3-D, 2-D or 1-D base units or which are the replica of one or multiple 1-D base units, and the like. Such analogs may define continuous shapes or may have shapes defining multiple holes or openings, may form solid shapes or deformable shapes, may define symmetric or asymmetric shapes, and the like. The shapes of any of such analogs may be determined based upon the above countering mechanisms or, conversely, such shapes may dictate other configurations of such analogs, may decide proper countering mechanisms adopted thereby, and the like.

The size matching may be embodied by defining the counter unit to be larger than, similar to or smaller than at least one of the base units whether or not the counter unit may maintain such similarity between the configurations of the counter and base units. Whether or not the counter unit may emit the counter waves defining the wavefronts with the shapes similar to the counter unit itself, the size of the counter unit determines an extent of dispersion and/or flattening of such counter waves, edge characteristics of such wavefronts, and the like. As described above, the size of the counter unit is also determined by various countering mechanisms adopted thereby, disposition thereof, amplitudes of the electrical energy supplied thereto, and the like. Conversely, the size of such a counter unit may dictate the selection of other configurations thereof, proper countering mechanisms, and the like.

The disposition matching may be embodied by manipulating the orientation of the counter unit, alignment thereof, distance to at least one of the base units and/or target space therefrom, its mobility, and the like. As described herein, the counter unit may be oriented in the preset relations with respect to such axes and/or various directions, may be disposed in the front, rear or lateral arrangement, may be aligned or misaligned with such directions and/or axes, may be aligned or misaligned with at least one of the base units axially, radially, angularly, concentrically, laterally, and the like. The disposition of the counter unit may also be dictated by various countering mechanisms adopted thereby, shapes and sizes thereof, amplitudes of the electrical energy supplied thereto, and the like. Conversely, the disposition of the counter unit may dictate other configurations of the counter unit, proper countering mechanisms employed thereby, and the like.

The intensity matching may be embodied by manipulating the amplitudes of the counter waves emitted by the counter unit. For example, the counter waves may define the amplitudes greater than, similar to or less than those of the harmful waves when measured in a certain distance from at least one of the base units, when measured across the target space or in a preset position inside the target space, and the like. The amplitudes of the counter waves are further dictated by various countering mechanisms employed thereby, shapes and/or sizes thereof, disposition thereof, amplitudes of such electrical energy supplied thereto, and the like. Conversely, the amplitudes of the counter waves may determine other configurations of the counter unit, proper countering mechanisms, and the like.

A main purpose of the wave matching is to dispose the counter unit along at least one of such wavefronts of the harmful waves and to emit the counter waves defining the wavefronts capable of matching and countering those of the harmful waves. When a system preferentially depends on the wave matching to counter such harmful waves, its counter unit may be disposed anywhere around at least one of the base units in any distance as long as the counter wavefronts may match the harmful wavefronts. It is appreciated that the wave matching is most powerful when at least one of the base units defines a rather complex or asymmetric configuration or when it is impossible to form a replica or approximation of such a complex base unit. When the system has a single wave source with multiple base units or includes multiple wave sources each including at least one base unit, a single counter unit may be arranged to attain the wave matching with multiple base units or multiple counter units may instead be arranged to perform the wave matching with multiple base units. The only disadvantage or complication as to the wave matching is that detailed shapes and distribution of the wavefronts of the harmful waves have to be assessed a priori quantitatively or at least qualitatively.

In one type of the wave matching, the counter waves are emitted by at least one counter unit defining an uniform emitting capacity in which amplitudes per an unit configuration of the counter unit such as its length, width, radius or diameter, area, and/or weight is maintained uniform.

Accordingly, the counter unit emits the counter waves defining the wavefronts shaped similarly to the counter unit itself and, when disposed along the wavefronts of the harmful waves, counters such harmful waves in the target space. In another type of the wave matching, the counter waves are also emitted by the counter unit with a non-uniform emitting capacity in which amplitudes per the unit configuration of the counter unit vary thereacross. In this arrangement, the counter unit emits the counter waves defining the wavefronts which are not similar to the shape of the counter unit. Therefore, the counter unit of this non-uniform capacity are disposed not along a single wavefront of the harmful waves but across at least two of such wavefronts in order to emit the counter waves capable of matching the harmful waves in the target space.

It is appreciated that the counter units with the uniform emitting capacity may also be disposed along at least two wavefronts of the harmful waves as exemplified in FIG. 2K. When multiple counter units are disposed in different wavefronts of the harmful waves, such units may also be arranged to emit the counter waves of different amplitudes in order to compensate discrepancies in the distances to at least one of the base unit therefrom. This compensation may be attained by various means, e.g., by adjusting the shapes and sizes of the counter units, by adjusting the amount of the electric energy supplied thereto, by controlling the orientations and/or alignments of the counter units, and the like. As far as a sum of the counter waves defines the wavefronts which match those of the harmful waves in the target space, such counter units may be disposed along adjacent or space-apart wavefronts of such harmful waves in various configurations and/or dispositions.

Similar to their counterparts in the case of the source matching, the counter unit for the wave matching may similarly have a shape of a wire, a strip, a sheet, a tube, a coil thereof, a spiral thereof, and/or a mesh thereof, may define a combination of two or more of such shapes without forming any holes and/or openings therethrough, may form an array of two of more of such shapes while defining multiple holes and/or openings therethrough, and the like, where examples of the combinations and/or arrays may also include, but not be limited to, a bundle of multiple identical or different shapes bundling each other, a braid of multiple identical or different shapes braided along each other, and the like. The counter unit may then be disposed along the single or multiple wavefronts of the harmful waves.

Such EMC display systems of the present invention may generally be designed for countering the harmful waves in a carrier frequency range or an extremely low frequency range from about 50 Hz to about 60 Hz or another frequency range of less than about 300 Hz. Therefore, in the preferred embodiment of this invention, various counter units of the EMC display systems are also arranged to emit the counter waves in such carrier frequency range or extremely low frequency range of from about 50 Hz to about 60 Hz or the frequency range of less than about 300 Hz, thereby countering the harmful waves in those frequency ranges. Considering various medical findings and/or presumptions that a main culprit of the harmful waves are those in these frequency ranges, these counter units are believed to effectively eliminate those harmful frequency components of the harmful waves irradiated by the base units of the EMC systems.

Various counter units of the EMC display systems of the present invention may be arranged to emit the counter waves in an ultra low frequency range of less than about 2 kHz or about 3 kHz, in a very low frequency range of less than about 30 kHz, and in a low frequency range of less than about 300 kHz to counter the harmful waves in the similar frequency ranges. The counter units may also be arranged emit the counter waves in other frequency ranges such as the radio waves of frequencies ranging from about $5 \times 10^2$ Hz to about $10^8$ Hz, microwaves of frequencies ranging from about $10^8$ Hz to about $10^{12}$ Hz, and the like, in order to counter the harmful waves of similar frequency ranges. When desirable, such counter units may be arranged to emit the counter waves defining higher frequencies such as, e.g., ultraviolet rays of frequencies ranging from about $7.5 \times 10^{14}$ Hz to about $10^{17}$ Hz, X-rays of frequencies ranging from about $7 \times 10^{16}$ Hz to about $10^{19}$ Hz, gamma rays in a frequency range over and beyond $5 \times 10^{18}$ Hz, and the like, for countering the harmful waves of similar frequency ranges.

Such counter units may further be arranged to selectively counter specific components of the harmful waves or, alternatively, to specifically preserve specific components of such harmful waves while countering (i.e., canceling and/or suppressing) the rest of the harmful waves. For example and particularly when the harmful waves include higher frequency components, the counter units may be specifically arranged to preserve beneficial waves such as, e.g., infrared rays including far infrared rays in a frequency range from about 300 gHz to about 10 tHz, medium infrared rays in a frequency range from about 10 tHz to about 100 tHz, near infrared rays in a frequency range from about 100 tHz to about 700 tHz, and the like, while countering the rest of the harmful waves including those of the carrier frequency range and extremely low frequency ranges. Conversely, the counter units may be arranged to emit the infrared rays including such far-, medium-, and/or near-infrared rays as well.

In another aspect of the present invention, various counter units may also be implemented into various prior art display devices and convert such to the EMC display systems in which such harmful waves irradiated by their base units may be countered by the counter waves.

In one exemplary embodiment of this aspect of the present invention, the counter units may be implemented into any base units shaped as electrically conductive wires, strips, sheets, tubes, coils, spirals, and/or meshes or, in the alternative, to any electrically semiconductive and/or insulative wires, strips, sheets, tubes, coils, spirals, and/or meshes for minimizing the irradiation of the harmful waves by countering such harmful waves by the counter waves, e.g., by canceling at least a portion of the harmful waves in the target space and/or suppressing the harmful waves from propagating to such a target space. Such counter units may be made of and/or include at least one material which may then be electrically conductive, insulative or semiconductive. The counter units may be implemented to any of the base units which have the shapes formed by one or multiple wires, strips, sheets, tubes, coils, spirals, and/or meshes, by modifying the shapes of one or multiple wires, strips, sheets, tubes, coils, spirals, and/or meshes, where a few examples of the modified shapes may be a solenoid and a toroid each formed by modifying the shape of the coil. In general, the counter units of this embodiment may be disposed in any of the foregoing arrangements and may counter the harmful waves by any of the foregoing mechanisms. Accordingly, a similarly or identically shaped and/or sized counter unit may be disposed lateral or side by side to one or more base units, may be axially, radially or angularly aligned with one or more base units, may enclose therein one or more base units, may be enclosed by one or more base units, may wind around one or more base units, may be wound by one or more base units, and the like, based on the source matching.

In the alternative, a similarly or differently shaped and/or sized counter unit may be disposed along one or more wavefronts of the harmful waves irradiated by one or more base units for the wave matching. In addition, such counter units may be employed in a proper number and/or arrangement to counter the harmful waves according to the local countering or global countering.

In another exemplary embodiment of this aspect of the present invention, the counter units may also be implemented into any conventional electric and/or electronic elements such as, e.g., resistors, inductors, capacitors, diodes, transistors, amplifiers, fuses, triacs, and other signal processors and/or regulators in order to counter the harmful waves irradiated by the elements, where the electric and/or electronic elements function to manipulate at least one input signal supplied thereto and to produce at least one output signal at least partially different from the input signal. All of the above electric and/or electronic elements may qualify as the base units within the scope of the present invention when the unsteady current flows therein or when the unsteady voltage is applied thereacross. In addition, the above elements may also qualify as the base units within the scope of this invention when any of the elements produces the unsteady output signal (i.e., the electric current or voltage) in response to the input signal which may be steady or unsteady. Therefore, any of the above prior art elements and/or display devices including such elements may be converted to the EMC elements and/or EMC display systems by incorporating various counter units which define any of the above configurations in any of the above dispositions and/or arrangements, thereby countering such harmful waves in any of the above mechanisms. It is appreciated that such counter units may be provided in any dimension such that the EMC elements may be provided in a range of microns or nanometers.

Figure 3A:
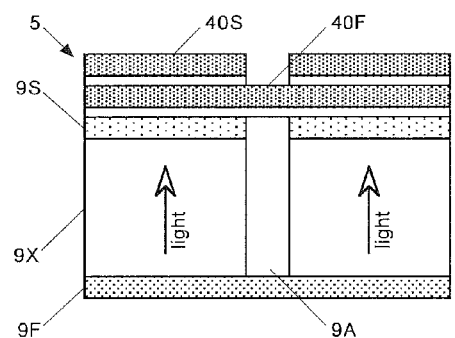
FIGS. 3A to 3O are schematic cross-sectional views of exemplary counter units incorporated into pixels of EMC display systems and operating based on a local countering mechanism according to the present invention.
Figure 3D:
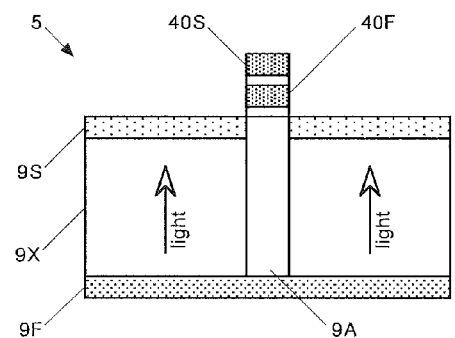

In another exemplary embodiment of this aspect of the invention, various counter units may be incorporated into or around various electrodes and/or pixels of such display units of the EMC display system for countering the harmful waves irradiated by various base units thereof, where examples of such display units may include, but not be limited to, the OLED units, IOLED units, PDP units, LCD units, CRT units, DLP units, SED units, and the like. Therefore, any conventional display units including such EMC display units therein may then be converted into the EMC display systems such as, e.g., the EMC OLED systems, EMC IOLED systems, EMC PDP systems, EMC LCD systems, EMC CRT systems, EMC DLP systems, EMC SED systems, and the like. In addition, other conventional display units which emit and/or transmit the visible light rays through their pixels may similarly be converted to the EMC display systems by incorporating therein one or more of such counter units. FIGS. 3A to 3O show schematic perspective views of various counter units each of which approximates a single or multiple base units of the display units and provided in various configurations in the source or wave matching according to the present invention. It is appreciated in all of these figures that only the electrodes and pixels are selected as the primary base units of such EMC display system. It is appreciated, therefore, that other conductive, semiconductive, and/or insulative parts of any EMC display systems irradiating the harmful waves are omitted from all of the figures and that, when necessary, such parts may also be properly countered by resorting to any of such counter units as described above. It is also appreciated for the simplicity of illustration that each figure depicts only a portion of the EMC display system by including a pair of pixels of the above display units and that neighboring regions of the EMC system not shown in each figure may include the base units and counter units similar or identical to those shown in such a figure. It is further appreciated that various EMC display systems are arranged in such an orientation that the pixels emit and/or transmit the visible light rays upwardly, as manifest by arrows and that the EMC display systems may then include the pixels of the OLED, IOLED, PDP, LCD, DLP, and SEP display systems which have been exemplified in FIGS. 1A to 1F or which have not been included in FIGS. 1A to 1F but described in conjunction therewith. It is to be reminded that various counter units and their counters described in the following figures are to be interpreted to extend laterally, either from left to right (or from right to left) of the sheet or vertically into (or out of) the sheet. In this context, a counter unit depicted as a strip in the figure may in fact correspond to a strip elongated in either of the above directions.

In the first set of examples of FIGS. 3A to 3I, various counter units may be provided separately from the base units of various display units and counter the harmful waves irradiated from such base units in the local countering mechanism. It is appreciated that these counter units may be incorporated into any of the above display units which are arranged to receive the electrical energy in a direction which may be identical to or opposite from a direction of the visible light rays which is denoted by an arrow in each figure.

In one example of FIG. 3A, an EMC display system 5 includes a pair of pixels 9X defined over a substrate (not included in the figure), at least one first electrode 9F which includes multiple first paths laterally extending parallel to each other (e.g., from left to right of the sheet) and electrically coupled to bottom portions of such pixels 9X, and at least one second electrode which includes multiple second electrode 9S laterally extending parallel to each other (e.g., into or out from the sheet) and electrically coupled to top portions of the pixels 9X. These pixels 9X are also spaced apart from each other by a gap 9A which may be left empty or filled up by suitable insulating materials. On top of such pixels 9X are deposited a counter unit which consists of at least one first counter 40F and at least one second counter 40S, where the first counter 40S is shaped and sized similar or identical to the first electrode 9F, while the second counter 40S is shaped and sized similar or identical to the second electrode 9S. To prevent direct electric contact between the first and second counters 40F, 40S, insulation layers are incorporated therebetween, which are represented by thin blank layers in the figure.

In operation, the driver (not included in this figure) selects to charge the left pixel 9X by flowing the electrical energy in the first electrode 9F and the left conductive path of the second electrode 9S. Depending upon the configuration, the electric current flows downwardly (or upwardly), and the light emitting element of the left pixel 9X is charged and then emits the visible light rays through the second electrode 9S. At the same time, such first and second electrodes 9F, 9S irradiate the harmful waves which propagate along the same direction as the visible light rays to an user. To counter the harmful waves, a counter electrical energy is supplied to the first counter 40F and to the left second counter 40S so that the counter waves emitted by the first counter 40F counter the harmful waves irradiated by the first electrode 9F and that the counter waves emitted from the second counter 40 counter the harmful waves irradiated by the second electrode 9S. More particularly, the counter energy may flow in the counters 40F, 40S in directions which are opposite to those along the electrodes 9F, 9S so that the counter waves define the phase angles at least partially opposite to those of the harmful waves. In addition, such counters 40F, 40S receive the counter electrical energy of which amplitudes may be manipulated to render the counter waves define the amplitudes at least partially similar to those of the harmful waves. Accordingly, the counter unit 40 may counter the harmful waves by canceling such harmful waves in a target space defined around the user due to the amplitudes and/or phase angles of the counter waves, by suppressing the harmful waves from propagating toward the target space due to the amplitudes and/or phase angles of such counter waves, and the like. In this context, each of the counters unit 40 is deemed to define the shape (and/or size) analog of each of the base units of the electrodes 9F, 9S and to operate in the local countering mechanism. It is appreciated that such pixels 9X themselves may serve as the base units by irradiating the harmful waves while emitting the visible light rays. As described hereinabove, however, these harmful waves preferentially propagate in lateral directions and, accordingly, may not harm the user. When the pixels 9X irradiate the harmful waves propagating along with the visible light rays along the same direction and the amplitudes of the harmful waves are not negligible, these upwardly propagating harmful waves may be countered with other mechanisms. In one example, the first and second counter 40F, 40S may be arranged to form an electric contact therebetween and induce a flow of electric current therethrough, thereby emitting the counter waves propagating along the same direction as the upwardly propagating harmful waves while countering such harmful waves. In another example, the first counter 40F may be arranged to form an electric contact therebetween and induce the flow of electric current therethrough, thereby emitting the similar counter waves. It is appreciated in these examples that amplitudes of such electric contacts may be manipulated only to match a strength of such harmful waves upwardly propagating across the pixel. Therefore, the insulation layers may include semiconductive materials or may form one or more regions of conductive materials through which the electric current may flow.

Figure 3B:
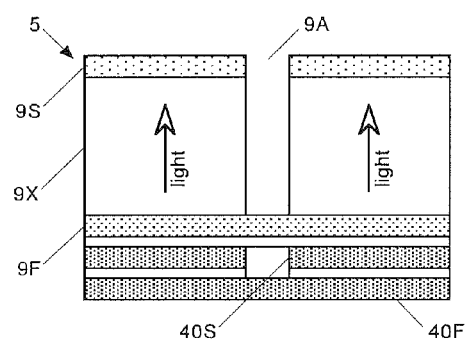
Figure 3E:
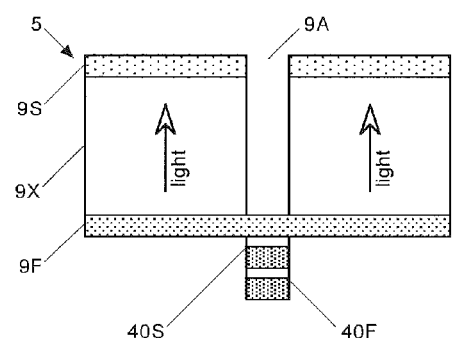

In a related example of FIG. 3B, an EMC display system 5 includes a pair of pixels 9X defined over the substrate, at least one first electrode 9F, and at least one second electrode, each of which is similar or identical to that of FIG. 3A. Contrary to that of FIG. 3A, a counter unit is disposed below the pixels 9X so that the second counters 40S are interposed from the first electrode 9F by an insulation layer and that first counters 40F are also interposed from the second counters 40S by another layer of insulative materials. By manipulating configurations of such counters 40F, 40S and the direction of the counter electrical energy supplied thereto, the counter unit may emit the counter waves capable of countering the harmful waves in the target space formed around the user. In another related example of FIG. 3C, an EMC display system 5 similarly includes a pair of pixels 9X formed over the substrate, at least one first electrode 9F, and at least one second electrode, each of which is similar or identical to those of FIGS. 3A and 3B. Contrary to those of FIGS. 3A and 3B, a counter unit is disposed over and below the pixels 9X. For example, the first counter 40F is interposed from the first electrode 9F by the bottom insulation layer, while the second counter 40S is interposed from the second electrode 9S by the top insulation layer. By manipulating configurations of such counters 40F, 40S and the direction of the counter electrical energy supplied thereto, the counter unit may emit the counter waves capable of countering the harmful waves in the target space formed adjacent to the user. Further configurational and/or operational characteristics of the counter units of FIGS. 3B and 3C may be similar or identical to those of the counter unit of FIG. 3A.

Figure 3C:
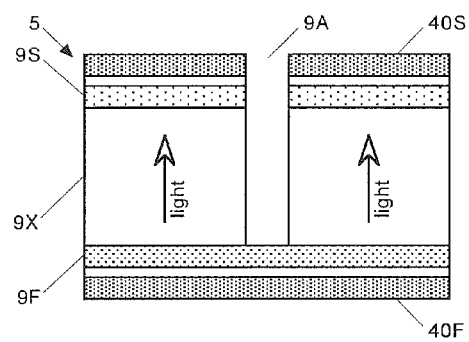

It is appreciated in FIGS. 3A to 3C that the first and second counters of the counter unit may be arranged to define various configurations. For example, at least one of the counters may be arranged to define a length, a width, and/or a height which may be similar to, identical to or different from those of the base unit countered thereby. The first and second counters may also have the same, similar or different configurations with respect to each other. As described hereinabove, such first and second counters may be directly mechanically and/or electrically contact each other or, in the alternative, may be mechanically and/or electrically separated from each other. In addition, at least one of the first and second counters may be directly mechanically and/or electrically contact each other or, alternatively, may be mechanically and/or electrically separated from each other as well. When desirable, the first and second counters may be disposed in a reverse order as well. In another example, at least one of such counters may be arranged to have a chemical composition which may be also similar to, identical to or different from that of the base unit countered thereby. The first and second counters may have the same, similar or different chemical compositions with respect to each other. As briefly described hereinabove and as will be described below, the counter unit and various counters may receive the counter electrical energy in various modes as well. In one example, the counter electrical energy may be similar or identical to the source electrical energy supplied to the base unit. In another example, the counter energy may be only a portion of the source energy. In another example, the counter energy may be provided independently of the source energy but have the same, similar or different directions and/or amplitudes. When the counter unit includes multiple counters therein, each of the counters may receive the identical, similar or different counter energy with the same, similar or different amplitudes and/or directions.

In another example of FIG. 3D, an EMC display system 5 includes a pair of pixels 9X defined on the substrate, at least one first electrode 9F which forms multiple first paths, and at least one second electrode 9S which also has multiple second paths, each of which is similar or identical to that of FIG. 3A. On top of the gap 9A defined between the pixels 9X are deposited a counter unit having at least one first counter 40F and at least one second counter 40S, where the first counter 40F is separated from the pixels 9X (or gap 9A) by an insulation layer and where the second counter 40S is separated from the first counter 40F by another insulation layer. It is to be understood that such first and second counters 40F, 40S of this embodiment are substantially smaller or narrower than the pixels 9X as well as the electrodes 9F, 9S. Conversely, such counters 40F, 40S may be deemed to be wider than such pixels 9X and electrodes 9F, 9S when the pixels 9X have to define wider gaps 9A.

In operation, the driver selects to charge the left pixel 9X by flowing the electrical energy in the first electrode 9F and the left conductive path of the second electrode 9S. Depending on their detailed configuration, the electric current flows downwardly (or upwardly), while the light emitting element of the left pixel 9X is electrically charged and emits the visible light rays through the second electrode 9S. At the same time, the first and second electrodes 9F, 9S irradiate the harmful waves which propagate along the same direction as the visible light rays to an user. To counter the harmful waves, a counter electrical energy is supplied to the counters 40F, 40S along appropriate directions so that the counter waves emitted by the first counter 40F counter the harmful waves irradiated by the first electrode 9F (or second electrode 9S) and that the counter waves emitted from the second counter 40 counter the harmful waves irradiated from the second electrode 9S (or first electrode 9F). In addition, the counter energy may flow in the counters 40F, 40S in those directions which are opposite to those along such electrodes 9F, 9S so that the counter waves have the phase angles at least partially opposite to those of the harmful waves. Such counters 40F, 40S may receive the counter energy of which amplitudes are manipulated to render the counter waves define the amplitudes at least partially similar to those of the harmful waves. Therefore, the counter unit 40 may counter the harmful waves by canceling such harmful waves in a target space defined around the user due to the amplitudes and/or phase angles of the counter waves, by suppressing the harmful waves from propagating toward the target space due to the amplitudes and/or phase angles of such counter waves, and the like. In this context, each of the counters unit 40 is deemed to define the shape (and/or size) analog of each of the base units of the electrodes 9F, 9S and to operate in the local countering mechanism. As the pixels 9X irradiate the harmful waves propagating with the visible light rays in the same direction and the amplitudes of the harmful waves are not negligible, these upwardly propagating harmful waves may be countered with various mechanisms of defining electrical contacts between the counters 40F, 40S or between one of the counters 40F, 40S and the second electrode 9S as described in conjunction with FIG. 3A. Other configurational and/or operational characteristics of the counter unit of FIG. 3D may be similar or identical to those of the counter units of FIGS. 3A to 3C.

Figure 3F:
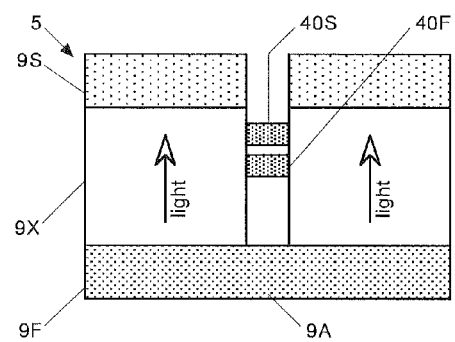

In a related example of FIG. 3E, an EMC display system 5 includes a pair of pixels 9X defined on the substrate, at least one first electrode 9F, and at least one second electrode 9S, each of which is similar or identical to that of FIG. 3D. Contrary to that of FIG. 3D, the counter unit is disposed below the pixels 9X such that the second counter 40S is isolated from the first electrode 9F by an insulating layer, while the first counter 40F is spaced away from the second counter 40S by another insulating layer. By manipulating configurations of the counters 40F, 40S and direction of the counter electrical energy supplied thereto, the counter unit emits such counter waves which are capable of countering the harmful waves in the target space formed around the user. In another related example of FIG. 3F, an EMC display system 5 includes a pair of pixels 9X, at least one first electrode 9F, and at least one second electrode 9S, each of which is also similar or identical to that of FIG. 3D. A counter unit similar to those of FIGS. 3D and 3E is disposed along the gap 9A defined between the pixels 9X such that the first and second counters 40F, 40S are disposed one over the other, separated by an insulation layer, and sandwiched between the adjoining pixels 9X. It is appreciated that these counters 40F, 40S may be electrically insulated from outer walls of the pixels 9X when desirable. In another related example not included in the figure, a counter unit similar to those of FIGS. 3D to 3F may also be disposed similar to that of FIG. 3C so that the first counter 40F is disposed at the bottom of the interpixel gap 9A, while the second counter 40S is disposed on top of the gap 9A. Further configurational and/or operational characteristics of the counter units of FIGS. 3E and 3F are similar or identical to those of the counter units of FIGS. 3A to 3D.

Figure 3G:
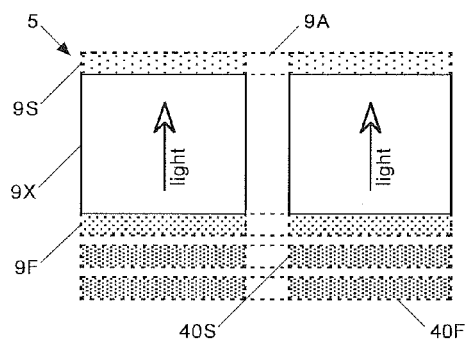

In another example of FIG. 3G, an EMC display system 5 includes a pair of pixels 9X defined on the similar substrate, at least one first electrode 9F which includes at least one first path, and at least one second electrode 9S which also includes at least one second path. It is appreciated that the first and/or second electrode 9F, 9S may define planar configurations and cover an entire top (or bottom) surface of such pixels 9X as exemplified in FIGS. 1B to 1E. The EMC system 5 also includes a counter unit which is generally similar to that of FIG. 3B, except that its first and/or second counters 40F, 40S may similarly be arranged to define the planar configurations and to cover the entire first and second electrodes 9F, 9S. Therefore, such a counter unit may be suitable for countering the harmful waves irradiated by the electrodes 9F, 9S which encompass relatively larger areas of the real estate of the screen of the display unit which incorporates the electrode electrically coupling with multiple rows or columns of the. In a related example of FIG. 3H, another EMC display system 5 also includes a pair of pixels 9X, at least one first electrode 9F, and at least one electrode 9S, each of which is also similar or identical to that of FIG. 3G. The EMC system 5 also includes a counter unit which is typically similar to that of FIG. 3C, except that the first and second counters 40F, 40S may also be arranged to define the planar configurations and to cover the entire first and second electrodes 9F, 9S, similar to that of FIG. 3H. In another related example of FIG. 3I, another EMC display system 5 includes a pair of pixels 9X, at least one first electrode 9F, and at least one electrode 9S, each of which is similar or identical to that of FIG. 3G. The EMC system 5 includes a counter unit which is similar to that of FIGS. 3D and 3E, except that the first and second counters 40F, 40S are disposed on opposite ends of the gap 9A. It is appreciated that such counter units of FIGS. 3G to 3I may be used to counter the harmful waves irradiated by the wider electrodes which encompass multiple rows and/or columns of pixels 9X and, therefore, best suited to counter such harmful waves which are irradiated from the subcontrollers or thin film transistors which drive the pixels 9X of the sets of pixels 9X. When desirable, the counters 40F, 40S may be provided with conductive paths therealong and/or thereacross in order to simulate or approximate circuitry inside the subcontrollers.

Figure 3J:
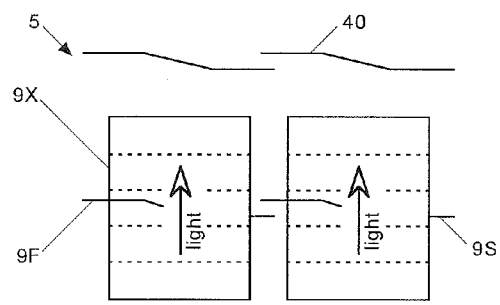
Figure 3H:
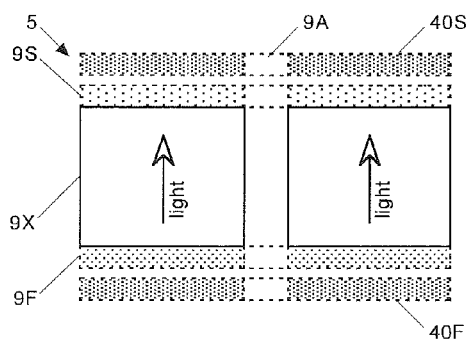
Figure 3K:
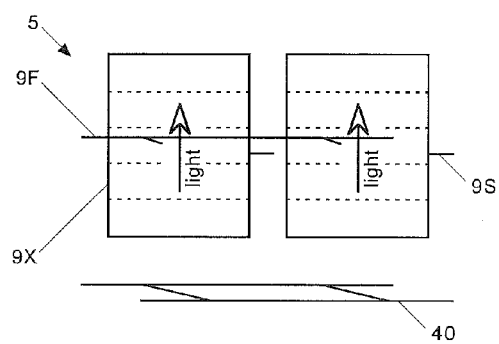
Figure 3I:
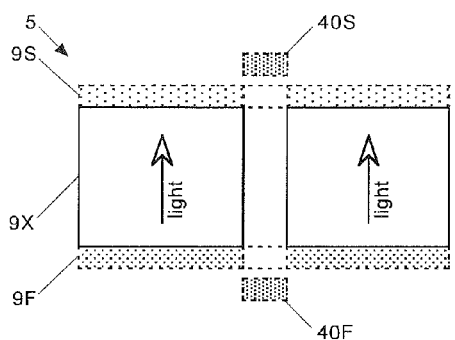
Figure 3L:
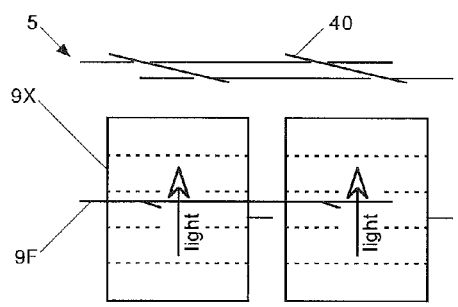

In the second set of examples shown in FIGS. 3J to 3L, various counter units may be provided separately from the base units of various display units and counter the harmful waves irradiated from such base units in the local countering mechanism. In contrary to those of FIGS. 3A to 3I, the counter units are arranged to electrically couple with opposing sides of the pixels. Accordingly, these counter units may be incorporated into any of such display units which are arranged to receive the electrical energy in a direction which may be transverse to a direction of the visible light rays which is denoted by an arrow in each figure.

In one example of FIG. 3J, such an EMC display system 5 has a pair of pixels each including multiple functional layers one of which functions as a light emitting and/or transmitting layer, another of which serves as the cathode, and yet another of which functions as the anode. The EMC system 5 also includes at least one first electrode 9F coupling with one of the layers of the pixel 9X on its side and at least one second electrode 9S also coupling with the same or different layer of the pixel 9X on its opposite side, thereby supplying the source electrical energy to the system 5 at least substantially laterally. Similar to those of FIGS. 3A to 3I, a counter unit is fabricated to define a shape (and/or size) analog of the electrodes 9F, 9S and disposed on top of the pixels or, in the alternative, over the top of both of the pixels 9X at a preset distance. Other than these, further configurational and/or operational characteristics of the counter unit of FIG. 3J are similar or identical to those shown in FIGS. 43A to 3I. In a related example of FIG. 3K, an EMC display system 5 includes a pair of pixels 9X, at least one first electrode 9F, and at least one second electrode 9S, each of which is similar or identical to that of FIG. 3J. Such an EMC system 5 also includes the counter unit which is also similar to that of FIG. 3J but is rather disposed under or below bottoms of each of such pixels 9X. In another related example of FIG. 3L, an EMC display system 5 includes a pair of pixels 9X, at least one first electrode 9F, and at least one second electrode 9S, each similar or identical to that of FIG. 3J. The EMC system 5 also includes the counter unit which includes multiple rows of conductive paths and multiple columns of conductive paths which are spaced away from each other without mechanically and electrically coupling to each other. In FIGS. 3J to 3L, the driver supplies the counter electrical energy of desirable amplitudes along the directions which simulate those along or across the pixels 9X, thereby emitting the counter waves by the counter unit 40 and countering the harmful waves therewith as disclosed hereinabove. Other configurational and/or operational characteristics of the counter units of FIGS. 3J to 3L may be similar or identical to those of the counter units of FIGS. 3A to 3I.

It is appreciated that the pixels 9X may irradiate the harmful waves propagating upwardly and defining non-negligible amplitudes. Such harmful waves may be irradiated by the light emitting and/or transmitting element and/or by internal conductive paths which may define vertical components along a height of the pixels 9X. The counter units may then be arranged to emit the counter waves so as to counter the vertically propagating harmful waves. In one example, the counter unit may be arranged to define a slanted configuration, more particularly, along a portion defined above or below the pixels 9X in order to emit the vertically propagating counter waves. In another example, at least a portion of the counter unit may also electrically couple with the top and/or bottom portions of such pixels 9X and define vertical conductive paths therealong, thereby emitting the vertically propagating counter waves and countering the harmful waves therewith.

Figure 3M:
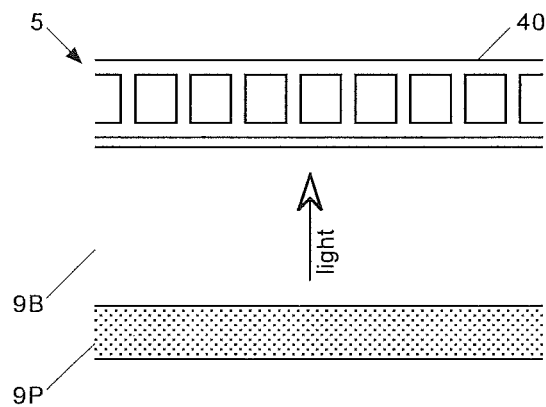
Figure 3N:
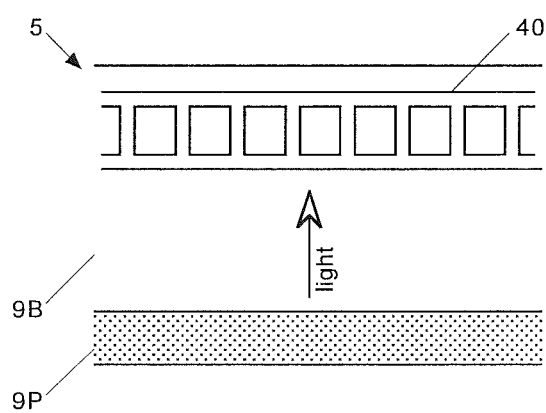
Figure 3O:
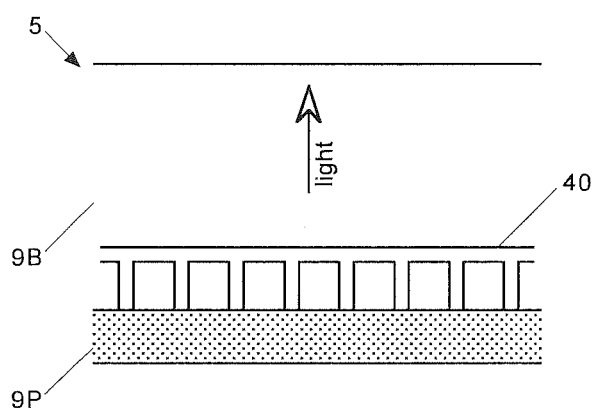

In the third set of examples of FIGS. 3M to 3O, various counter units are provided separately from the base units of various display units and counter the harmful waves irradiated from such base units in the local countering mechanism. It is appreciated that these counter units may be incorporated into any of the above display units receiving the electrical energy in a form of electron or photon rays and converting the energy of such rays into the visible light rays by phosphor materials.

In one example of FIG. 3M, an EMC display system 5 includes therein a substrate 9B which is coated with at least one phosphor material 9P, at least one electron beam generator (not shown in the figure), and at least one steering unit. The beam generator is arranged to emit a ray of electrons and impinge the electrons onto the phosphors 9P of the substrate 9B disposed in a desirable location. In response to the impinging electrons, the phosphors 9P absorb the energy of the electrons and then emit the visible light rays to the user through the transparent substrate 9B. The steering unit includes multiple sets of electromagnets, and manipulates such electromagnets to steer the electron rays along a desirable direction. The EMC system 5 includes at least one counter unit 40 which defines a planar configuration and includes a top conductive layer and a bottom conductive layer. In addition, such top and bottom layers of the counter unit 40 are arranged to electrically couple with each other by multiple vertical conductive paths defined therebetween. The counter unit 40 is also arranged to receive the counter electrical energy along the top (or bottom) layer, delivers such energy vertically downwardly (or upwardly) through the vertical paths, and then returns the energy along the bottom (or top) layer. It is appreciated that the top and bottom layers of the counter unit are arranged to flow the energy in opposite directions so that the counter waves emitted by the layers cancel each other. Accordingly, the counter unit emits the counter waves which preferentially propagate along lateral directions. This embodiment is useful when the harmful waves irradiated by the base units preferentially propagate in the lateral directions. Alternatively, the top and bottom layers may be arranged to receive the counter energy along the same direction, while the vertical paths define relatively short heights such that the counter waves emitted by this counter unit preferentially propagate along vertical directions. Such an embodiment is useful when the harmful waves irradiated by the base units preferentially propagate in the vertical directions as well. The direction of the counter electrical energy is also manipulated such that the counter waves may define the phase angles at least partially opposite to those of the harmful waves and counter the harmful waves. In a related example of FIG. 3N, another EMC display system 5 also includes the substrate 9B coated with the phosphors 9P, beam generator, and one steering unit each of which is similar or identical to that of FIG. 3M. The EMC system 5 further includes the counter unit 40 which is similar to that of FIG. 3M but embedded inside the substrate 9B. Other configurational and/or operational characteristics of the counter unit of FIG. 3N may be similar or identical to those of the counter unit of FIG. 3M. In another related example of FIG. 3O, the EMC display system 5 includes the substrate 9B coated with the phosphors 9P, beam generator, and one steering unit each of which is similar or identical to that of FIG. 3M. The EMC system 5 also includes the counter unit 40 similar to that of FIG. 3M but embedded inside the substrate 9B and electrically coupling with at least a portion of the phosphors 9P. Such a counter unit 40 offers the benefit of collecting the stray electrons from the phosphors 9P and flowing the electrons therealong in a direction of emitting the counter waves which counter the harmful waves. Further configurational and/or operational characteristics of the counter unit of FIG. 3O may be similar or identical to those of the counter units of FIGS. 3M and 3N. It is also to be understood that the counter units 40 of FIGS. 3M to 3O may be used to counter the harmful waves irradiated by the electromagnets of the steering units and/or other parts of the system 5 and that such counter units are suited for the prior art CRT display units in order to convert such units into the EMC CRT display system.

In another exemplary embodiment of this aspect of the invention, various counter units may be incorporated into or around various electrodes and/or pixels of such display units of the EMC display system for countering the harmful waves irradiated by various base units thereof, where examples of such display units are identical to those of the previous embodiment. FIGS. 4A to 4F show schematic top views of various counter units each of which approximates multiple base units of the display units and provided in various configurations in the source and/or wave matching according to the present invention. It is appreciated in all of such figures that only the electrodes and pixels are selected as the primary base units of such an EMC display system. It is appreciated, therefore, that other conductive, semiconductive, and/or insulative parts of any EMC display systems irradiating the harmful waves are omitted from all of the figures and that, when necessary, such parts may also be properly countered by resorting to any of such counter units as described above. It is also appreciated for the simplicity of illustration that each figure depicts only a portion of the EMC system and that neighboring regions of the EMC system not shown in each of the figures may include the base units and counter units similar or identical to those of the same figure. It is further appreciated that various EMC display systems are arranged in such an orientation that the pixels emit and/or transmit such visible light rays downwardly (or upwardly) and that the EMC display systems may include the pixels of the OLED, IOLED, PDP, LCD, DLP, and SEP display systems which have been exemplified in FIGS. 1A to 1F or which have not been included in FIGS. 1A to 1F but described in conjunction therewith. It is to be reminded that the counter units and their counters described in these figures are to be interpreted to extend laterally, either from left to right (or from right to left) of the sheet or vertically into (or out of) the sheet.

Figure 4A:
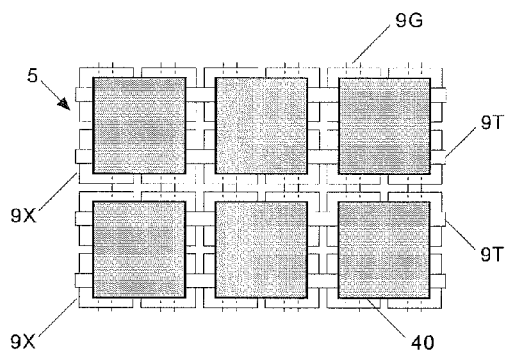
FIGS. 4A to 4F are schematic top views of exemplary counter units which are incorporated to pixels of various EMC display systems and preferentially operating in a global countering mechanism according to the present invention.

In one example of FIG. 4A, an EMC display system 5 includes therein multiple pixels 9X, multiple vertical first conductive paths 9G, and multiple horizontal conductive paths 9T, each of which may be similar or identical to those of FIG. 1A. The EMC system 5 also includes multiple counter units 40 each of which is disposed over or below a group of pixels 9X and corresponding portions of such first and second paths 9G, 9T. Each counter unit 40 may form a simple conductive sheet which approximates or simulates a pattern of an overall (or net) current flow across multiple paths 9G, 9T and/or pixels 9X enclosed therein. In the alternative, at least one counter unit 40 may define therein multiple conductive paths which approximates or simulates patterns of the paths 9G, 9T and/or pixels 9X, where such a counter unit 40 may be deemed as an aggregate of multiple counters. In a related example of FIG. 4B, an EMC display system 5 includes therein multiple sets 9E of pixels 9X, a single planar first electrode 9F, and multiple horizontal conductive paths 9T, each of which are similar or identical to those of FIG. 1E. The EMC system 5 includes multiple counter units 40 each of which is disposed over or below a single or multiple sets 9E of pixels and corresponding portions of such first electrode 9F and second paths 9T. It is appreciated that the counter units 40 may define different shapes and/or sizes in order to counter different number of pixel sets 9E. Similar to that of FIG. 4A, each counter unit 40 may form a simple conductive sheet which may approximate or simulate a pattern of an overall (or net) current flow across the first electrode 9F and/or multiple second paths 9T and/or pixels 9X enclosed therein. Alternatively, at least one counter unit 40 may define multiple conductive Paths which approximates or simulates patterns of the first electrode 9F and/or second paths 9T and/or pixel set 9E, where such a counter unit 40 may also be deemed as an aggregate of multiple counters. In another related example of FIG. 4C, an EMC display system 5 includes multiple pixels 9X, multiple vertical first conductive paths 9G, and multiple horizontal conductive paths 9T, each of which may be similar or identical to those of FIG. 1F. The EMC system 5 also includes multiple counter units 40 each of which is disposed over or below a group of pixels 9X and corresponding portions of such first and second paths 9G, 9T. Each counter unit 40 may form a simple conductive sheet which approximates or simulates a pattern of an overall (or net) current flow in multiple paths 9G, 9T and/or pixels 9X enclosed thereby or may define therein multiple conductive paths which approximates or simulates patterns of the paths 9G, 9T and/or pixels 9X. In each of FIGS. 4A to 4C, each counter unit 40 is arranged to counter multiple base units in the global countering mechanism. Except this, other configurational and/or operational characteristics of the counter units of FIGS. 4A to 4C may be similar or identical to those of the counter units of FIGS. 3A to 3O.

Figure 4D:
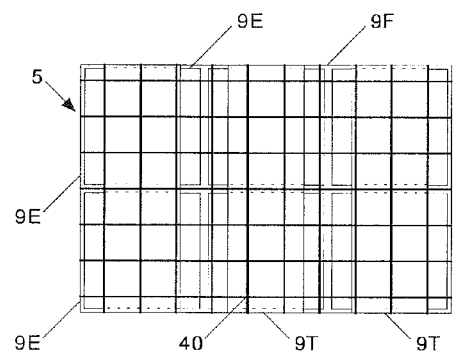
Figure 4B:
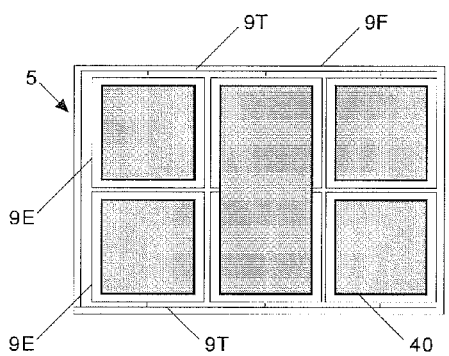
Figure 4E:
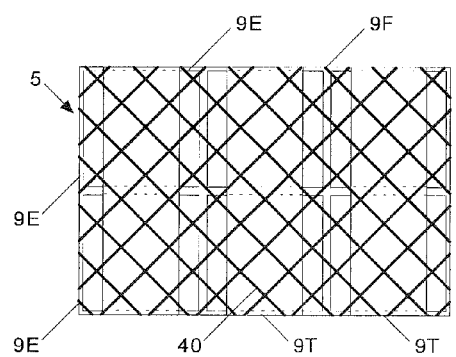
Figure 4C:
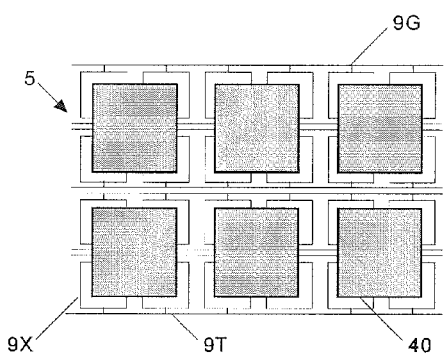
Figure 4F:
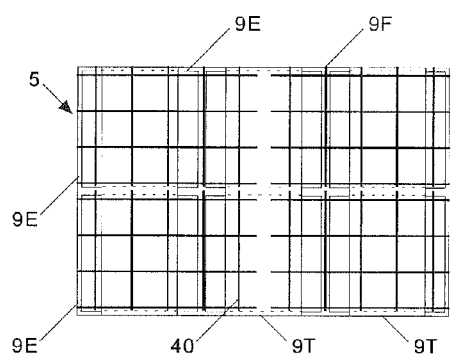

In another example of FIG. 4D, another EMC display system 5 includes multiple sets 9E of pixels arranged in multiple rows and columns, the planar first electrode 9F, and the second electrode which consists of multiple second conductive paths 9T, each similar to those of FIG. 1D. The EMC system 5 also includes a single counter unit 40 which is shaped as a mesh consisting of multiple horizontal and vertical conductive paths mechanically and/or electrically coupling with each other. The counter unit 40 is disposed over (and/or below) the system 5 and receives the counter electrical energy in preset directions in order to emit the counter waves of the amplitudes at least partially similar to those of the harmful waves irradiated by the base units to be countered thereby and of the phase angles at least partially opposite to those of such harmful waves. Accordingly, the counter unit 40 may counter the harmful waves in the target space defined around the user. In a related example of FIG. 4E, an EMC display system 5 includes multiple sets 9E of pixels, planar first electrode 9F, and second electrode with multiple second conductive paths 9T, each similar to those of FIG. 1D. The EMC display system 5 also includes a counter unit 40 which is similar to that of FIG. 4D but disposed transverse to a long (or short) axis of the pixel sets 9E and electrodes 9F, 9T. In another related example of FIG. 4F, an EMC display system 5 includes multiple sets 9E of pixels, planar first electrode 9F, and second electrode with multiple second conductive paths 9T, each similar to those of FIG. 1D. The EMC display system 5 also includes multiple counter units 40 each of which is similar to that of FIG. 4D but disposed over (or under) a smaller number of the pixel sets 9E. In addition, such counter units 40 are disposed to define multiple rows and columns. Various counter units exemplified in FIGS. 4D to 4F may define different configurations and/or may be provided in different arrangements. For example, the conductive paths of such counter units 40 may be disposed in an uniform spacing or in different spacings such that the horizontal paths may be spaced farther apart from (or closer to) each other than the horizontal paths. At least two of the same or different paths may have the same or different configurations and/or may define the same or different compositions. Such counter units 40 countering in the global countering mechanism may have other configurations which have been disclosed in the co-pending Applications. Such conductive paths of the counter unit 40 may be mechanically and/or electrically coupled to each other or may be spaced apart from each other. When desirable, only some but not all of such paths may be mechanically and/or electrically coupled to each other. The counter units 40 may be disposed on only one side of the system 5 or, alternatively, identical or different counter units 40 may instead be disposed on opposing sides of the system 5. However, the counter units 40 may well be disposed on one side of the system 5, for the target space is generally defined on such a single side thereof. It is appreciated that an efficiency in countering the harmful waves is heavily dependent on the patterns of the energy supply to the counter units 40. Therefore, the counter electrical energy may be applied from one end of the counter unit 40 to another end thereof, from one corner of the counter unit 40 to another corner thereof, from a center (or another interior location) of the counter unit 40 to an edge(s) thereof, and the like. As long as the counter units 40 may emit the counter waves capable of properly countering the harmful waves, the counter energy may be supplied thereto in various modes. Other configurational and/or operational characteristics of the counter units of FIGS. 4D to 4F are similar or identical to those of the counter units of FIGS. 3A to 3O and FIGS. 4A to 4C.

In FIGS. 4A to 4F, the EMC display system may include a single unit which may counter all or at least a substantial number of base units in the global countering mechanism or, in the alternative, may instead have multiple counter units each countering the same or different number of the base units in the same countering mechanism. In the latter case, at least one of the counter units may be arranged to counter multiple base units of the same type, i.e., only countering the electrodes or only countering the pixels or, in the alternative, may counter multiple base units of the different types, e.g., countering some electrodes and pixels at the same time. At least one of counter unit may enclose entire portions of a preset number of base units therein or expose at least a portion of such base units. When such an EMC display system includes multiple counter units operating in the global countering mechanism, at least two of such counter units may define identical, similar or different configurations, compositions, and the like. The counter units may be disposed on only one side of the system. In the alternative, the same or different number of counter units may be disposed on both sides of the system. At least two counter units may be disposed symmetrically (or asymmetrically) with respect to each other or, in the alternative, with respect to the base units. At least two counter units may mechanically or electrically couple with each other or with at least one of the electrodes or their paths. Each counter unit may be arranged to receive the counter electrical energy as described in conjunction with FIGS. 3A to 3O.

Figure 5A:
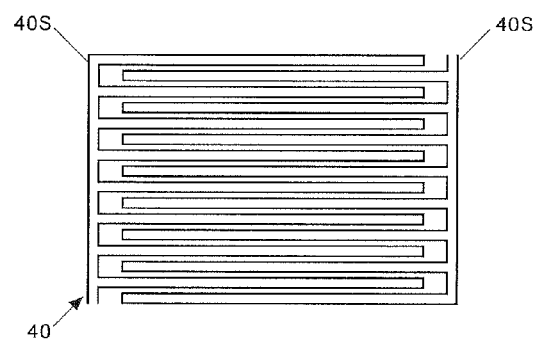
FIGS. 5A to 5F are schematic top views of exemplary counter units incorporated into pixels of various EMC display systems while also functioning as such pixels according to the present invention.
Figure 5B:
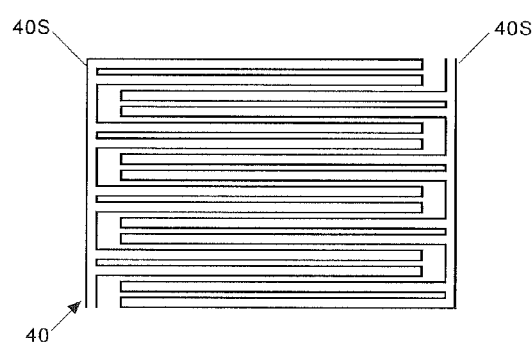
Figure 5C:
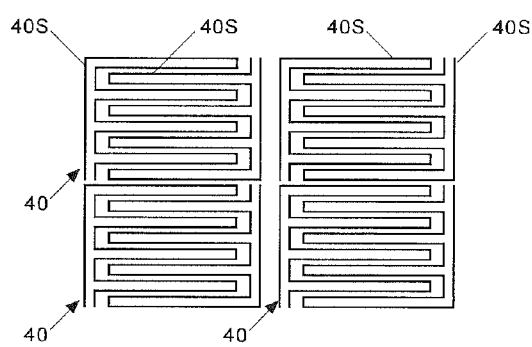

In another aspect of the present invention, an EMC display system may include light emitting or transmitting elements each of which may operate as the base unit irradiating the harmful waves while simultaneously functioning as the counter unit such that the harmful waves irradiated thereby function as the counter waves with respect to such harmful waves from other elements, where examples of such display units may include, but not be limited to, the OLED units, IOLED units, PDP units, LCD units, CRT units, DLP units, SED units, and the like. Therefore, any conventional display units including such EMC display units therein may then be converted into the EMC display systems such as, e.g., the EMC OLED systems, EMC IOLED systems, EMC PDP systems, EMC LCD systems, EMC CRT systems, EMC DLP systems, EMC SED systems, and the like. In addition, other conventional display units which emit and/or transmit the visible light rays through their pixels may similarly be converted to the EMC display systems by incorporating therein one or more of such counter units. FIGS. 5A to 5F show schematic top views of exemplary counter units incorporated into pixels of various EMC display systems while also functioning as such pixels according to the present invention. It is to be understood in all of such figures that only the electrodes and pixels are selected as the primary base units of such EMC display system. It is appreciated, therefore, that other conductive, semiconductive, and/or insulative parts of any EMC display systems irradiating the harmful waves are omitted therefrom and, when necessary, such parts may be properly countered by resorting to any of such counter units as described above. It is also appreciated for the simplicity of illustration that each figure depicts only a portion of the EMC display system by including a pair of pixels of the above display units and that neighboring regions of the EMC system not included in each figure may include the electrodes and pixels similar or identical to those included in the figure. In one exemplary embodiment of this aspect of the invention, an EMC display system includes multiple (sets of) pixels, at least one first electrode, and at least one second electrode, where at least one of the electrodes may be arranged to define a configuration capable of countering each other. In one example of FIG. 5A, a first (or second) electrode consists of multiple electrically conductive paths each of which extends horizontally and electrically couples with each row of pixels or with each set of pixels (both not included in the figure). In this regard, such paths may look similar to those of FIGS. 1A to 1C. However, these conductive paths are coupled to each other in an alternating mode that all odd-numbered horizontal paths are coupled to a vertical path provided on their left, whereas all even-numbered horizontal paths are coupled to another vertical path provided on their right. Assuming that the left vertical path flows the electric current from bottom to top and that the right vertical path flows the current in an opposite direction, the electric current flows through the adjacent horizontal paths in opposite directions. Therefore, the harmful waves irradiated by, e.g., the second horizontal path may be countered by the counter waves emitted by, e.g., the first or third horizontal path or vice versa. In this respect, any horizontal and/or vertical paths may be not only the base units themselves but also the counter units with respect to other paths adjacent thereto. In a related example of FIG. 5B, a first (or second) conductive path is similar to that of FIG. 5B. However, the horizontal paths thereof couple with each other in another alternating mode that each pair of such paths are alternatingly coupling to the left or right vertical path. Accordingly, the harmful waves irradiated by an upper member of, e.g., the second pair of horizontal paths are countered by the counter waves emitted from a lower member of the first pair of paths, while the harmful waves irradiated from a lower member of the second pair are countered by the counter waves emitted by an upper member of the third pair of paths. It is again appreciated that the harmful waves irradiated by one of the paths may function as the counter waves for the harmful waves irradiated by another path adjacent thereto and, accordingly, that any of these paths may be viewed as the base units in themselves as well as the counter units with respect to the other base units. In another related example of FIG. 5C, an EMC display system also includes multiple counter units 40 each of which is similar or identical to that of FIG. 5A but provided in a smaller scale. Accordingly, the horizontal paths included in each counter unit 40 counter each other and, in addition, neighboring vertical paths of the adjacent counter units 40 may also counter each other. A pinnacle feature of such embodiments of FIGS. 5A to 5C is that neighboring electrodes are arranged to counter each other due to their configurations and dispositions as long as the source (and counter) electrical energy is supplied thereto in proper directions. In this context, these electrodes and their paths will now be referred to as the "self-countering electrodes," as the "self-countering conductive paths" or as the "self-countering base units" hereinafter. In these embodiments, such base units correspond to the counter units (and vice versa), and the source electrical energy becomes identical to the counter electrical energy.

Figure 5D:
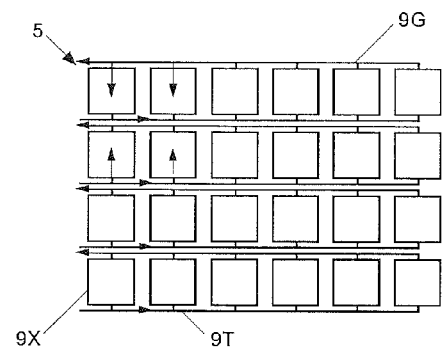
Figure 5E:
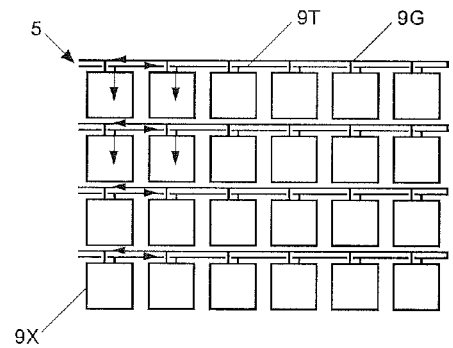
Figure 5F:
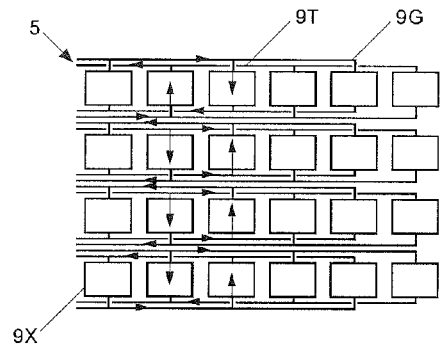

It is appreciated that the self-countering electrodes and paths shown in FIG. 5A are arranged to supply the source electrical energy in the direction vertical to the sheet. Accordingly and in another exemplary embodiment of this aspect of the invention, such self-countering arrangements may also be applied to such electrodes and paths which are arranged to supply the source electrical energy along lateral directions through opposite sides of various light emitting elements. In one example of FIG. 5D, an EMC display system 5 includes multiple pixels 9X each electrically coupling with the first path 9G on its top and the second path 9T on its bottom. The first and second paths 9G, 9T are also arranged so that the source electrical energy is supplied thereto and then flows out thereof in opposite directions. Therefore, the second path 9T for a given row of such pixels 9X and the first path 9G of an adjacent row thereof irradiate the harmful waves which counter each other. A manifest advantage of such an arrangement is that these self-countering electrodes and paths may be fabricated in a single layer. In a related example of FIG. 5E, the first and second paths 9G, 9T are typically similar to those of FIG. 5D, except that the paths 9G, 9T are provided one over another. Other than that such paths 9G, 9T have to be provided in a multilayer configuration, other configurational and/or operational characteristics of the arrangement of FIG. 5E are similar or identical to those of the arrangement of FIG. 5D. In another related example of FIG. 5F, the first and second paths 9G, 9T may be viewed as a hybrid of those of FIGS. 5D and 5E. More particularly, the pixels 9X of a given row are provided with the source energy in alternating directions, and the first and second paths 9G, 9T are fabricated in order to support such directions. An additional advantage of this arrangement over the arrangements of FIGS. 5D and 5E is that not only the conductive paths 9G, 9T but also such pixels 9X are arranged to counter each other, thereby maximizing a countering efficiency. Its only drawback, however, may be that this embodiment needs more conductive paths than those of FIGS. 5D and 5E. Other configurational and/or operational characteristics of the arrangement of FIG. 5F may be similar or identical to those of the arrangements of FIGS. 5D and 5E. When desirable and feasible, the arrangements of FIGS. 5D to 5F may be applied to those EMC display systems which have been disclosed in FIGS. 3A to 3O, FIGS. 4A to 4F, and FIGS. 5A to 5C and which have not been included in those figured but described in conjunction therewith.

Configurational and/or operational variations of various EMC display systems and their counter units and configurational and/or operational modifications of such EMC systems and their counter units as exemplified in FIGS. 2A to 2L, FIGS. 3A to 3O, FIGS. 4A to 4F, and FIGS. 5A to 5F and as disclosed hereinabove without any accompanying figures also fall within the scope of the present invention.

As described above, such counter units may be provided in various shapes and/or sizes and operate in the local or global countering mechanism. For example, a single counter unit for the entire system may be viewed as the globally countering counter unit, whereas the counter units provided in the same or similar number of the base units may be viewed as the locally countering counter units. In general, the EMC display system includes numerous base units which may be parts of the electrodes, pixels, and other electric and/or electronic components thereof. Therefore, such counter units, unless provided as a single unit, may be viewed to operate in both of the countering mechanisms. In another example, various counter units of this invention may be provided as unitary articles with various base units to be countered thereby. Considering that most of such pixels and their electrodes are currently manufactured through the conventional semiconductor fabrication process and that these electrodes and pixels have dimensions ranging from microns down to even nanometers, it is generally preferable to incorporate any of these counter units during manufacturing the above display units including such base units. However, this does not exclude any possibility of providing the counter units independent of the display units and then retrofitting the counter units into and/or around the prior art display units. For example, the counter units operating in the global countering mechanisms such as, e.g., those of FIGS. 4A to 4F, may be disposed over the screen of such display units. In another example, the self-countering arrangements of FIGS. 5A to 5F may be incorporated into any prior art display units such as, e.g., the OLED units, IDLED units, LCD units, PDP units, DLP units, SED units, and so on. Since this generally requires nothing but slightly longer conductive paths, the self-countering arrangements may be readily incorporated into various manufacturing processes and provide the EMC OLED units, EMC IDLED units, EMC LCD units, EMC PDP units, EMC DLP units, EMC SED units, and the like.

It is appreciated that any of the counter units described hereinabove may not be supplied with the electric energy and, therefore, may not actively emit the counter waves in response to the energy. Rather, the counter units may define the above configurations and may be in the above disposition so that the harmful waves irradiated by various base units may be absorbed into such counter units and converted to the electric voltage and/or current, thereby reducing the amount of such harmful waves propagating to the target space. Therefore, the EMC system may include one or multiple counter units all of which may serve as the passive counter units (i.e., those not receiving the electric energy), may include at least one passive counter unit and at least one active counter unit (i.e., one receiving such electric energy) or may include one or multiple counter units all of which serve as the active counter units. When desirable, at least one counter unit may also be arranged to serve as both of the active and passive counter units from time to time.

In another aspect of the present invention, any of the above EMC systems may include at least one electric shield and/or magnetic shield. In one example, the electric and/or magnetic shields (will be referred to as the "ES" and "MS" hereinafter, respectively) may be implemented into, on, over or below various portions of the EMC system. In another example, such ES and/or MS may also be implemented as above and also used in conjunction with any of the above counter units. In general, the ES may be made of and/or include at least one electrically conductive material such that the electric waves of the harmful waves may be absorbed thereinto and rerouted therealong. When desirable, the ES may also be grounded so that the absorbed and rerouted electric waves may be eliminated therefrom. The MS may be made of and/or include at least one magnetically permeable path member which may be able to absorb the magnetic waves of the harmful waves thereinto and then to reroute such magnetic waves therealong. When desirable, the MS may have a magnet member which may be magnetically coupled to the path member and terminate the absorbed and rerouted magnetic waves in at least one magnetic pole of the magnet member. The MS may include at least one optional shunt member which may also be magnetically permeable and shield its magnet member, thereby confining magnetic fields from such a magnet member closer thereto. Other details of such ES and MS have already been provided in the above co-pending applications such as, e.g., "Shunted Magnet Systems and Methods" which bears a Ser. No. 11/213,703, "Magnet-Shunted Systems and Methods" which also bears a Ser. No. 11/213,686, and "Electromagnetic Shield Systems and Methods" which bears a U.S. Ser. No. 60/723,274. It is appreciated that the details of these co-pending applications may be modified so that the heating elements of such co-pending applications may be replaced by various counter units of the present invention and that the ES and/or MS may be incorporated to the counter units of this invention as such ES and/or MS have been incorporated into various heating elements of the above co-pending Applications. It is appreciated that the ES and/or MS may also be incorporated into various portions of the EMC systems of this invention as the counter units are incorporated into such portions of the EMC systems of this invention.

The ES and/or MS may be provided to define the configuration which is identical to or similar to those of various counter units of this invention. The ES and/or MS may also be disposed in, on, over, around, and/or through the base and/or counter units. The ES and/or MS may have the configuration at least partially conforming to that of such base and/or counter units or, in the alternative, may define the configuration at least partially different from those of the ES and/or MS.

The path member of the MS may define the relative magnetic permeability greater than 1,000 or 10,000, 100,000 or 1,000,000. The shunt member may be arranged to directly or indirectly contact the magnet member and to define a relative magnetic permeability greater than 1,000, 10,000, 100,000 or 1,000,000. The ES and/or MS described hereinabove or disclosed in the co-pending applications may further be incorporated into any of the prior art devices with or without any of the above counter units and define such EMC systems of this invention. The ES and/or MS may define the configuration which may be maintained to be uniform along the longitudinal or short axis of the base and/or counter units or which may vary therealong. Such configurations of the ES and/or MS may be identical to, similar to or different from those of the base and/or counters. The EMC display system may have therein multiple ES and/or MS, where at least two of the MS and/or ES may shield against the magnetic waves and/or electric waves defining the same or different frequencies in same or different extents. The ES and/or MS may be disposed over at least a portion (or entire portion) of the base and/or counter units. The EMC system may also include one or more of any of such counter units and ES and/or MS, where the base and/or counter units may operate on AC or DC.

As described above, the EMC systems of this invention may be provided with multiple defense mechanisms against the harmful waves which are irradiated by various base units of such a system. In one example, the counter unit may be incorporated into various portions of such an EMC system as described above. Accordingly, a single or multiple counter units may be provided in any of the above configurations and incorporated in any of the above dispositions. In another example, such ES and/or MS may be incorporated into various portions of the EMC system and shield against the electric and/or magnetic waves of such harmful waves, respectively, where dispositions of the ES and/or MS have been described in the above co-pending Applications. In another example, not only the counter units but also at least one of the ES and/or MS may be implemented into the EMC system so that the counter unit may counter at least a portion of such harmful waves and that the ES and/or MS may absorb and reroute the rest thereof.

It is appreciated that any of the above counter units are provided while using the least amount of such electrically conductive, semiconductive, and/or insulative materials, while minimizing a volume, a size, and/or a mass of such counter units. Accordingly, such counter units may be fabricated with less materials at lower costs and may be easily implemented into various locations of the EMC display system. It is further appreciated that any of the counter units are provided to emit the counter waves while using the least amount of the electrical energy, e.g., by drawing the least amount of the electric current or voltage. Therefore, such counter units are not only energy-efficient but also least affecting force-generating and/or movement-generating operation of other parts of such EMC display systems. In addition, such requirements of this paragraph may minimize electric resistances of the counter units and, therefore, minimize voltage drop across the counter units.

Unless otherwise specified, various features of one embodiment of one aspect of the present invention may apply interchangeably to other embodiments of the same aspect of this invention and/or embodiments of one or more of other aspects of this invention. Therefore, any of the counter units of FIGS. 2A to 2L may be implemented to the EMC display systems of FIGS. 3A to 3O, FIGS. 4A to 4F, and FIGS. 5A to 5F, and other systems which have not been exemplified in conjunction with the figures but have been disclosed in conjunction therewith. Moreover, any of such counter units which operate on the source matching may be converted to operate based on the wave matching or vice versa, where the source-matched counter units may be disposed along (or across) one or more wavefronts of the harmful waves irradiated by at least one of the base units or where the wave-matched counter units may similarly be disposed in the preset relation to at least one of the base units or may be disposed in the arrangement similar to that of at least one of the base units. In addition, any of such counter units which are to counter a preset number (including 1) of pixels may be provided in a greater or smaller dimension in order to counter a greater or less number of pixels. Moreover, any of the electric and/or magnetic shields which have been disclosed hereinabove and also described in the above co-pending Applications may be incorporated into any of the above base units and/or counter units.

The EMC display systems of this invention may be powered by the AC electrical energy while countering the harmful EM waves with their counter units. When desirable, the EMC display systems may also be powered by the DC electrical energy while similarly countering such harmful waves with the counter units. It is appreciated that the EMC systems may use any conventional modalities capable of shielding and/or canceling the harmful waves. Therefore, it is prefer to braid, bundle, wind, and/or otherwise pair any extra wires, strips, plates, sheets, and other parts of the EMC display systems for minimizing irradiation of the harmful waves therefrom.

Although the above figures and descriptions have been centered around various counter units and various electric and/or magnetic shields to be incorporated to various EMC display systems, such counter units may be incorporated into other light emitting display devices which include similar waves sources and/or base units such as, e.g., the electron beam generator and the matching screen coated with the phosphor materials, arrays of the liquid crystal pixels, arrays of the organic and/or inorganic light emitting diodes, arrays of the phosphor pixels filled with ionizing gases releasing photons and/or electrons, and the like. Accordingly, such devices may be converted into the EMC display systems by incorporating thereto one or more of the above counter units.

Although a few embodiments of the present invention have been shown and described, it would be appreciated by those skilled in the art that changes may be made in this embodiment without departing from the principles and spirit of the invention, the scope of which is defined in the claims and their equivalents.

What is claimed is:

1. A method of displaying a visual image by an organic light emitting system operating on electric current while reducing an intensity of electromagnetic waves which are irradiated by said system and which are not visible light waves, said method comprising the steps of:
arranging a plurality of pixels in a preset pattern;
forming a first current path electrically connecting one end of each of said pixels;
forming a second current path electrically connecting another end of each of said pixels;
arranging said second path to run at least substantially along said first path; and
flowing said current in at least a portion of said first path in a first direction but in at least another portion of said second path in a second direction which is at least partially opposite to said first direction,
whereby said electromagnetic waves irradiated along said portion of second path cancel at least a portion of electromagnetic waves irradiated along said portion of said first path and whereby said intensity of said waves irradiated by said system is reduced.

2. The method of claim 1, further comprising the steps of:
electrically connecting said first path to said second path; and
flowing said current from one of said first and second paths to another thereof.

3. The method of claim 1, further comprising the step of:
forming at least one of said first and second paths in front of the other of said first and second paths.

4. The method of claim 1, further comprising the step of:
forming said first and second paths on opposite sides of said pixels.

5. The method of claim 1, further comprising the step of:
forming said first and second paths on the same side of said pixels.

6. A method of displaying a visual image by an organic light emitting system operating on electric current while reducing an intensity of electromagnetic waves which are irradiated by said system and which are not visible light waves, said method comprising the steps of:
arranging a plurality of pixels in a preset pattern;
selecting a group of said pixels which are arranged in a linear fashion and disposed adjacent to each other;
forming a first current path electrically connecting one end of each of said selected pixels;
forming a second current path electrically connecting another end of each of said selected pixels;
arranging at least portions of said first and second path at least partially parallel to each other; and
flowing said current in said portion of said first path in a first direction but in said portion of said second path in a second direction which is at least partially opposite to said first direction,
whereby said electromagnetic waves irradiated along said portion of second path cancel at least a portion of electromagnetic waves irradiated along said portion of said first path and whereby said intensity of said waves irradiated by said system is reduced.

7. The method of claim 6, further comprising the step of:
forming said first and second paths on opposite sides of said selected pixels.

8. The method of claim 6, further comprising the step of:
forming said first and second paths on the same side of said selected pixels.

9. A method of displaying a visual image by an organic light emitting system operating on electric current while reducing an intensity of electromagnetic waves which are irradiated by said system and which are not visible light waves, said method comprising the steps of:
arranging a first plurality of pixels in a first preset pattern;
forming a first current path electrically connecting one end of each of said pixels of said first plurality;
forming a second current path electrically connecting another end of each of said pixels of said first plurality;
arranging a second plurality of pixels in a second preset pattern;
forming a third current path electrically connecting one end of each of said pixels of said second plurality;
forming a fourth current path electrically connecting another end of each of said pixels of said second plurality;
arranging one of said paths of said second plurality to run at least substantially along one of said paths of said first plurality; and
flowing a second current in at least a portion of said one of said paths of said second plurality in a second direction but in at least a portion of said one of said paths of said first plurality in a first direction which is at least partially opposite to said second direction,
whereby said electromagnetic waves irradiated along said portion of said one of said paths of said second plurality cancel at least a portion of electromagnetic waves irradiated along said portion of said one of said paths first plurality and whereby said intensity of said waves irradiated by said system is reduced.

10. The method of claim 9, further comprising the step of:
forming said one of said paths of said second plurality adjacent to said one of said paths of said first plurality.

11. The method of claim 9, further comprising the step of:
forming said one of said paths of said second plurality and said one of said paths of said second plurality on opposite sides of said pixels.

12. The method of claim 9, further comprising the steps of:
electrically connecting said one of said paths of said second plurality to one of said paths of said first plurality; and
flowing said first current to said one of said paths of said second plurality.

13. The method of claim 9, further comprising the step of:
arranging said first plurality of said pixels parallel to said second plurality of said pixels.

14. The method of claim 9, wherein said first plurality is at least substantially identical to said second plurality.

15. The method of claim 9, wherein said first preset pattern is at least substantially identical to said second preset pattern.

16. The method of claim 9, further comprising the step of:
arranging a third plurality of pixels in a third preset pattern;
forming a fifth current path electrically connecting one end of each of said pixels of said third plurality;
forming a sixth current path electrically connecting another end of each of said pixels of said third plurality;

arranging one of said paths of said third plurality to run at least substantially along one of said paths of said second plurality; and flowing a third current in at least a portion of said one of said paths of said third plurality in a third direction which is at least partially opposite to said second direction.

17. The method of claim 16, further comprising the steps of:

electrically connecting said one of said paths of said third plurality to one of said paths of said second plurality; and flowing said second current to said one of said paths of said second plurality.

18. The method of claim 16, further comprising the steps of:

arranging said third plurality of said pixels parallel to said second plurality of said pixels.

19. The method of claim 16, wherein said third plurality is at least substantially identical to said second plurality.

20. The method of claim 16, wherein said third preset pattern is at least substantially identical to said second preset pattern.

\* \* \* \* \*